(12) United States Patent
Marshall et al.

(10) Patent No.: US 12,004,939 B1
(45) Date of Patent: Jun. 11, 2024

(54) TRANSCATHETER GROWTH DEVICES AND METHODS FOR NORWOOD, GLENN AND FONTAN THERAPY

(71) Applicant: Renata Medical, Inc., Newport Beach, CA (US)

(72) Inventors: Corey Marshall, Newport Beach, CA (US); Eason Abbott, Santa Monica, CA (US); Dustin Armer, Costa Mesa, CA (US); Jordan Roy, Huntington Beach, CA (US); Evan Zahn, Los Angeles, CA (US); Rani Mahmoudi, Huntington Beach, CA (US)

(73) Assignee: Renata Medical, Inc., Newport Beach, CA (US)

( * ) Notice: Subject to any disclaimer, the term of this patent is extended or adjusted under 35 U.S.C. 154(b) by 0 days.

(21) Appl. No.: 18/532,943

(22) Filed: Dec. 7, 2023

Related U.S. Application Data

(60) Provisional application No. 63/431,616, filed on Dec. 9, 2022.

(51) Int. Cl.
*A61F 2/07* (2013.01)
*A61F 2/06* (2013.01)
(Continued)

(52) U.S. Cl.
CPC .............. *A61F 2/064* (2013.01); *A61F 2/07* (2013.01); *A61F 2002/0081* (2013.01);
(Continued)

(58) Field of Classification Search
CPC .. A61F 2/064; A61F 2/07; A61F 2/966; A61F 2002/0081; A61F 2002/061;
(Continued)

(56) References Cited

U.S. PATENT DOCUMENTS

| 4,733,665 A | 3/1988 | Palmaz |
| 5,868,782 A * | 2/1999 | Frantzen ................. A61F 2/915 606/1 |

(Continued)

FOREIGN PATENT DOCUMENTS

| CN | 106333768 A | 1/2017 |
| JP | S62-231657 A | 10/1987 |

(Continued)

OTHER PUBLICATIONS

International Search Report and Written Opinion in PCT/US2023/082942, mailed Apr. 3, 2024, 16 pages.

*Primary Examiner* — Suba Ganesan
(74) *Attorney, Agent, or Firm* — Orrick, Herrington & Sutcliffe LLP

(57) ABSTRACT

A transcatheter growth device for treating congenital illnesses in infantile and other pediatric heart disease patients and methods for making and using the same. The growth device includes an elongated device frame with alternating annular growth cell members and spacing members that axially span proximal and distal end regions of the device frame. The growth cell members and spacing members define a radial periphery for the growth device. Each growth cell member can comprise a scaffolded growth cell member with first and second annular strut arrangements coupled via a growth cell junction to provide device frame flexibility. A retention member for engaging a selected lumen within a patient and a covering member for sealing the growth device, when deployed, are disposed at the device periphery. The growth device advantageously can be deployed for treating heart disease alone or in combination with one or more additional growth devices.

28 Claims, 72 Drawing Sheets

(51) Int. Cl.
*A61F 2/00* (2006.01)
*A61F 2/82* (2013.01)
*A61F 2/915* (2013.01)
*A61F 2/958* (2013.01)
*A61F 2/966* (2013.01)

(52) U.S. Cl.
CPC ... *A61F 2002/061* (2013.01); *A61F 2002/821* (2013.01); *A61F 2002/826* (2013.01); *A61F 2002/91541* (2013.01); *A61F 2002/91558* (2013.01); *A61F 2002/9583* (2013.01); *A61F 2/966* (2013.01); *A61F 2220/0008* (2013.01); *A61F 2250/0065* (2013.01); *A61F 2250/0082* (2013.01)

(58) Field of Classification Search
CPC .......... A61F 2002/821; A61F 2002/826; A61F 2002/91541; A61F 2002/91558; A61F 2002/9583; A61F 2220/0008; A61F 2250/0065; A61F 2250/0082
See application file for complete search history.

(56) References Cited

U.S. PATENT DOCUMENTS

| | | |
|---|---|---|
| 6,942,690 B1 | 9/2005 | Pollock et al. |
| 7,156,869 B1 | 1/2007 | Pacetti |
| 7,318,837 B2 | 1/2008 | Krivoruchko et al. |
| 8,512,395 B2 | 8/2013 | Meyer et al. |
| 8,647,378 B2 | 2/2014 | Mews et al. |
| 8,870,943 B2 | 10/2014 | Nielsen |
| 9,072,604 B1 | 7/2015 | Melnick et al. |
| 9,364,322 B2 | 6/2016 | Conklin et al. |
| 9,375,310 B2 | 6/2016 | Chung et al. |
| 9,381,103 B2 * | 7/2016 | Abunassar ............... A61F 2/915 |
| 9,655,752 B2 | 5/2017 | Shanov et al. |
| 9,737,422 B2 | 8/2017 | Armstrong et al. |
| 10,022,252 B2 | 7/2018 | Shields et al. |
| 10,080,653 B2 | 9/2018 | Conklin et al. |
| 10,220,192 B2 | 3/2019 | Drasler et al. |
| 10,543,085 B2 | 1/2020 | Chung et al. |
| 10,702,407 B1 | 7/2020 | Armer et al. |
| 2002/0128706 A1 | 9/2002 | Osypka |
| 2003/0040792 A1 | 2/2003 | Gabbay |
| 2003/0065386 A1 | 4/2003 | Weadock |
| 2004/0186554 A1 * | 9/2004 | Banas ....................... A61F 2/91 623/1.15 |
| 2006/0100695 A1 | 5/2006 | Peacock, III et al. |
| 2006/0259132 A1 | 11/2006 | Schaffer et al. |
| 2008/0004696 A1 | 1/2008 | Vesely |
| 2008/0114452 A1 | 5/2008 | Gabbay |
| 2008/0154351 A1 | 6/2008 | Leewood et al. |
| 2008/0177373 A1 | 7/2008 | Huang et al. |
| 2008/0221666 A1 | 9/2008 | Licata et al. |
| 2008/0262594 A1 | 10/2008 | Morris |
| 2009/0118810 A1 | 5/2009 | Klein et al. |
| 2009/0248133 A1 | 10/2009 | Bloom et al. |
| 2009/0254176 A1 | 10/2009 | Butera |
| 2010/0040663 A1 | 2/2010 | McAllister et al. |
| 2010/0049300 A1 | 2/2010 | Harder |
| 2010/0049306 A1 | 2/2010 | House et al. |
| 2010/0122698 A1 | 5/2010 | Shaffer et al. |
| 2010/0256737 A1 | 10/2010 | Pollock et al. |
| 2011/0264194 A1 | 10/2011 | Griswold |
| 2012/0158125 A1 | 6/2012 | Obradovic |
| 2013/0073023 A1 | 3/2013 | Mongrain et al. |
| 2013/0138206 A1 | 5/2013 | Sudhir et al. |
| 2013/0211489 A1 | 8/2013 | Makower et al. |
| 2013/0274872 A1 | 10/2013 | Vesely |
| 2015/0202065 A1 | 7/2015 | Shalev et al. |
| 2016/0008130 A1 | 1/2016 | Hasin |
| 2017/0000603 A1 | 1/2017 | Conklin et al. |
| 2017/0014228 A1 | 1/2017 | Emani et al. |
| 2017/0216062 A1 | 8/2017 | Armstrong et al. |
| 2018/0140444 A1 | 5/2018 | Neuss et al. |
| 2018/0185147 A1 | 7/2018 | Delaloye |
| 2018/0200041 A1 | 7/2018 | Rasmussen et al. |
| 2018/0325651 A1 | 11/2018 | Sumanasinghe et al. |
| 2019/0125517 A1 | 5/2019 | Cully et al. |
| 2019/0133764 A1 | 5/2019 | Carr et al. |
| 2019/0231510 A1 * | 8/2019 | Rafiee ................... A61L 27/507 |
| 2020/0368017 A1 | 11/2020 | Hofferberth et al. |
| 2022/0110773 A1 | 4/2022 | Labrecque et al. |
| 2022/0125581 A1 | 4/2022 | Justino et al. |

FOREIGN PATENT DOCUMENTS

| | | |
|---|---|---|
| JP | 2010-516348 A | 5/2010 |
| JP | 2011-125439 A | 6/2011 |
| JP | 2014-508559 A | 4/2014 |
| JP | 2018-516735 A | 6/2018 |
| WO | 2008/089446 A2 | 7/2008 |
| WO | 2019/033026 A1 | 2/2019 |

* cited by examiner

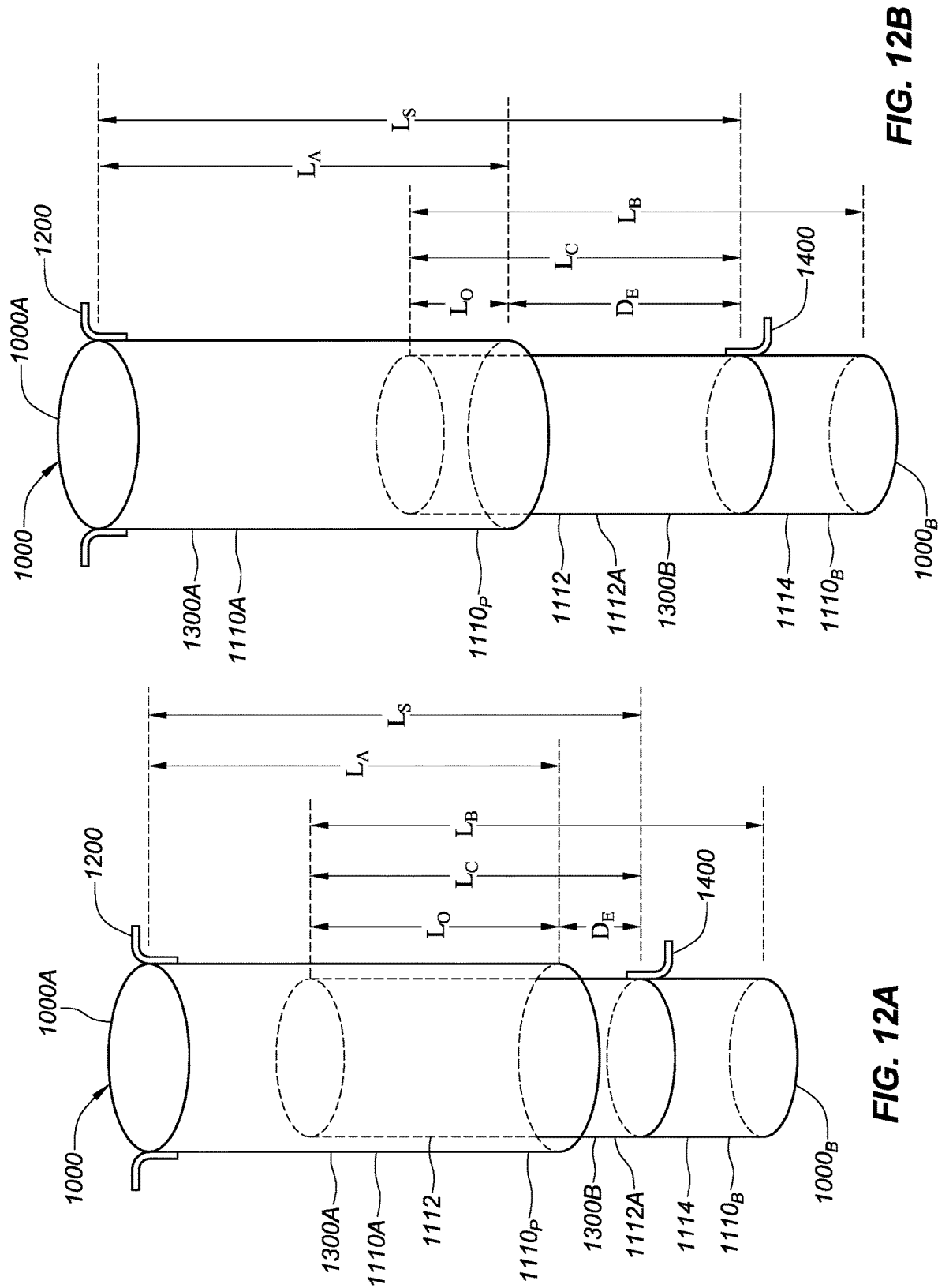

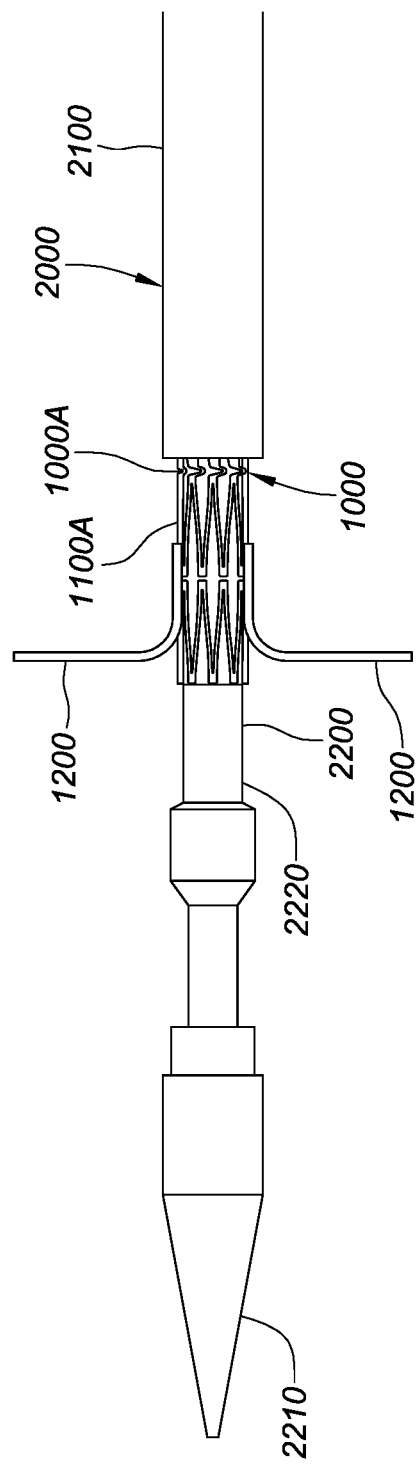

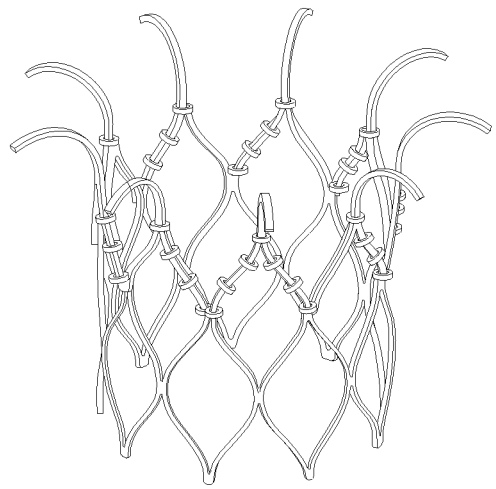
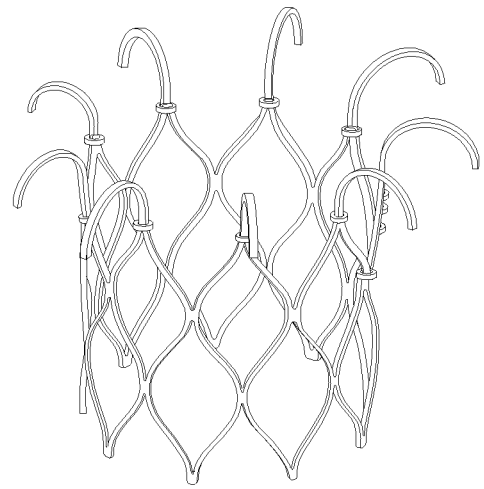
FIG. 19A
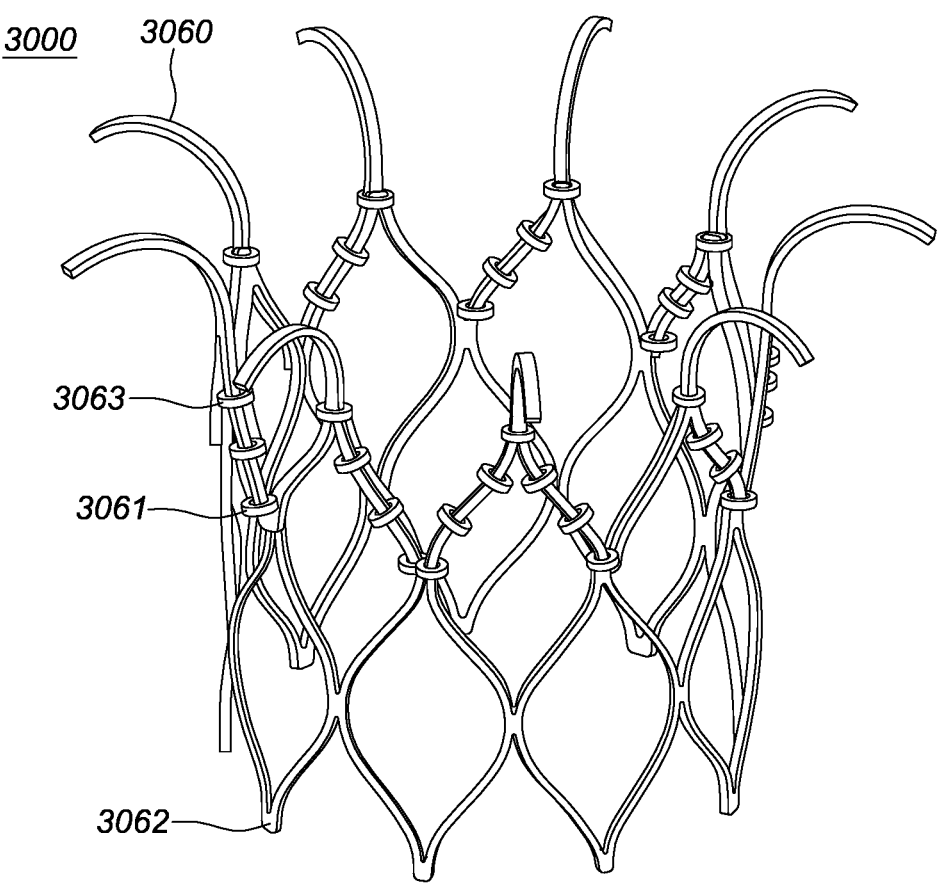
FIG. 19B

A - Swartz SL
B - Abbott
C - NRG RF transseptal
D - TSP Crosser Kit

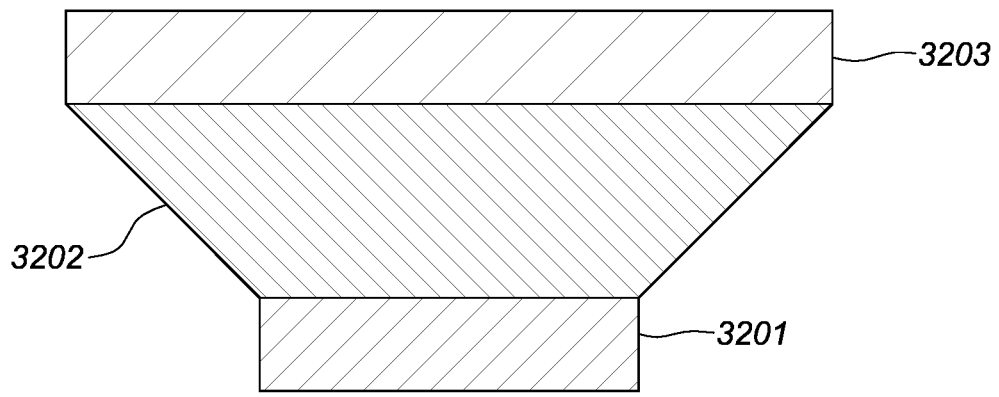
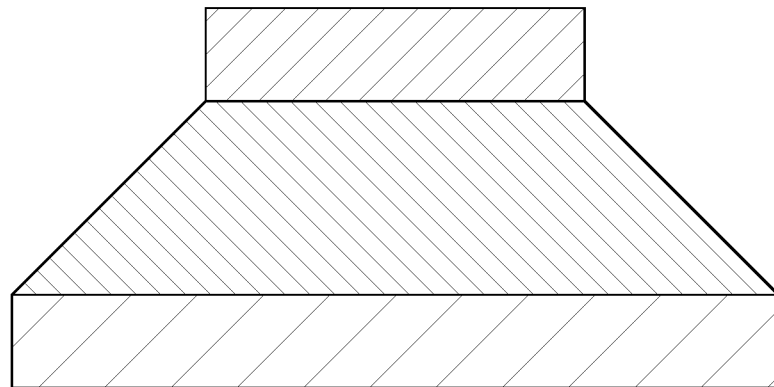
FIG. 33B

TRANSCATHETER GROWTH DEVICES AND METHODS FOR NORWOOD, GLENN AND FONTAN THERAPY

CROSS-REFERENCE TO RELATED APPLICATIONS

This application claims the benefit of, and priority to, U.S. Provisional Application Ser. No. 63/431,616, filed on Dec. 9, 2022, the disclosure of which is hereby incorporated herein by reference in its entirety and for all purposes.

FIELD

The disclosed embodiments relate generally to the field of medical devices and more particularly, but not exclusively, to transcatheter growth Norwood, Glenn and Fontan devices, including medical stent, shunt and occlusion devices, for implantation in pediatric patients and later expanded to adult vessel sizes.

BACKGROUND

Transcatheter and surgical shunts, stents, and occluding devices have been used for many years to treat patients by diverting blood flow in a more hemodynamically favorable manner. Congenital heart disease patients suffering from general congenital illnesses (or conditions), such as Hypoplastic Left Heart Syndrome, Tricuspid Atresia and other single-ventricle diseases, currently may undergo three-staged surgeries over the course of their childhood to treat their general congenital conditions. Such conditions, if left untreated, can eventually lead to serious cardiovascular compromise or death.

For many years, the definitive treatment for these general congenital conditions was the surgical repair and creation of blood flow diverters, conduits, and shunts through open heart surgery, but such surgeries are dangerous and prone to complication. Open-heart surgery in neonatal and other pediatric patients, however, may lead to negative developmental effects. Patients may undergo one or more of the three-staged surgeries for treating these general congenital conditions in any representative fashion, whether an individual procedure, a paired procedure, or all three procedures. The three staged procedures are shown and described with reference to FIGS. 1A-D.

The first procedure of the three-staged surgeries that these pediatric patients often experience is the Norwood procedure, which is performed almost immediately after a patient is born. The Norwood procedure is illustrated in FIG. 1B and entails creation of a single outflow vessel and valve that delivers oxygenated blood to the rest of the body, creating a large orifice between the atrial septal walls to allow for blood to mix and flow into a single ventricle. A Blalock-Taussig (or BT) or a Sano shunt is surgically created to allow for adequate pressure in the pulmonary arteries of the patient. This shunt reduces the cardiovascular load on the congenital single ventricle while allowing for stabilized blood flow. The Norwood procedure creates a resized aorta to pump blood to the body of the patient.

The second procedure is the Glenn procedure, which is performed around six months after birth of the patient. The Glenn procedure is illustrated in FIG. 1C. In this procedure, a shunt is created between the pulmonary artery and the superior vena cava (or SVC) of the patient to allow for passive flow of deoxygenated blood to the lungs. Along with the shunt formation, the SVC is then occluded to block off deoxygenated blood flow from the upper body into the single ventricle. The BT or Sano shunt created during the prior Norwood procedure must be occluded as well. The Glenn procedure thereby permits passive deoxygenated blood to pass from the upper body to the lungs, which preparing the anatomy of the patient for the respective third procedure, the Fontan procedure. In other words, the Glenn procedure enables the single ventricle to only pump blood to the body while blood passively fills the lungs for oxygenation.

FIG. 1D shows the Fontan procedure, which is performed between two to six years after the patient is born. This procedure is palliative and can allow for all deoxygenated blood, from upper and lower body, to passively flow into the lungs of the patient to become oxygenated blood. In the Fontan procedure, the inferior vena cava (or IVC) is occluded from the right atrium, and a conduit is created to divert the blood from the IVC to the SVC. The Fontan procedure re-routes blood flow so that there is no mixing of oxygen-rich and oxygen-poor blood.

Each of the three procedures comprise invasive surgical procedure, which require healing time and cause pain for the patients. With the advancement in transcatheter techniques and devices such as ballooning, shunting, and stenting, developing device and therapeutic technology to eliminate these procedures could decrease the healing time and pain for patients with congenital heart disease. Transcatheter devices and techniques, specifically ones that eliminate open-heart and heart bypass surgery, have shown to reduce complications and mortality.

Furthermore, there is currently no commercially available option for performing a Norwood, Glenn and Fontan procedure through a transvascular or transcatheter technique, and there is no specific implant or catheter system that has been designed and implanted specifically for neonates, infants, babies, toddlers, young (or small) children, or other pediatric patients and/or congenital patients who have been diagnosed with single ventricle disease or other related diseases.

In view of the foregoing, a need exists for transcatheter growth devices and methods for treating general congenital illnesses in heart disease patients, particularly in infantile and other pediatric heart disease patients, that overcome the aforementioned obstacles and deficiencies of currently-available three-staged invasive surgical procedure.

BRIEF DESCRIPTION OF THE DRAWINGS

FIG. 12A is a top-level drawing illustrating an exemplary alternative embodiment of the growth devices of FIGS. 11A-B, wherein the second growth device is disposed within the first growth device by a first predetermined overlap distance.

FIG. 12B is a top-level drawing illustrating another exemplary alternative embodiment of the growth devices of FIGS. 11A-B, wherein the second growth device is disposed within the first growth device by a second predetermined overlap distance.

FIGS. 14E-G are detail drawings illustrating an exemplary alternative embodiment of the delivery catheter system of FIGS. 14A-D, wherein the growth device is disposed on the delivery catheter system.

FIGS. 19A-C are detail drawings illustrating an exemplary embodiment of a transcatheter growth device, wherein the transcatheter growth device includes a dual material shunt implant containing a self-expanding metal material like nitinol and a balloon-expandable metal material like cobalt chrome to create a balloon-expandable growth implant with fixation hooks or flares.

FIGS. 33A-D are detail drawings illustrating an exemplary embodiment of a dual frame implant device for restricting flow in the PA.

Figure 1A:
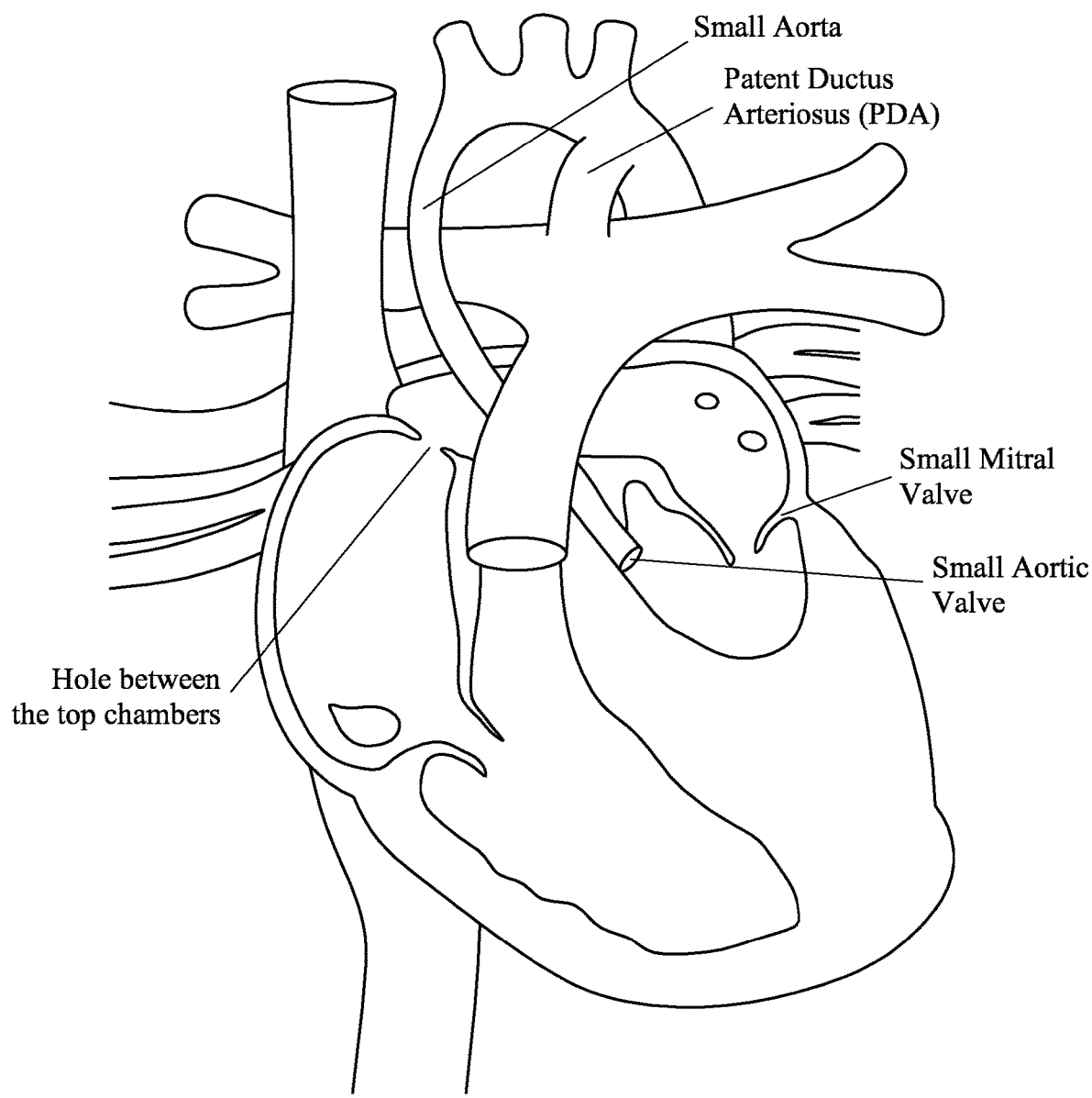
FIGS. 1A-D illustrate three staged procedures: the Norwood procedure; the Glenn procedure and the Fontan procedure.
Figure 1B:
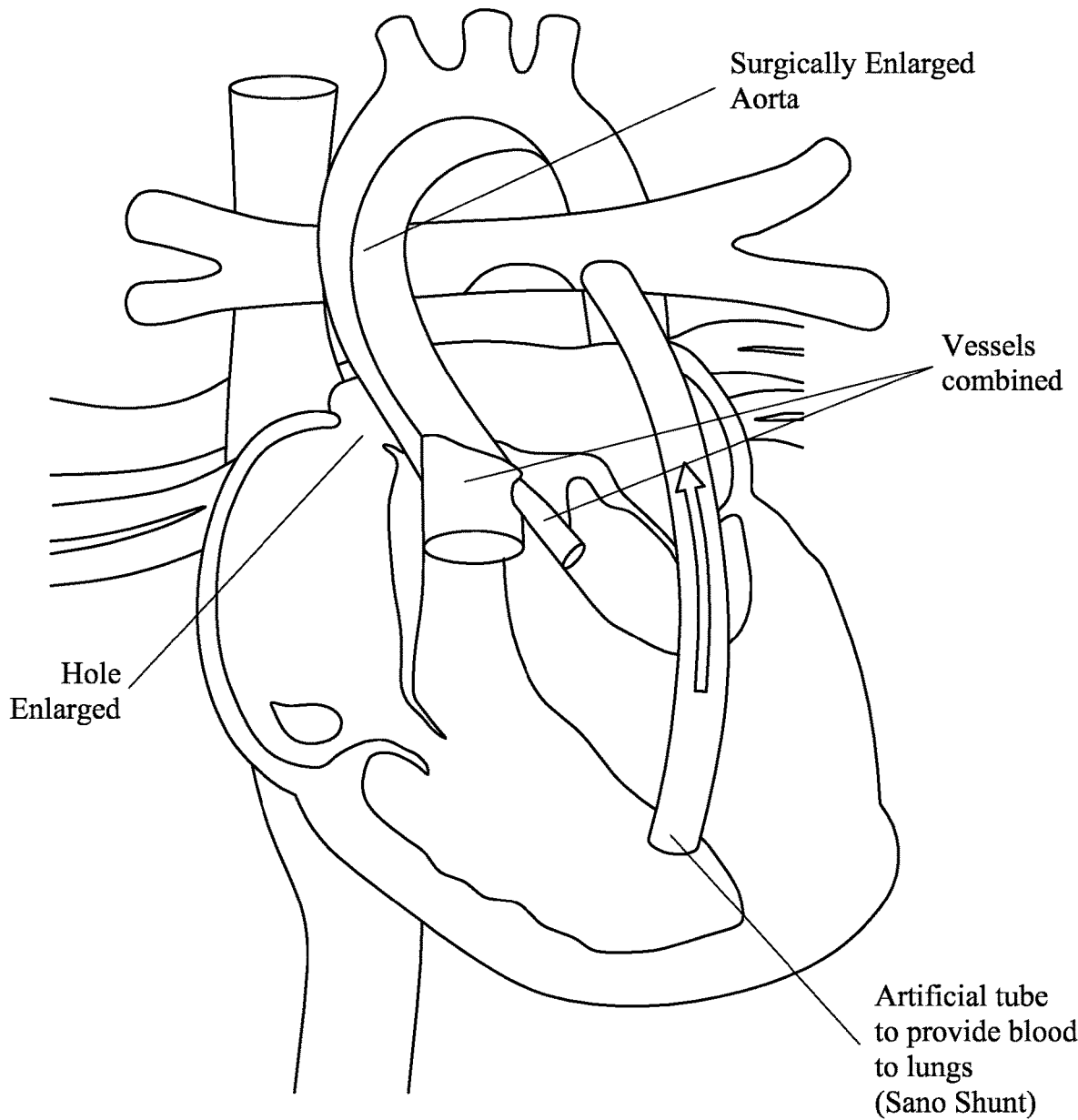
Figure 1C:
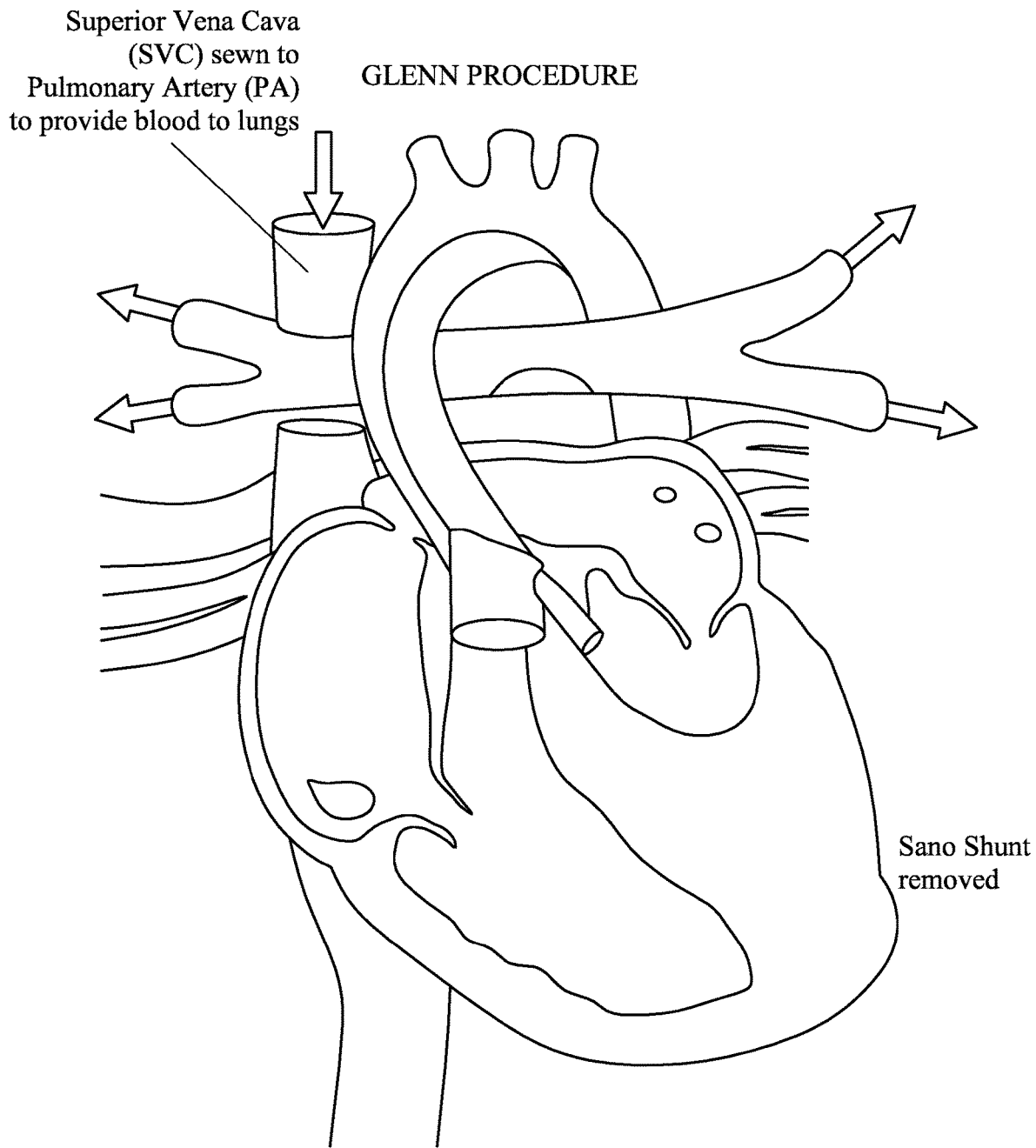
Figure 1D:
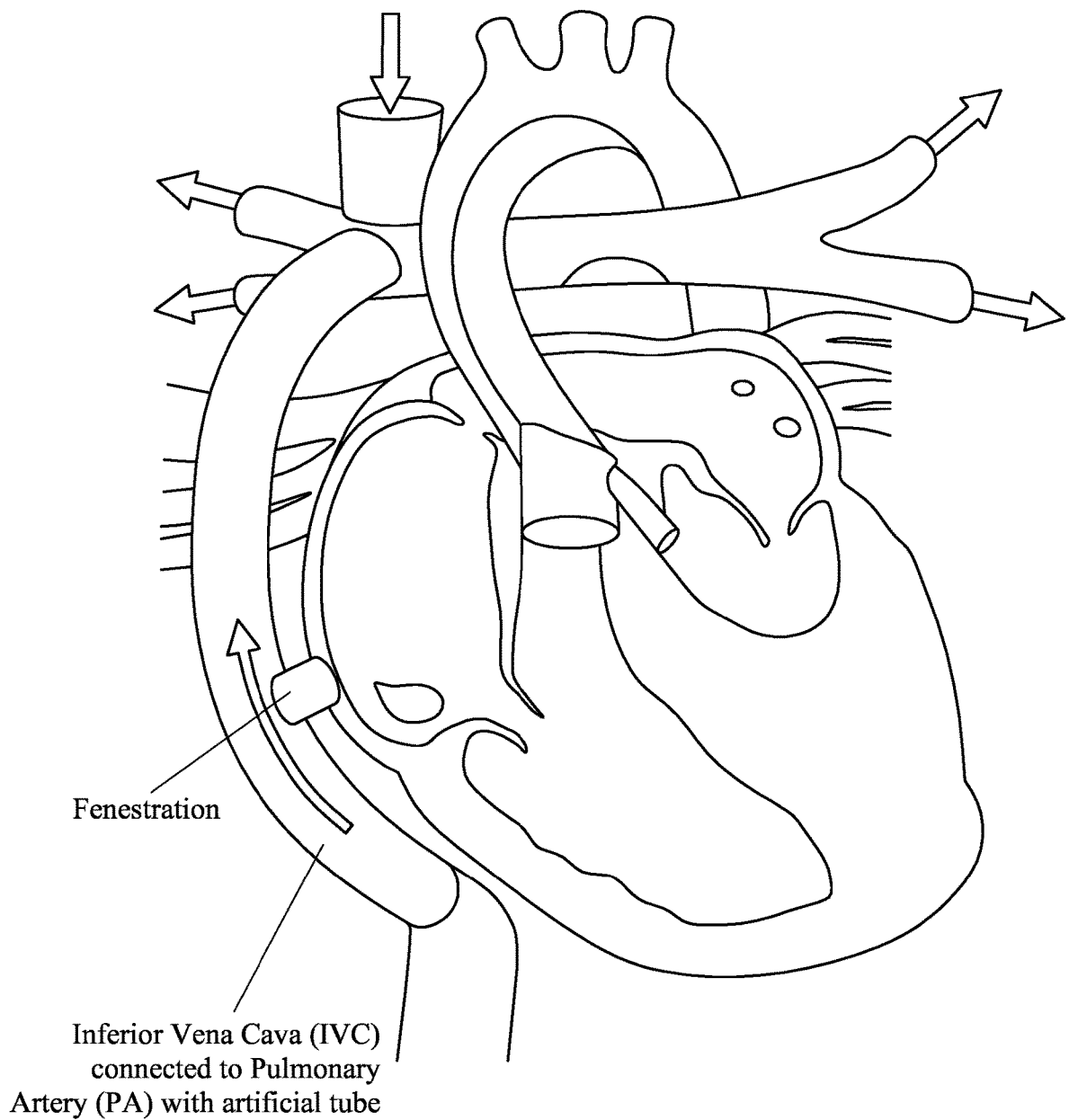

It should be noted that the figures are not drawn to scale and that elements of similar structures or functions are generally represented by like reference numerals for illustrative purposes throughout the figures. It also should be noted that the figures are only intended to facilitate the description of the preferred embodiments. The figures do not illustrate every aspect of the described embodiments and do not limit the scope of the present disclosure.

DETAILED DESCRIPTION OF THE PREFERRED EMBODIMENTS

Since the currently-available three-staged surgical procedure for treating the general congenital illnesses of congenital heart disease patients is invasive, requires healing time and causes pain for the patients, a transcatheter growth device and method for treating these general congenital illnesses can prove desirable and provide a basis for a wide range of applications, such as treating general congenital illnesses in infantile and other pediatric heart disease patients. This result can be achieved, according to one embodiment disclosed herein, by a transcatheter growth device 1000 for treating general congenital illnesses in infantile and other pediatric heart disease patients as shown in FIG. 2.

The growth device 1000, in selected embodiments, can allow a patient with a congenital heart disease leading to a single working ventricle to function optimally with respect to proper blood flow to the peripheral anatomy and to the lungs. Varied congenital disease states can be defined as single ventricle abnormality, such as Hypoplastic Left Heart Syndrome, Hypoplastic Right Heart Syndrome, Ebstein's Anomaly, tricuspid atresia, pulmonary atresia, and more. The growth device 1000 advantageously can be applied to other congenital heart diseases that require re-routing of blood flow in the heart.

Figure 2:
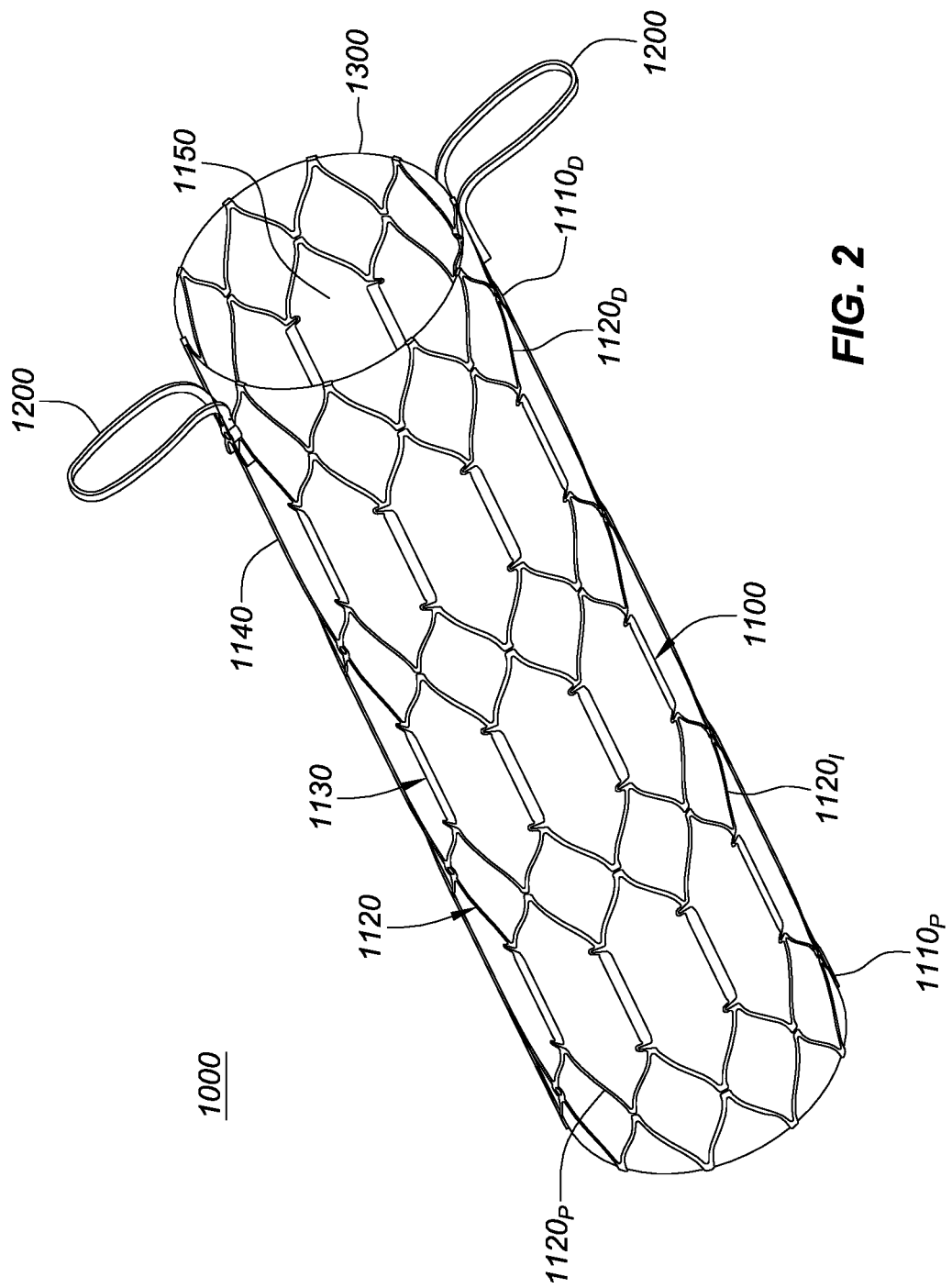
FIG. 2 is a detail drawing illustrating an exemplary embodiment of a growth device for treating general congenital illnesses in infantile and other pediatric heart disease patients.

Turning to FIG. 2, an exemplary embodiment of the growth device 1000 is shown as comprising an elongated device frame 1100. The device frame 1100 of FIG. 2 includes a plurality of annular growth cell members 1120 and one or more annular spacing members 1130. The growth cell members 1120 and the spacing members 1130 can define a periphery 1140 of the device frame 1100 and extend from a proximal end region $1110_P$ of the device frame 1100 to a distal end region $1110_D$ of the device frame 1100. As shown in FIG. 2, each spacing member 1130 can be disposed between a pair of adjacent growth cell members 1120. Stated somewhat differently, the device frame 1100 can comprise a series (or sequence) of alternating growth cell members 1120 and spacing members 1130 that span axially between the proximal and distal end regions $1110_P$, $1110_D$ and that can provide a radial periphery 1140 for the device frame 1100. The sequence of growth cell members 1120 and spacing members 1130 thereby can define a central axial channel 1150 of the elongated device frame 1100.

The growth cell members 1120 as shown in FIG. 2, for example, can include a proximal growth cell member $1120_P$ that is disposed at the proximal end region $1110_P$ of the device frame 1100 and a distal growth cell member $1120_D$ that is disposed at the distal end region $1110_D$ of the device frame 1100. The spacing member 1130 can be disposed between the proximal growth cell member $1120_P$ and the distal growth cell member 1120. In selected embodiments, the growth cell members 1120 can include an intermediate growth cell member $1120_I$ that is disposed between the proximal growth cell member $1120_P$ and the distal growth cell member 1120. A first spacing member 1130 can be disposed between the proximal growth cell member $1120_P$ and the intermediate growth cell member $1120_I$, and/or a second spacing member 1130 can be disposed between the intermediate growth cell member $1120_I$ and the distal growth cell member 1120. Additionally and/or alternatively, the growth cell members 1120 can include a plurality of intermediate growth cell members $1120_I$ with respective spacing members 1130 being disposed between adjacent intermediate growth cell members $1120_I$ as shown in FIG. 2.

Figure 3A:
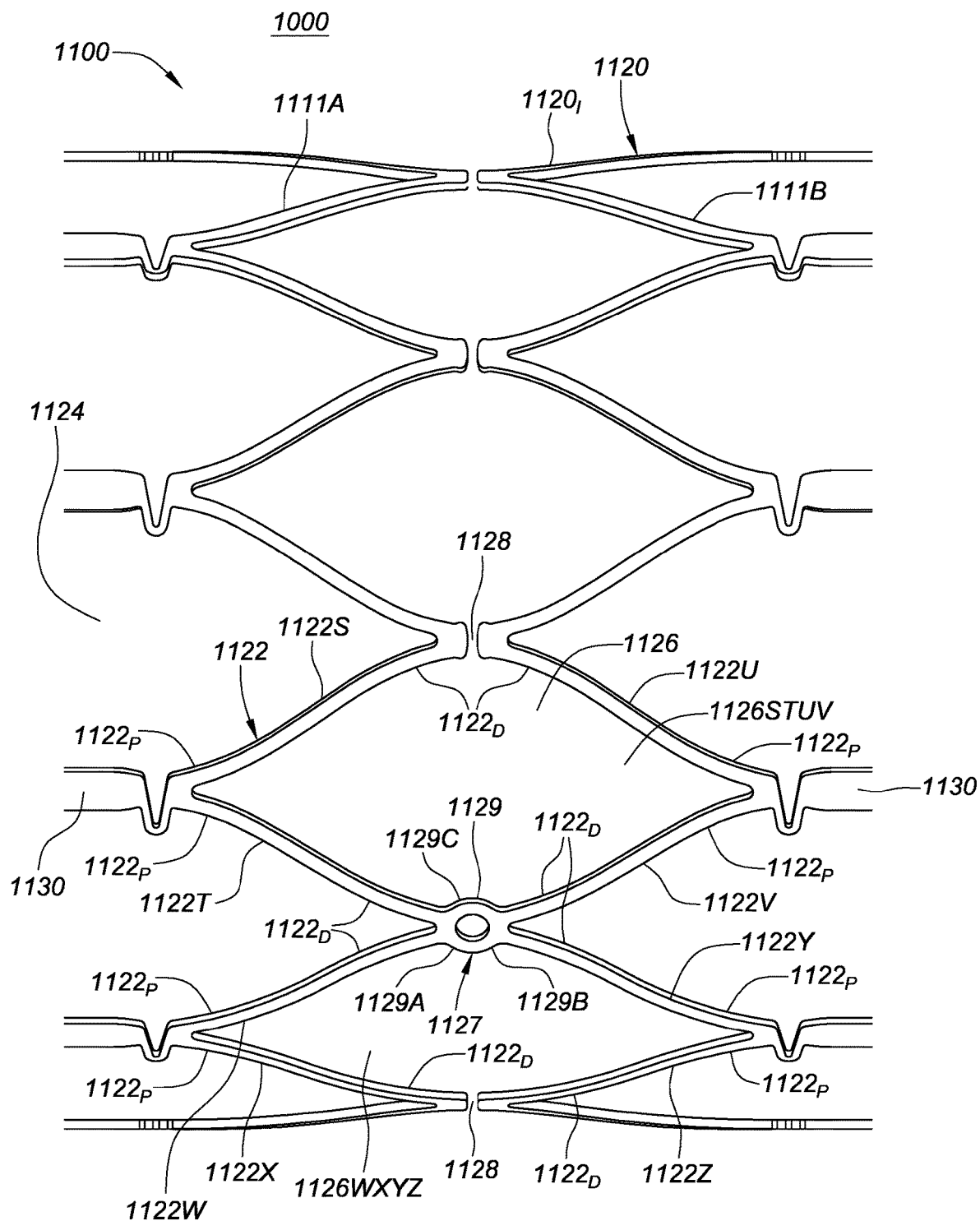
FIG. 3A is a detail drawing illustrating an exemplary embodiment of a growth cell member for the growth device of FIG. 2, wherein a first pair of coupled growth cell struts of the growth cell member is coupled with a second pair of coupled growth cell struts to form a growth cell junction.

The growth cell members 1120 of the device frame 1100 can have uniform structures and/or different structures, depending, for example, upon a predetermined application of the growth device 1000, an implant location of the growth device 1000 within a patient 100 (shown in FIG. 8) and/or an anatomy of the patient 100. In selected embodiments, the growth cell members 1120 can be formed from metal, metal alloys, polymer, biodegradable polymers, cloth, and/or a combination of multiple materials, without limitation. An exemplary growth cell member 1120 is illustrated in FIG. 3A. Turning to FIG. 3A, the growth cell member 1120 is shown as comprising a scaffolded growth cell member with a plurality of growth cell struts 1122 that can be disposed in a ring configuration for defining an internal growth cell opening 1124 of the growth cell member 1120.

The growth cell struts 1122 can have predetermined cell strut widths and/or predetermined cell strut thicknesses and/or can define one or more frame cells 1126. The cell strut widths and/or cell strut thicknesses can be increased to increase a radial strength of the growth cell member 1120 and/or can be decreased to decrease the radial strength of the growth cell member 1120. The frame cells 1126 advantageously can enable the growth device 1000 to be crimped to an implantation state with a predetermined initial size, shape, diameter, cross-section or other dimension as well as to expand to a (stable) expanded state with a predetermined expanded size, shape, diameter, cross-section or other dimension.

Exemplary initial dimensions of the growth device 1000 can include, but are not limited to, an initial dimension between one millimeter and four millimeters. The growth device 1000 in the expanded state can have a predetermined dimension that is between ten millimeters and thirty millimeters, without limitation. The growth device 1000 thereby can support a wide range of expansion ratios between the expanded state and the initial state. Based upon the preceding exemplary dimensions, an exemplary range of expansion ratios can comprise be between two and thirty. In selected embodiments, the growth device 1000 in the implantation state can be configured for deployment in a neonatal patient, an infantile patient, a baby patient, a small child patient or other pediatric patient. For pediatric patients, the expanded state can be equivalent to a vessel size of a congenital child.

In some embodiments, the device frame 1100 can comprise a balloon-expandable device frame 1100. The device frame 1100, in other embodiments, can comprise a self-expanding device frame using materials like nitinol and other metal alloys. The device frame 1100 advantageously can allow for further expansion as the patient grows. Although shown and described as comprising uniform cell strut widths, uniform cell strut thicknesses and/or uniform frame cells 1126 with reference to FIG. 3A for purposes of illustration only, the growth cell struts 1122 can include cell strut widths, cell strut thicknesses and/or frame cells 1126 that are uniform and/or different.

In selected embodiments, the growth cell struts 1122 can be provided as one or more pairs of growth cell struts 1122. Each pair of the growth cell struts 1122 optionally can be paired with one or more other paired growth cell struts 1122 of the growth cell member 1120 as illustrated in FIG. 3A. The paired growth cell struts 1122, for example, can include a first pair of growth cell struts 1122S, 1122T and a second pair of growth cell struts 1122U, 1122V. Each of the growth cell struts 1122S, 1122T, 1122U, 1122V can include a proximal end region $1122_P$ and a distal end region $1122_D$.

With reference to the first pair of growth cell struts 1122S, 1122T, the proximal end region $1122_P$ of the growth cell strut 1122S can be coupled with the proximal end region $1122_P$ of the growth cell strut 1122T with the distal end regions $1122_D$ of the growth cell struts 1122S, 1122T extending from the coupled proximal end regions $1122_P$. The proximal end regions $1122_P$ of the growth cell struts 1122U, 1122V of the second pair likewise can be coupled, and the distal end regions $1122_D$ of the growth cell struts 1122U, 1122V can extend from the coupled proximal end regions $1122_P$. As illustrated in FIG. 3A, the distal end region $1122_D$ of the growth cell strut 1122S of the first pair can be disposed adjacent to the distal end region $1122_D$ of the growth cell strut 1122U of the second pair; whereas, the distal end region $1122_D$ of the growth cell strut 1122T of the first pair can be disposed adjacent to the distal end region $1122_D$ of the growth cell strut 1122V of the second pair. The first and second pairs of growth cell struts 1122S, 1122T, 1122U, 1122V thereby can define a first frame cell 1126STUV.

The distal end region $1122_D$ of the growth cell strut 1122S of the first pair optionally can be coupled with the distal end region $1122_D$ of the growth cell strut 1122U of the second pair, and/or the distal end region $1122_D$ of the growth cell strut 1122T of the first pair optionally can be coupled with the distal end region $1122_D$ of the growth cell strut 1122V of the second pair. In selected embodiments, the distal end region $1122_D$ of the growth cell strut 1122S can be separate from the distal end region $1122_D$ of the growth cell strut 1122U with the distal end regions $1122_D$ as shown in FIG. 3A. The distal end region $1122_D$ of the growth cell strut 1122T optionally can be separate from the distal end region $1122_D$ of the growth cell strut 1122V with the distal end regions $1122_D$.

Additionally and/or alternatively, the paired growth cell struts 1122 can include a third pair of growth cell struts 1122W, 1122X and a fourth pair of growth cell struts 1122Y, 1122Z. Each of the growth cell struts 1122W, 1122X, 1122Y, 1122Z can include a proximal end region $1122_P$ and a distal end region $1122_D$. The proximal end region $1122_P$ of the growth cell strut 1122W can be coupled with the proximal end region $1122_P$ of the growth cell strut 1122X with the distal end regions $1122_D$ of the growth cell struts 1122W, 1122X extending from the coupled proximal end regions $1122_P$. The proximal end regions $1122_P$ of the growth cell struts 1122Y, 1122Z of the fourth pair likewise can be coupled, and the distal end regions $1122_D$ of the growth cell struts 1122Y, 1122Z extending from the coupled proximal end regions $1122_P$. As shown in FIG. 3A, the distal end region $1122_D$ of the growth cell strut 1122W of the third pair can be disposed adjacent to the distal end region $1122_D$ of the growth cell strut 1122Y of the fourth pair; whereas, the distal end region $1122_D$ of the growth cell strut 1122X of the third pair can be disposed adjacent to the distal end region $1122_D$ of the growth cell strut 1122Z of the fourth pair. The third and fourth pairs of growth cell struts 1122W, 1122X, 1122Y, 1122Z thereby can define a second frame cell 1126WXYZ.

The distal end region $1122_D$ of the growth cell strut 1122W of the third pair can be coupled with the distal end region $1122_D$ of the growth cell strut 1122Y of the fourth pair, and/or the distal end region $1122_D$ of the growth cell strut 1122X of the third pair can be coupled with the distal end region $1122_D$ of the growth cell strut 1122Z of the fourth pair. In selected embodiments, the distal end region $1122_D$ of the growth cell strut 1122W can be separate from the distal end region 1122$_D$ of the growth cell strut 1122Y with the distal end regions 1122$_D$ as shown in FIG. 3A. The distal end region 1122$_D$ of the growth cell strut 1122X optionally can be separate from the distal end region 1122$_D$ of the growth cell strut 1122Z with the distal end regions 1122. Although the first, second, third and fourth pairs of growth cell struts 1122 are shown and described with reference to FIG. 3A as being coupled in similar manners for purposes of illustration only, the growth cell struts 1122 can be coupled in any suitable uniform and/or different manners.

The growth cell struts 1122 can be coupled in any suitable manner to form the ring configuration of the growth cell member 1120. The distal end regions 1122$_D$ of adjacent growth cell struts 1122, for example, can be coupled. As illustrated in FIG. 3A, the distal end region 1122$_D$ of the growth cell strut 1122T in the second pair of growth cell struts 1122S, 1122T and the distal end region 1122$_D$ of the growth cell strut 1122W in the third pair of growth cell struts 1122W, 1122X can be coupled. The distal end region 1122$_D$ of the growth cell strut 1122V in the second pair of growth cell struts 1122U, 1122V and the distal end region 1122$_D$ of the growth cell strut 1122Y in the fourth pair of growth cell struts 1122Y, 1122Z likewise can be coupled.

In selected embodiments, the coupled distal end regions 1122$_D$ of the growth cell struts 1122T, 1122W can be coupled with the coupled distal end regions 1122$_D$ of the growth cell struts 1122V, 1122Y as shown in FIG. 3A. The coupling between the coupled distal end regions 1122$_D$ of the growth cell struts 1122T, 1122W and the coupled distal end regions 1122$_P$ of the growth cell struts 1122V, 1122Y can be provided as a growth cell junction 1127. Stated somewhat differently, the coupled distal end regions 1122$_D$ of the growth cell struts 1122T, 1122W and the coupled distal end regions 1122$_D$ of the growth cell struts 1122V, 1122Y can intersect to form the growth cell junction 1127. The growth cell junction 1127 can provide a mechanical (or physical) connection between the growth cell struts 1122T, 1122W and the growth cell struts 1122V, 1122Y to form the growth cell member 1120. Preferably, the growth cell junction 1127 can provide a flexible coupling between the coupled distal end regions 1122$_P$ of the growth cell struts 1122T, 1122W and the coupled distal end regions 1122$_D$ of the growth cell struts 1122V, 1122Y.

To help provide the flexible coupling, the growth cell junction 1127 can be provided as a coupling member, such as a flexible coupling member 1129. The flexible coupling member 1129 can comprise a flexible central body 1129C with first and second coupling regions 1129A, 1129B. The first coupling region 1129A can be configured to couple with the coupled distal end regions 1122$_D$ of the growth cell struts 1122T, 1122W; whereas, the second coupling region 1164B can be configured to couple with the coupled distal end regions 1122$_D$ of the growth cell struts 1122V, 1122Y. Although the flexible central body 1129C can be provided with any suitable size, shape or other configuration, the flexible central body 1129C is shown in FIG. 3A as defining a central opening 1129D for enhancing the flexibility of the flexible coupling member 1129 and/or for providing a coupling region for an optional retention member 1200 (shown in FIGS. 2 and 5A-E).

Each pair of coupled distal end regions 1122$_D$ for the growth cell struts 1122 of the growth cell member 1120 can be coupled via a respective growth cell junction 1127. Alternatively, one or more pairs of the coupled distal end regions 1122$_D$ of the growth cell struts 1122 can be separate (or not coupled). The separated pairs of the coupled distal end regions 1122$_D$ of the growth cell struts 1122 can help enhance a flexibility of the growth cell member 1120 and, thereby, the device frame 1100.

Figure 3B:
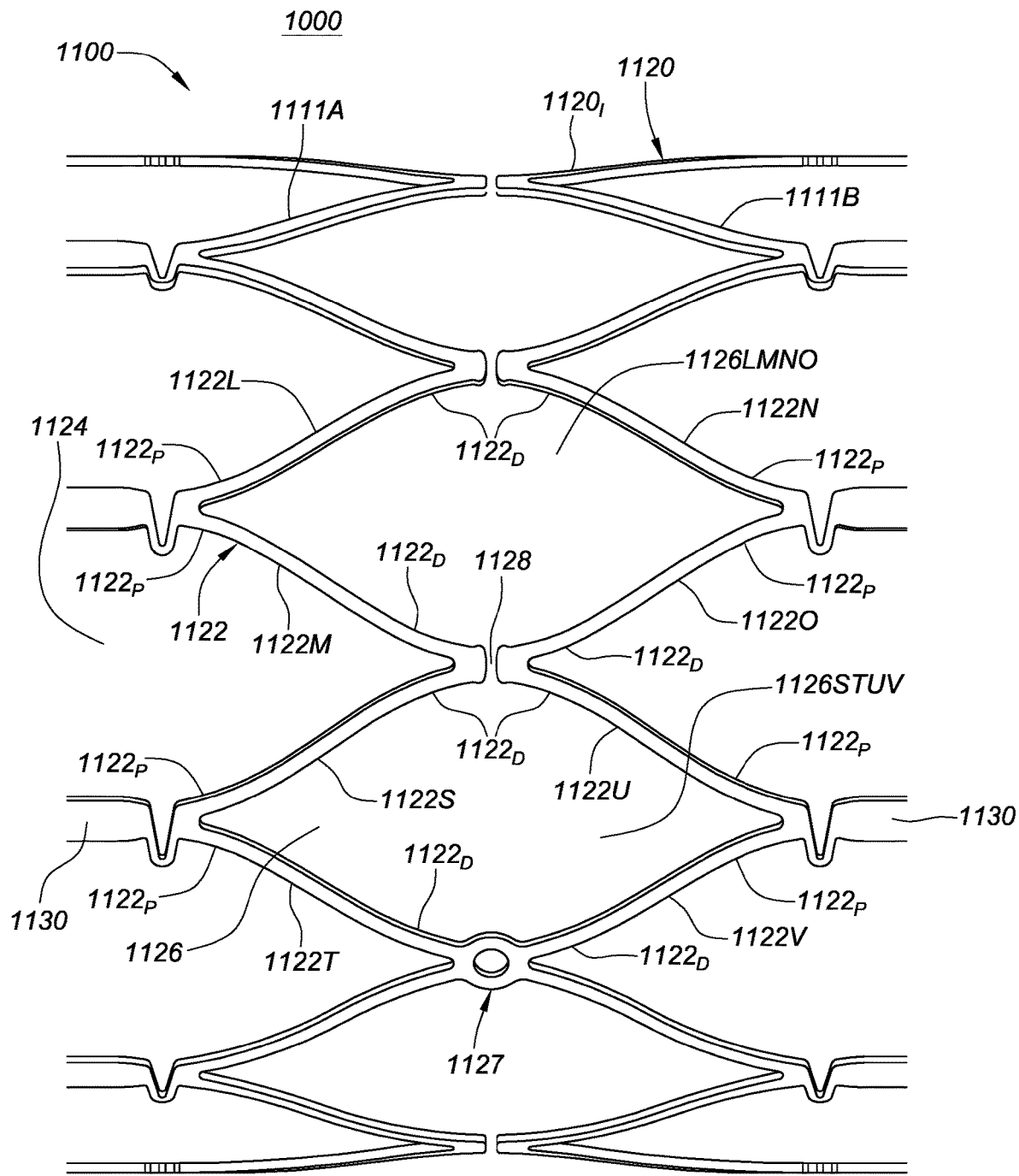
FIG. 3B is a detail drawing illustrating an exemplary alternative embodiment of the growth cell member of FIG. 3A, wherein the first pair of coupled growth cell struts of the growth cell member is separate from the second pair of coupled growth cell struts to define an intermediate gap.

Turning to FIG. 3B, for example, the growth cell member 1120 is shown as including a fifth pair of growth cell struts 1122L, 1122M and a sixth pair of growth cell struts 1122N, 1122O. The fifth pair of growth cell struts 1122L, 1122M and the sixth pair of growth cell struts 1122N, 1122O can be provided in the manner discussed in more detail above with reference to the first pair of growth cell struts 1122S, 1122T and the second pair of growth cell struts 1122U, 1122V of FIG. 3A and can be configured to define a third frame cell 1126LMNO. Coupled distal end regions 1122$_D$ of the growth cell struts 1122M, 1122S are shown as being separate from coupled distal end regions 1122$_D$ of the growth cell struts 1122O, 1122U. The coupled distal end regions 1122$_D$ of the growth cell struts 1122M, 1122S and the coupled distal end regions 1122$_D$ of the growth cell struts 1122O, 1122U can form a gap, such as an apical gap 1128, as illustrated in FIG. 3B. Stated somewhat differently, the growth cell member 1120 can comprise a plurality of apical gaps 1128 disposed between adjacent frame cells 1126.

The apical gaps 1128 advantageously can enable the device frame 1100, and thus the growth device 1000, to bend and/or deflect. A flexibility of the device frame 1100 can be increased by increasing a size of at least one of the apical gaps 1128 and/or can be decreased by decreasing the size of the apical gaps 1128. As shown in FIG. 3E, for example, the growth cell junctions 1127 and the apical gaps 1128 can permit the device frame 1100 to navigate curves and other geometries in the selected vessel or other lumen 120 of the patient 100.

In selected embodiments, the first pair of growth cell struts 1122S, 1122T, the third pair of growth cell struts 1122W, 1122X and the fifth pair of growth cell struts 1122L, 1122M of FIGS. 3A-B can be coupled to form a first annular strut arrangement 1111A of coupled growth cell struts 1122; whereas, the second pair of growth cell struts 1122U, 1122V, the fourth pair of growth cell struts 1122Y, 1122Z and the sixth pair of growth cell struts 1122N, 1122O of FIGS. 3A-B can be coupled to form a second annular strut arrangement 1111B of coupled growth cell struts 1122. The growth cell struts 1122 associated with the respective first and second annular strut arrangements 1111A, 1111B, in other words, can be coupled in a zigzag pattern to form a cylinder.

The proximal end regions 1122$_P$ of a pair of adjacent growth cell struts 1122 can be coupled and the distal end regions 1122$_D$ of the pair of adjacent growth cell struts 1122 can extend radially from the coupled proximal end regions 1122$_P$ to form a V shape, or half of a Z shape. Pairs of coupled growth cell struts 1122 forming the V shape can be repeated around a circumference of the cylinder with the distal end regions 1122$_D$ of the pairs of coupled growth cell struts 1122 being coupled to form a repeating pattern of V-shapes (or Z-shapes). The first and second annular strut arrangements 1111A, 1111B can be coupled via a growth cell junction 1127 and/or can cooperate to define the internal growth cell opening 1124 of the growth cell member 1120. As discussed above with reference to FIG. 3A, the growth cell junction 1127 can provide a coupling between the coupled distal end regions 1122$_D$ of the growth cell struts 1122T, 1122W and the coupled distal end regions 1122$_D$ of the growth cell struts 1122V, 1122Y. The growth cell junction 1127 thereby can provide a flexible coupling between the first and second strut annular arrangements 1111A, 1111B.

In the manner discussed in more detail above with reference to the device frame 1100 of FIG. 2, the growth cell member 1120 can be coupled with one or more spacing members 1130. The growth cell member 1120 and the spacing members 1130 can be coupled in any suitable manner. The spacing members 1130, for example, can be coupled with the proximal end regions 1122$_P$ of selected growth cell struts 1122 of the growth cell member 1120. As shown in FIG. 3A, the growth cell member 1120 can comprise an intermediate growth cell member 1120I with a first spacing member 1130 being coupled with the coupled proximal end regions 1122$_P$ of the first pair of growth cell struts 1122S, 1122T and the coupled proximal end regions 1122$_P$ of the third pair of growth cell struts 1122W, 1122X and a second spacing member 1130 being coupled with the coupled proximal end regions 1122$_P$ of the second pair of growth cell struts 1122U, 1122V and the coupled proximal end regions 1122$_P$ of the fourth pair of growth cell struts 1122Y, 1122Z.

Figure 3C:
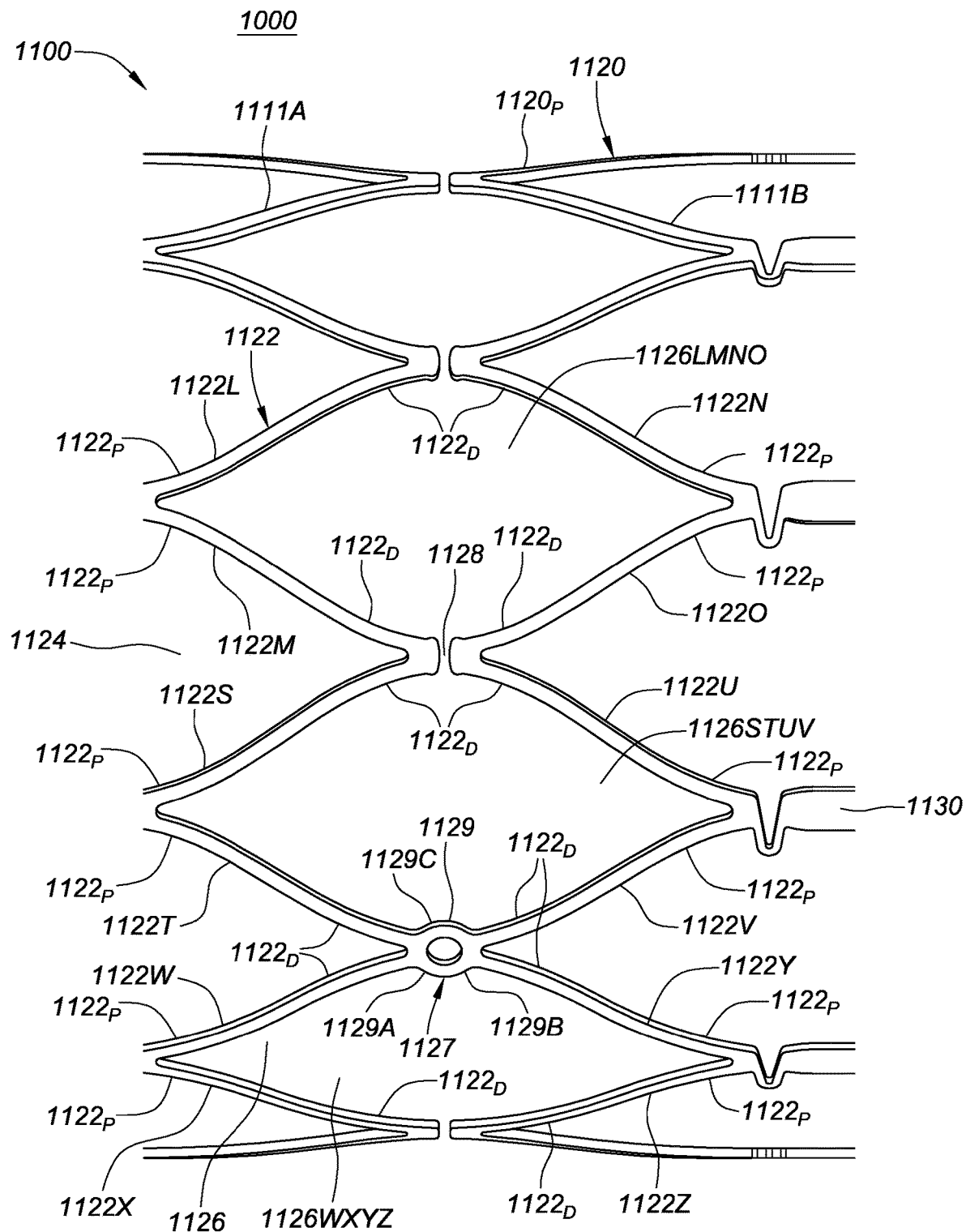
FIG. 3C is a detail drawing illustrating an exemplary embodiment of a proximal growth cell member for the growth device of FIG. 2.

The growth cell member 1120, in selected embodiments, can comprise a proximal growth cell member 1120$_P$ as illustrated in FIG. 3C. Turning to FIG. 3C, the proximal growth cell member 1120$_P$ of the device frame 1100 can comprise a plurality of growth cell struts 1122 defining one or more frame cells 1126 and being disposed in a ring configuration for defining an internal growth cell opening 1124 in the manner shown and described with reference to the growth cell member 1120 of FIG. 3A. Each of the growth cell struts 1122 of the proximal growth cell member 1120$_P$ optionally can be paired with another growth cell strut 1122 as shown in FIG. 3C.

In the manner discussed in more detail above with reference to FIG. 3A, the paired growth cell struts 1122 of the proximal growth cell member 1120$_P$ can include a first pair of growth cell struts 1122S, 1122T and a second pair of growth cell struts 1122U, 1122V. Each of the growth cell struts 1122S, 1122T, 1122U, 1122V can include a proximal end region 1122$_P$ and a distal end region 1122$_D$. With reference to the first pair of growth cell struts 1122S, 1122T, the proximal end region 1122$_P$ of the growth cell strut 1122S can be coupled with the proximal end region 1122$_P$ of the growth cell strut 1122T with the distal end regions 1122$_D$ of the growth cell struts 1122S, 1122T extending from the coupled proximal end regions 1122$_P$. The proximal end regions 1122$_P$ of the growth cell struts 1122U, 1122V of the second pair likewise can be coupled, and the distal end regions 1122$_D$ of the growth cell struts 1122U, 1122V can extend from the coupled proximal end regions 1122$_P$.

The distal end region 1122$_D$ of the growth cell strut 1122S of the first pair can be disposed adjacent to the distal end region 1122$_D$ of the growth cell strut 1122U of the second pair as illustrated in FIG. 3C. The distal end region 1122$_D$ of the growth cell strut 1122T of the first pair likewise can be disposed adjacent to the distal end region 1122$_D$ of the growth cell strut 1122V of the second pair. The first and second pairs of growth cell struts 1122S, 1122T, 1122U, 1122V thereby can define a first frame cell 1126STUV.

Optionally, the distal end region 1122$_D$ of the growth cell strut 1122S of the first pair can be coupled with the distal end region 1122$_D$ of the growth cell strut 1122U of the second pair; whereas, the distal end region 1122$_D$ of the growth cell strut 1122T of the first pair can be coupled with the distal end region 1122$_D$ of the growth cell strut 1122V of the second pair. The distal end region 1122$_D$ of the growth cell strut 1122S, in selected embodiments, can be separate from the distal end region 1122$_D$ of the growth cell strut 1122U with the distal end regions 1122$_D$ as shown in FIG. 3C. The distal end region 1122$_D$ of the growth cell strut 1122T optionally can be separate from the distal end region 1122$_D$ of the growth cell strut 1122V with the distal end regions 1122$_D$.

Additionally and/or alternatively, the paired growth cell struts 1122 can include a third pair of growth cell struts 1122W, 1122X and a fourth pair of growth cell struts 1122Y, 1122Z. Each of the growth cell struts 1122W, 1122X, 1122Y, 1122Z can include a proximal end region 1122$_P$ and a distal end region 1122. The proximal end region 1122$_P$ of the growth cell strut 1122W can be coupled with the proximal end region 1122$_P$ of the growth cell strut 1122X with the distal end regions 1122$_D$ of the growth cell struts 1122W, 1122X extending from the coupled proximal end regions 1122$_P$. The proximal end regions 1122$_P$ of the growth cell struts 1122Y, 1122Z of the fourth pair likewise can be coupled, and the distal end regions 1122$_D$ of the growth cell struts 1122Y, 1122Z extending from the coupled proximal end regions 1122$_P$. As shown in FIG. 3C, the distal end region 1122$_D$ of the growth cell strut 1122W of the third pair can be disposed adjacent to the distal end region 1122$_D$ of the growth cell strut 1122Y of the fourth pair; whereas, the distal end region 1122$_D$ of the growth cell strut 1122X of the third pair can be disposed adjacent to the distal end region 1122$_D$ of the growth cell strut 1122Z of the fourth pair. The third and fourth pairs of growth cell struts 1122W, 1122X, 1122Y, 1122Z thereby can define a second frame cell 1126WXYZ.

The distal end region 1122$_D$ of the growth cell strut 1122W of the third pair can be coupled with the distal end region 1122$_D$ of the growth cell strut 1122Y of the fourth pair, and/or the distal end region 1122$_D$ of the growth cell strut 1122X of the third pair can be coupled with the distal end region 1122$_D$ of the growth cell strut 1122Z of the fourth pair. In selected embodiments, the distal end region 1122$_D$ of the growth cell strut 1122W can be separate from the distal end region 1122$_D$ of the growth cell strut 1122Y with the distal end regions 1122$_D$ as shown in FIG. 3C. The distal end region 1122$_D$ of the growth cell strut 1122X optionally can be separate from the distal end region 1122$_D$ of the growth cell strut 1122Z with the distal end regions 1122. Although the first, second, third and fourth pairs of growth cell struts 1122 are shown and described with reference to FIG. 3C as being coupled in similar manners for purposes of illustration only, the growth cell struts 1122 can be coupled in any suitable uniform and/or different manners.

The growth cell struts 1122 can be coupled in any suitable manner to form the ring configuration of the proximal growth cell member 1120$_P$. The distal end regions 1122$_D$ of adjacent growth cell struts 1122, for example, can be coupled. As illustrated in FIG. 3C, the distal end region 1122$_D$ of the growth cell strut 1122T in the second pair of growth cell struts 1122S, 1122T and the distal end region 1122$_D$ of the growth cell strut 1122W in the third pair of growth cell struts 1122W, 1122X can be coupled. The distal end region 1122$_D$ of the growth cell strut 1122V in the second pair of growth cell struts 1122U, 1122V and the distal end region 1122$_D$ of the growth cell strut 1122Y in the fourth pair of growth cell struts 1122Y, 1122Z likewise can be coupled.

In selected embodiments, the coupled distal end regions 1122$_D$ of the growth cell struts 1122T, 1122W can be coupled with the coupled distal end regions 1122$_D$ of the growth cell struts 1122V, 1122Y. The coupling between the coupled distal end regions 1122$_D$ of the growth cell struts 1122T, 1122W and the coupled distal end regions 1122$_D$ of the growth cell struts 1122V, 1122Y can be provided as a growth cell junction 1127 in the manner shown and described in more detail above with reference to FIG. 3A. In other words, the coupled distal end regions $1122_D$ of the growth cell struts 1122T, 1122W and the coupled distal end regions $1122_D$ of the growth cell struts 1122V, 1122Y can intersect to form the growth cell junction 1127. The growth cell junction 1127 can provide a mechanical (or physical) connection between the growth cell struts 1122T, 1122W and the growth cell struts 1122V, 1122Y to form the growth cell member 1120. Preferably, the growth cell junction 1127 provides a flexible coupling between the coupled distal end regions $1122_D$ of the growth cell struts 1122T, 1122W and the coupled distal end regions $1122_D$ of the growth cell struts 1122V, 1122Y.

To help provide the flexible coupling, the growth cell junction 1127 can be provided as a coupling member, such as a flexible coupling member 1129. The flexible coupling member 1129 can comprise a flexible central body 1129C with first and second coupling regions 1129A, 1129B. The first coupling region 1129A can be configured to couple with the coupled distal end regions $1122_D$ of the growth cell struts 1122T, 1122W; whereas, the second coupling region 1164B can be configured to couple with the coupled distal end regions $1122_D$ of the growth cell struts 1122V, 1122Y. Although the flexible central body 1129C can be provided with any suitable size, shape or other configuration, the flexible central body 1129C is shown in FIG. 3C as defining a central opening 1129D for enhancing the flexibility of the flexible coupling member 1129 and/or for providing a coupling region for an optional retention member 1200 (shown in FIGS. 2 and 5A-E).

Each pair of coupled distal end regions $1122_D$ for the growth cell struts 1122 of the growth cell member 1120 can be coupled via a respective growth cell junction 1127. Alternatively, one or more pairs of the coupled distal end regions $1122_D$ of the growth cell struts 1122 can be separate (or not coupled). The separated pairs of the coupled distal end regions $1122_D$ of the growth cell struts 1122 can help enhance a flexibility of the growth cell member 1120 and, thereby, the device frame 1100.

The growth cell member 1120, for example, can include a fifth pair of growth cell struts 1122L, 1122M and a sixth pair of growth cell struts 1122N, 1122O. The fifth pair of growth cell struts 1122L, 1122M and the sixth pair of growth cell struts 1122N, 1122O can be provided in the manner discussed in more detail above with reference to the fifth pair of growth cell struts 1122L, 1122M and the sixth pair of growth cell struts 1122N, 1122O of FIG. 3B and can be configured to define a third frame cell 1126LMNO. Coupled distal end regions $1122_D$ of the growth cell struts 1122M, 1122S are shown as being separate from coupled distal end regions $1122_D$ of the growth cell struts 1122O, 1122U. The coupled distal end regions $1122_D$ of the growth cell struts 1122M, 1122S and the coupled distal end regions $1122_D$ of the growth cell struts 1122O, 1122U can form a gap, such as an apical gap 1128, in the manner shown and described in more detail above with reference to FIG. 3B. In other words, the growth cell member 1120 can comprise a plurality of apical gaps 1128 disposed between adjacent frame cells 1126. The apical gaps 1128 advantageously can enable the device frame 1100, and thus the growth device 1000, to bend and/or deflect. A flexibility of the device frame 1100 can be increased by increasing a size of at least one of the apical gaps 1128 and/or can be decreased by decreasing the size of the apical gaps 1128.

In selected embodiments, the first pair of growth cell struts 1122S, 1122T, the third pair of growth cell struts 1122W, 1122X and the fifth pair of growth cell struts 1122L, 1122M can be coupled to form a first annular strut arrangement 1111A of coupled growth cell struts 1122; whereas, the second pair of growth cell struts 1122U, 1122V, the fourth pair of growth cell struts 1122Y, 1122Z and the sixth pair of growth cell struts 1122N, 1122O can be coupled to form a second annular strut arrangement 1111B of coupled growth cell struts 1122. The first and second annular strut arrangements 1111A, 1111B can be coupled via a growth cell junction 1127 and/or can cooperate to define the internal growth cell opening 1124 of the growth cell member 1120. The growth cell junction 1127 can provide a coupling between the coupled distal end regions $1122_D$ of the growth cell struts 1122T, 1122W and the coupled distal end regions $1122_D$ of the growth cell struts 1122V, 1122Y. The growth cell junction 1127 thereby can provide a flexible coupling between the first and second strut annular arrangements 1111A, 1111B.

In the manner discussed in more detail above with reference to the device frame 1100 of FIG. 2, the proximal growth cell member $1120_P$ can be coupled with a spacing member 1130. The proximal growth cell member $1120_P$ and the spacing member 1130 can be coupled in any suitable manner. The spacing member 1130, for example, can be coupled with the proximal end regions $1122_P$ of selected growth cell struts 1122 of the proximal growth cell member $1120_P$. As shown in FIG. 3C, the spacing member 1130 can be coupled with the coupled with the coupled proximal end regions $1122_P$ of the second pair of growth cell struts 1122U, 1122V and the coupled proximal end regions $1122_P$ of the fourth pair of growth cell struts 1122Y, 1122Z.

Figure 3D:
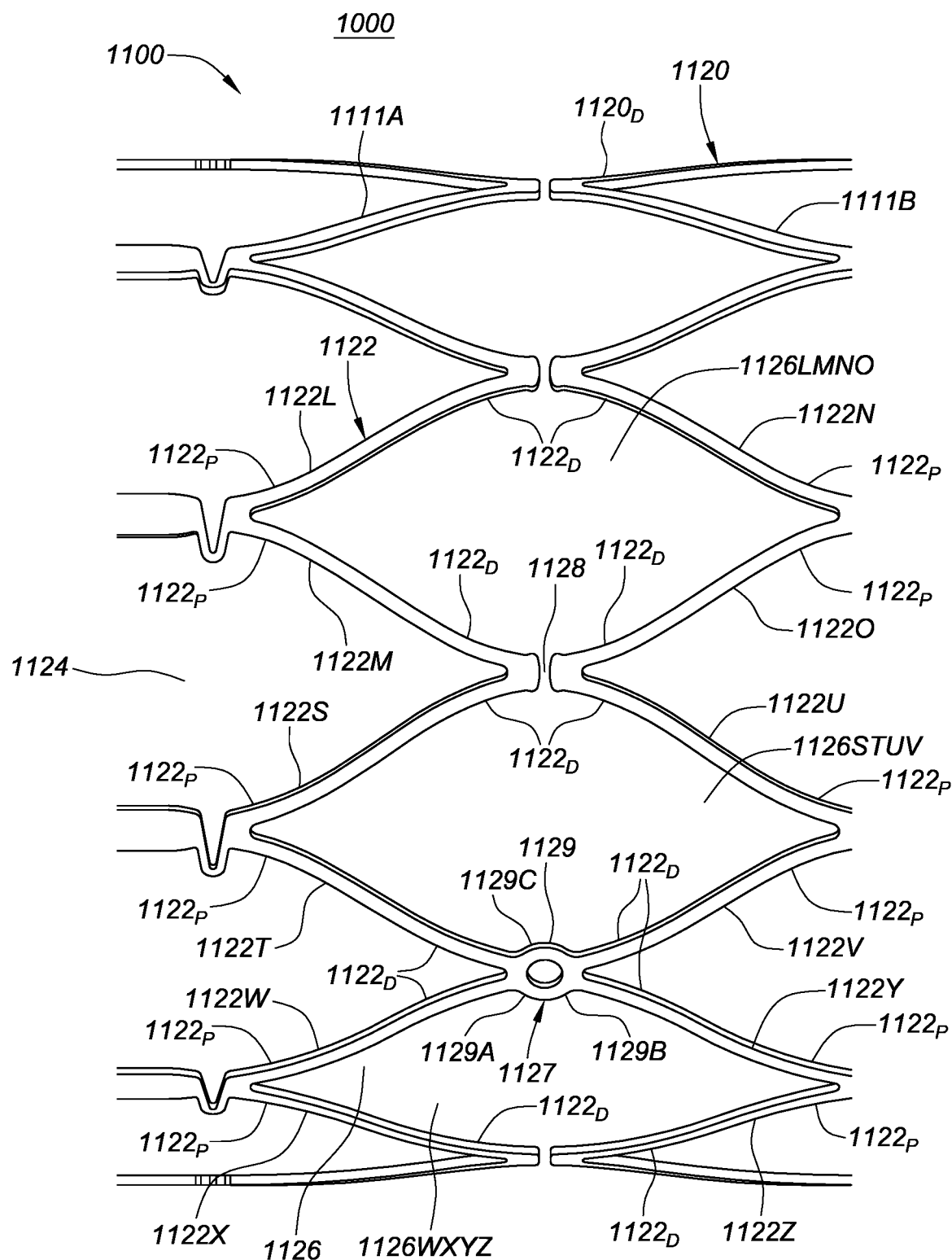
FIG. 3D is a detail drawing illustrating an exemplary embodiment of a distal growth cell member for the growth device of FIG. 2.
Figure 3E:
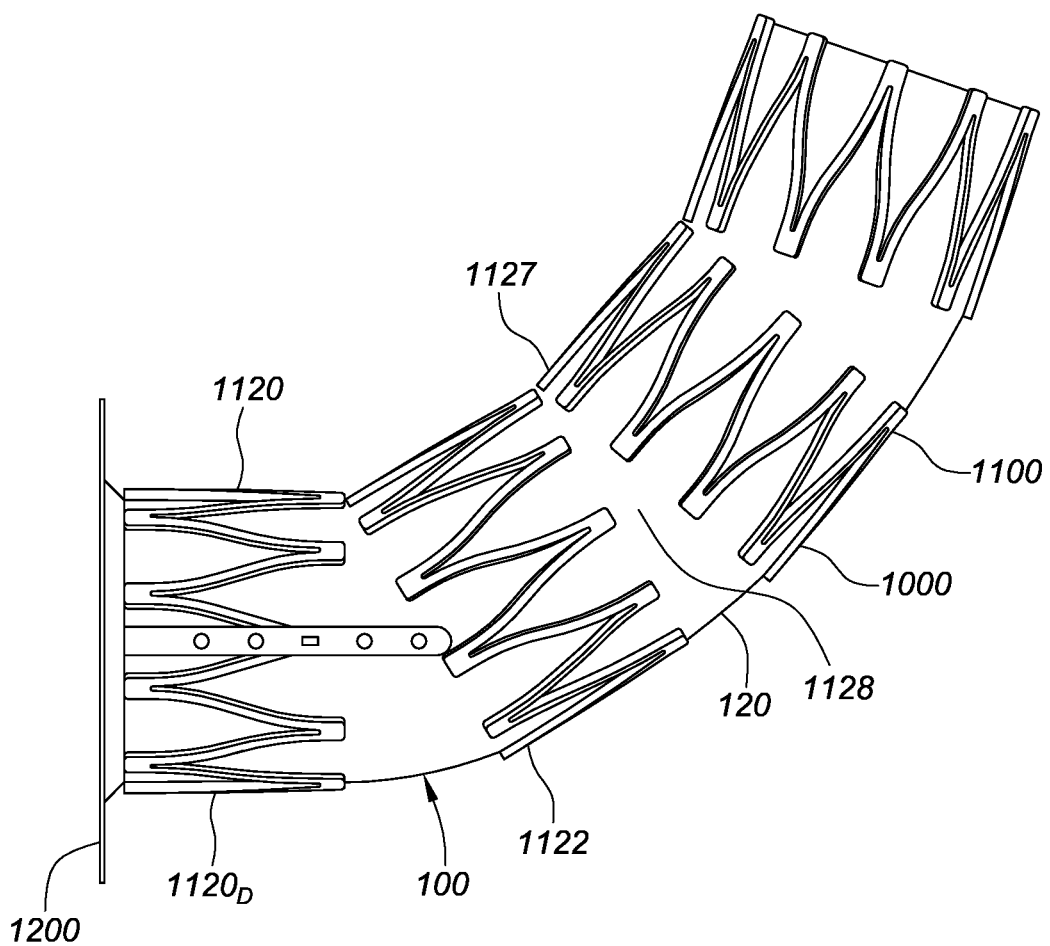
FIG. 3E is a detail drawing illustrating an exemplary alternative embodiment of the growth device of FIG. 2, wherein the coupled pairs of coupled growth cell struts enable the growth device to navigate internal anatomy of a patient.

Additionally and/or alternatively, the growth cell member 1120 can comprise a distal growth cell member $1120_D$ as illustrated in FIG. 3D. Turning to FIG. 3D, the distal growth cell member $1120_D$ of the device frame 1100 can comprise a plurality of growth cell struts 1122 defining one or more frame cells 1126 and being disposed in a ring configuration for defining an internal growth cell opening 1124 in the manner shown and described with reference to the growth cell member 1120 of FIG. 3A. Each of the growth cell struts 1122 of the distal growth cell member $1120_D$ optionally can be paired with another growth cell strut 1122 as shown in FIG. 3D.

In the manner discussed in more detail above with reference to FIG. 3A, the paired growth cell struts 1122 of the distal growth cell member $1120_D$ can include a first pair of growth cell struts 1122S, 1122T and a second pair of growth cell struts 1122U, 1122V. Each of the growth cell struts 1122S, 1122T, 1122U, 1122V can include a proximal end region $1122_P$ and a distal end region $1122_D$. With reference to the first pair of growth cell struts 1122S, 1122T, the proximal end region $1122_P$ of the growth cell strut 1122S can be coupled with the proximal end region $1122_P$ of the growth cell strut 1122T with the distal end regions $1122_D$ of the growth cell struts 1122S, 1122T extending from the coupled proximal end regions $1122_P$. The proximal end regions $1122_P$ of the growth cell struts 1122U, 1122V of the second pair likewise can be coupled, and the distal end regions $1122_D$ of the growth cell struts 1122U, 1122V can extend from the coupled proximal end regions $1122_P$.

As illustrated in FIG. 3D, the distal end region $1122_D$ of the growth cell strut 1122S of the first pair can be disposed adjacent to the distal end region $1122_D$ of the growth cell strut 1122U of the second pair; whereas, the distal end region $1122_D$ of the growth cell strut 1122T of the first pair can be disposed adjacent to the distal end region $1122_D$ of the growth cell strut 1122V of the second pair. The first and second pairs of growth cell struts 1122S, 1122T, 1122U, 1122V thereby can define a first frame cell 1126STUV.

The distal end region $1122_D$ of the growth cell strut 1122S of the first pair optionally can be coupled with the distal end region $1122_D$ of the growth cell strut 1122U of the second pair, and/or the distal end region $1122_D$ of the growth cell strut 1122T of the first pair optionally can be coupled with the distal end region $1122_D$ of the growth cell strut 1122V of the second pair. In selected embodiments, the distal end region $1122_D$ of the growth cell strut 1122S can be separate from the distal end region $1122_D$ of the growth cell strut 1122U with the distal end regions $1122_D$ as shown in FIG. 3D. The distal end region $1122_D$ of the growth cell strut 1122T optionally can be separate from the distal end region $1122_D$ of the growth cell strut 1122V with the distal end regions $1122_D$.

Additionally and/or alternatively, the paired growth cell struts 1122 can include a third pair of growth cell struts 1122W, 1122X and a fourth pair of growth cell struts 1122Y, 1122Z. Each of the growth cell struts 1122W, 1122X, 1122Y, 1122Z can include a proximal end region $1122_P$ and a distal end region 1122. The proximal end region $1122_P$ of the growth cell strut 1122W can be coupled with the proximal end region $1122_P$ of the growth cell strut 1122X with the distal end regions $1122_D$ of the growth cell struts 1122W, 1122X extending from the coupled proximal end regions $1122_P$. The proximal end regions $1122_P$ of the growth cell struts 1122Y, 1122Z of the fourth pair likewise can be coupled, and the distal end regions $1122_D$ of the growth cell struts 1122Y, 1122Z extending from the coupled proximal end regions $1122_P$. As shown in FIG. 3D, the distal end region $1122_D$ of the growth cell strut 1122W of the third pair can be disposed adjacent to the distal end region $1122_D$ of the growth cell strut 1122Y of the fourth pair; whereas, the distal end region $1122_D$ of the growth cell strut 1122X of the third pair can be disposed adjacent to the distal end region $1122_D$ of the growth cell strut 1122Z of the fourth pair. The third and fourth pairs of growth cell struts 1122W, 1122X, 1122Y, 1122Z thereby can define a second frame cell 1126WXYZ.

The distal end region $1122_D$ of the growth cell strut 1122W of the third pair can be coupled with the distal end region $1122_D$ of the growth cell strut 1122Y of the fourth pair, and/or the distal end region $1122_D$ of the growth cell strut 1122X of the third pair can be coupled with the distal end region $1122_D$ of the growth cell strut 1122Z of the fourth pair. In selected embodiments, the distal end region $1122_D$ of the growth cell strut 1122W can be separate from the distal end region $1122_D$ of the growth cell strut 1122Y with the distal end regions $1122_D$ as shown in FIG. 3D. The distal end region $1122_D$ of the growth cell strut 1122X optionally can be separate from the distal end region $1122_D$ of the growth cell strut 1122Z with the distal end regions 1122. Although the first, second, third and fourth pairs of growth cell struts 1122 are shown and described with reference to FIG. 3D as being coupled in similar manners for purposes of illustration only, the growth cell struts 1122 can be coupled in any suitable uniform and/or different manners.

The growth cell struts 1122 can be coupled in any suitable manner to form the ring configuration of the distal growth cell member 1120. The distal end regions $1122_D$ of adjacent growth cell struts 1122, for example, can be coupled. As illustrated in FIG. 3D, the distal end region $1122_D$ of the growth cell strut 1122T in the second pair of growth cell struts 1122S, 1122T and the distal end region $1122_D$ of the growth cell strut 1122W in the third pair of growth cell struts 1122W, 1122X can be coupled. The distal end region $1122_D$ of the growth cell strut 1122V in the second pair of growth cell struts 1122U, 1122V and the distal end region $1122_D$ of the growth cell strut 1122Y in the fourth pair of growth cell struts 1122Y, 1122Z likewise can be coupled.

In selected embodiments, the coupled distal end regions $1122_D$ of the growth cell struts 1122T, 1122W can be coupled with the coupled distal end regions $1122_D$ of the growth cell struts 1122V, 1122Y. The coupling between the coupled distal end regions $1122_D$ of the growth cell struts 1122T, 1122W and the coupled distal end regions $1122_D$ of the growth cell struts 1122V, 1122Y can be provided as a growth cell junction 1127 in the manner shown and described in more detail above with reference to FIG. 3A. In other words, the coupled distal end regions $1122_D$ of the growth cell struts 1122T, 1122W and the coupled distal end regions $1122_D$ of the growth cell struts 1122V, 1122Y can intersect to form the growth cell junction 1127. The growth cell junction 1127 can provide a mechanical (or physical) connection between the growth cell struts 1122T, 1122W and the growth cell struts 1122V, 1122Y to form the growth cell member 1120. Preferably, the growth cell junction 1127 provides a flexible coupling between the coupled distal end regions $1122_D$ of the growth cell struts 1122T, 1122W and the coupled distal end regions $1122_D$ of the growth cell struts 1122V, 1122Y.

To help provide the flexible coupling, the growth cell junction 1127 can be provided as a coupling member, such as a flexible coupling member 1129. The flexible coupling member 1129 can comprise a flexible central body 1129C with first and second coupling regions 1129A, 1129B. The first coupling region 1129A can be configured to couple with the coupled distal end regions $1122_D$ of the growth cell struts 1122T, 1122W; whereas, the second coupling region 1164B can be configured to couple with the coupled distal end regions $1122_D$ of the growth cell struts 1122V, 1122Y. Although the flexible central body 1129C can be provided with any suitable size, shape or other configuration, the flexible central body 1129C is shown in FIG. 3D as defining a central opening 1129D for enhancing the flexibility of the flexible coupling member 1129 and/or for providing a coupling region for an optional retention member 1200 (shown in FIGS. 2 and 5A-E).

Each pair of coupled distal end regions $1122_D$ for the growth cell struts 1122 of the growth cell member 1120 can be coupled via a respective growth cell junction 1127. Alternatively, one or more pairs of the coupled distal end regions $1122_D$ of the growth cell struts 1122 can be separate (or not coupled). The separated pairs of the coupled distal end regions $1122_D$ of the growth cell struts 1122 can help enhance a flexibility of the growth cell member 1120 and, thereby, the device frame 1100.

The growth cell member 1120, for example, can include a fifth pair of growth cell struts 1122L, 1122M and a sixth pair of growth cell struts 1122N, 1122O. The fifth pair of growth cell struts 1122L, 1122M and the sixth pair of growth cell struts 1122N, 1122O can be provided in the manner discussed in more detail above with reference to the fifth pair of growth cell struts 1122L, 1122M and the sixth pair of growth cell struts 1122N, 1122O of FIG. 3B and can be configured to define a third frame cell 1126LMNO. Coupled distal end regions $1122_D$ of the growth cell struts 1122M, 1122S are shown as being separate from coupled distal end regions $1122_D$ of the growth cell struts 1122O, 1122U. The coupled distal end regions $1122_D$ of the growth cell struts 1122M, 1122S and the coupled distal end regions $1122_D$ of the growth cell struts 1122O, 1122U can form a gap, such as an apical gap 1128, in the manner shown and described in more detail above with reference to FIG. 3B. Stated somewhat differently, the growth cell member 1120 can comprise a plurality of apical gaps 1128 disposed between adjacent frame cells 1126. The apical gaps 1128 advantageously can enable the device frame 1100, and thus the growth device 1000, to bend and/or deflect. A flexibility of the device frame 1100 can be increased by increasing a size of at least one of the apical gaps 1128 and/or can be decreased by decreasing the size of the apical gaps 1128.

In selected embodiments, the first pair of growth cell struts 1122S, 1122T, the third pair of growth cell struts 1122W, 1122X and the fifth pair of growth cell struts 1122L, 1122M can be coupled to form a first annular strut arrangement 1111A of coupled growth cell struts 1122; whereas, the second pair of growth cell struts 1122U, 1122V, the fourth pair of growth cell struts 1122Y, 1122Z and the sixth pair of growth cell struts 1122N, 1122O can be coupled to form a second annular strut arrangement 1111B of coupled growth cell struts 1122. The first and second annular strut arrangements 1111A, 1111B can be coupled via a growth cell junction 1127 and/or can cooperate to define the internal growth cell opening 1124 of the growth cell member 1120. The growth cell junction 1127 can provide a coupling between the coupled distal end regions $1122_D$ of the growth cell struts 1122T, 1122W and the coupled distal end regions $1122_D$ of the growth cell struts 1122V, 1122Y. The growth cell junction 1127 thereby can provide a flexible coupling between the first and second strut annular arrangements 1111A, 1111B.

In the manner discussed in more detail above with reference to the device frame 1100 of FIG. 2, the distal growth cell member $1120_D$ can be coupled with a spacing member 1130. The distal growth cell member $1120_D$ and the spacing member 1130 can be coupled in any suitable manner. The spacing member 1130, for example, can be coupled with the proximal end regions $1122_P$ of selected growth cell struts 1122 of the distal growth cell member 1120. As shown in FIG. 3D, the spacing member 1130 can be coupled with the coupled with the coupled proximal end regions $1122_P$ of the first pair of growth cell struts 1122S, 1122T and the coupled proximal end regions $1122_P$ of the third pair of growth cell struts 1122W, 1122X.

Figure 4:
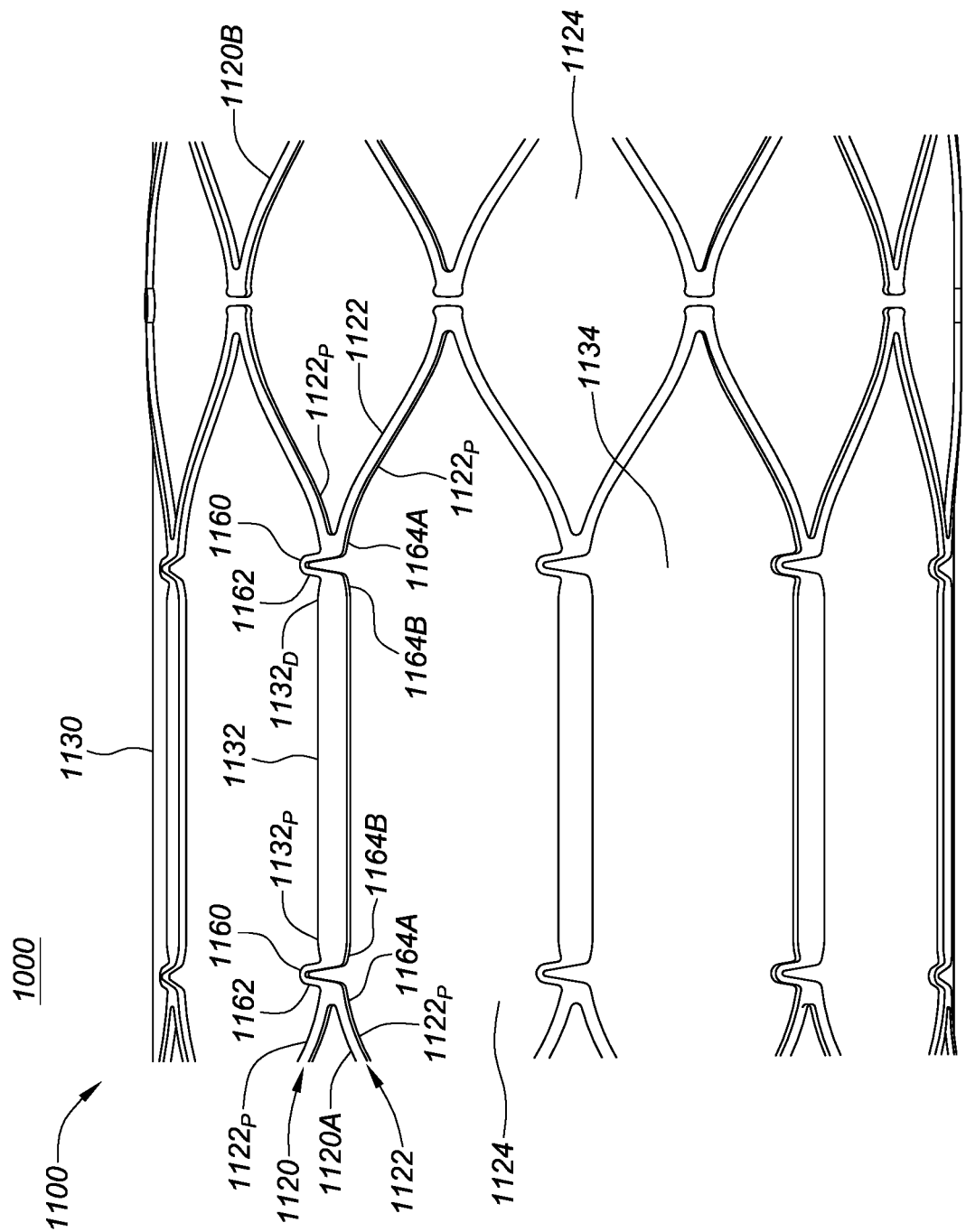
FIG. 4 is a detail drawing illustrating an exemplary embodiment of a spacing member for the growth device of FIG. 2.

The spacing member(s) 1130 of the device frame 1100 can have uniform structures and/or different structures. In selected embodiments, the spacing member(s) 1130 can be formed from metal, metal alloys, polymer, biodegradable polymers, cloth, and/or a combination of multiple materials, without limitation. An exemplary spacing member 1130 is illustrated in FIG. 4. Turning to FIG. 4, the spacing member 1130 is shown as comprising a plurality of spacer member struts 1132 that can be disposed in a ring configuration for defining an internal spacer member opening 1134 of the spacing member 1130. Each spacer member strut 1132 of the spacing member 1130 can comprise an elongated member with a proximal end region $1132_P$ and a distal end region 1132. The spacer member struts 1132 can have predetermined spacer member strut widths, predetermined spacer member strut thicknesses and/or predetermined spacer member strut lengths. The predetermined spacer member strut widths, predetermined spacer member strut thicknesses and/or predetermined spacer member strut lengths of the spacer member struts 1132 can comprise any suitable spacer member strut widths, spacer member strut thicknesses and/or spacer member strut lengths. Exemplary spacer member strut thicknesses can include, but are not limited to, 0.15 millimeters to 0.75 millimeters; whereas, the spacer member strut lengths can range between five millimeters and fifty millimeters or more, without limitation. In selected embodiments, the spacing member 1130 can comprise cobalt chromium for providing radial strength to the spacing member 1130 itself.

To increase a radial strength of the spacer member struts 1132, the spacer member struts 1132 preferably have spacer member strut widths that are between one and three times the predetermined cell strut widths of growth cell struts 1122 and/or have spacer member strut thicknesses that are between one and three times the predetermined cell strut thicknesses of the growth cell struts 1122. Although shown and described as comprising uniform spacer member strut widths and/or uniform spacer member strut thicknesses with reference to FIG. 4 for purposes of illustration only, the spacer member struts 1132 can include spacer member strut widths and/or spacer member strut thicknesses that are uniform and/or different.

As illustrated in FIG. 4, the spacer member struts 1132 can be axially aligned with the device frame 1100 and/or can be disposed in a substantially parallel configuration. The geometrical configuration of the spacer member struts 1132 advantageously can enable the spacing members 1130 to expand as the growth cell members 1120 expand but without experiencing any foreshortening. Foreshortening of the growth device 1000 thereby can be reduced or eliminated during expansion via the spacer member struts 1132 of the spacing members 1130. Stated somewhat differently, the spacer member struts 1132 of the spacing members 1130 can reduce or eliminating a percentage foreshortening of the growth device 1000 throughout an operating range of diameters, cross-sections or other dimensions of the growth device 1000 from implantation through expansion.

Increasing the spacer member strut lengths of the spacer member struts 1132 can increase a resistance of the growth device 1000 to percentage foreshortening over an overall length of the growth device 1000 but can reduce an overall radial strength of the growth device 1000. In contrast, spacer member struts 1132 with decreased spacer member strut lengths can decrease the resistance of the growth device 1000 to percentage foreshortening over the overall length of the growth device 1000 and can increase the overall radial strength of the growth device 1000. The spacer member strut lengths of the spacer member struts 1132 can be uniform and/or different among the spacing members 1130 of the growth device 1000. In other words, the spacer member strut lengths for a first spacing member 1130 of the growth device 1000 can be greater than the spacer member strut lengths for a second spacing member 1130 of the growth device 1000 and/or can be less than the spacer member strut lengths for a third spacing member 1130 of the growth device 1000. The spacer member strut lengths for the spacing members 1130, for example, can depend upon a predetermined application of the growth device 1000, an implant location of the growth device 1000 within a patient 100 (shown in FIG. 8) and/or an anatomy of the patient 100.

The spacing member 1130 can be configured to couple with a first growth cell member 1120A and/or a second growth cell member 1120B in any suitable manner. The proximal end regions $1132_P$ of the spacer member struts 1132, for example, can be configured to couple with the first growth cell member 1120A and/or the distal end regions $1132_D$ of the spacer member struts 1132 can be configured to couple with the second growth cell member 1120B. In selected embodiments, the proximal end regions $1132_P$ of the spacer member struts 1132 can be configured to couple with the distal end regions $1122_D$ of the growth cell struts 1122 associated with the first growth cell member 1120A; whereas, the distal end regions $1132_D$ of the spacer member struts 1132 can be configured to couple with the proximal end regions 1122$_P$ of the growth cell struts 1122 associated with the second growth cell member 1120B as illustrated in FIG. 4.

If the device frame 1100 comprises a series of alternating growth cell members 1120 and spacing members 1130 that span axially between the proximal and distal end regions 1110$_P$, 1110$_D$ of the device frame 1100 in the manner set forth above with reference to FIG. 2, the internal growth cell openings 1124 of the growth cell members 1120 and the internal spacer member opening(s) 1134 of the spacing member(s) 1130 can cooperate to define the central axial channel 1150 of the elongated device frame 1100. The internal growth cell openings 1124 of the growth cell members 1120 and the internal spacer member opening(s) 1134 of the spacing member(s) 1130, in other words, can be axially aligned to provide the central axial channel 1150 of the elongated device frame 1100.

In selected embodiments, each spacing member 1130 can couple directly with the associated growth cell members 1120. Additionally and/or alternatively, one or more of the spacing members 1130 and the associated growth cell members 1120 can couple indirectly via one or more optional intermediate coupling members, such as exemplary intermediate coupling members 1160 as illustrated in FIG. 4. Each intermediate coupling member 1160 can comprise a flexible central body 1162 with first and second coupling regions 1164A, 1164B. A thickness of the flexible central body 1162 can be increased to decrease a flexibility of the intermediate coupling member 1160 and/or can be decreased to increase the flexibility of the intermediate coupling member 1160. As shown in FIG. 4, the flexible central body 1162 can be provided with a forked shape, or a V-shape, with two branches (or end regions) at which the first and second coupling regions 1164A, 1164B are disposed. The first coupling region 1164A can be configured to couple with a relevant growth cell member 1120; whereas, the second coupling region 1164B can be configured to couple with a relevant spacing member 1130.

The flexible central body 1162 advantageously can permit a flexible coupling between the relevant growth cell member 1120 and the relevant spacing member 1130. If the device frame 1100 comprises a series of alternating growth cell members 1120 and spacing members 1130 that span axially between the proximal and distal end regions 1110$_P$, 1110$_D$ of the device frame 1100 in the manner set forth above with reference to FIG. 2, the flexible couplings between the growth cell members 1120 and the spacing members 1130, in turn, can increase an overall flexibility of the device frame 1100. The flexibility of the device frame 1100 can facilitate implantation, deployment and/or expansion of the growth device 1000 within a patient 100 (shown in FIG. 8) during use.

For some embodiments, the device frame 1100 can take any of various forms with respect to strut design. The device frame 1100 may be designed in a diamond strut configuration to allow for adequate crimp size, radial force, and targeted diameter range. This diamond strut configuration may be a closed cell design with attached vertices at each level of diamond rows that intersect to form respective strut junctions. Other embodiments may be an open cell design without diamond strut configurations. An open-cell design consists of cells that are disconnected from one another, enabling flexibility in the frame. Another configuration of the device frame 1100 may take a chevron strut design, which is categorized by a straight connecting beam between the apexes of the struts. The chevron strut design advantageously can limit foreshortening of the struts as the implant is expanded to higher (or larger) diameters. Embodiments of this frame may consist of a plurality of frame struts extending continuously from the proximal side of the frame to a distal side of the frame. The expanded device frame 1100 can form the central axial channel 1150 for blood flow.

Returning to FIG. 2, the growth device 1000 is shown as including one or more optional retention members 1200. The retention members 1200 can be disposed at the proximal end region 1110$_P$ and/or the distal end region 1110$_D$ of the device frame 1100 and can extend radially from the periphery 1140. Stated somewhat differently, the retention members 1200 can be coupled with the proximal growth cell member 1120$_P$ and/or the distal growth cell member 1120$_D$ of the device frame 1100 and extend radially therefrom. In selected embodiments, the retention members 1200 can be distributed around the periphery 1140 of the device frame 1100. The retention members 1200 can be distributed around the periphery 1140 of the device frame 1100 in any predetermined configuration and, as shown in FIG. 2, can be evenly distributed around the periphery 1140.

The retention members 1200 allow for positioning support when delivered via a delivery catheter system 2000 (shown in FIGS. 14A-D) and retention of the growth device 1000 when connecting bloodstreams of different vessels. The growth device 1000, for example, can be configured for deployment in the selected vessel or other lumen 120 (shown in FIG. 8) of the patient 100 (shown in FIG. 8). Each retention member 1200 can be provided in any suitable manner. The retention member 1200, for example, can be made from a polymer, a metal or other appropriate material. The retention member 1200 may comprise paddles, hooks, tabs, spirals, or other suitable shapes. In selected embodiments, the device frame 1100 may be flared radially outwardly to form one or more of the retention members 1200. This flaring may occur by utilizing a balloon expansion system 2200 (shown in FIG. 14B) of the delivery catheter system 2000 if the device frame 1100 is made of balloon-expandable materials such as stainless steel or cobalt chromium. Additionally and/or alternatively, the retention members 1200 can be shape-set into self-expanding materials like nitinol. In some embodiments, self-expanding retention members 1200 may be attached to balloon-expandable shunts. This enables catheter delivery as the self-expanding retention members 1200 can take shape in a perpendicular fashion to the delivery catheter system 2000 and crimped shunt, allowing for retention during deployment and after inflation of the device frame 1100.

The retention members 1200 may be angled towards a proximal end region of the device frame 1100 and/or towards a distal end region of the device frame 1100 depending on retention or sealing features needed. In some embodiments, the retention members 1200 can comprise single bars, loops, or other shapes. One or more retention members 1200 can be disposed around the periphery 1140 of the device frame 1100. In selected embodiments, a self-expanding metal sheet can be shape-set to an "L" shape and attached to the periphery 1140 of the device frame 1100 as a retention member 1200, forming perpendicular tabs that extend into a second vessel adjoining the selected 120 after being delivered via the delivery catheter system 2000. The delivery catheter system 2000, for example, can contain an outer sheath member 2100 (shown in FIG. 14A) that can be unsheathed to expose the growth device 1000, allowing for the shape-set perpendicular retention members 1200 to be exposed and utilized for delivery of the growth device 1000. In these embodiments, the retention members 1200 can fixate in the adjoining vessels and the growth device 1000 can be pulled proximally with the delivery catheter system 2000 with the retention members 1200 acting as anchors in the second vessel of the patient.

In some embodiments, the retention members 1200 for maintaining the growth device 1000 in the pulmonary artery 122 can be composed of nitinol, cobalt chromium, stainless steel or other metal alloys, without limitation. The retention members 1200 can be attached to the device frame 1100 in any suitable manner, including, but not limited to, suture, welding, riveting, lamination and/or a separate mechanical lock. The retention members 1200 can be distributed around the periphery 1140 of the device frame 1100. In selected embodiments, the retention members 1200 can be uniformly and/or unevenly distributed around the periphery 1140. The retention members 1200 can be oriented in a direction such that they can extend down a length of the second vessel.

Figure 5A:
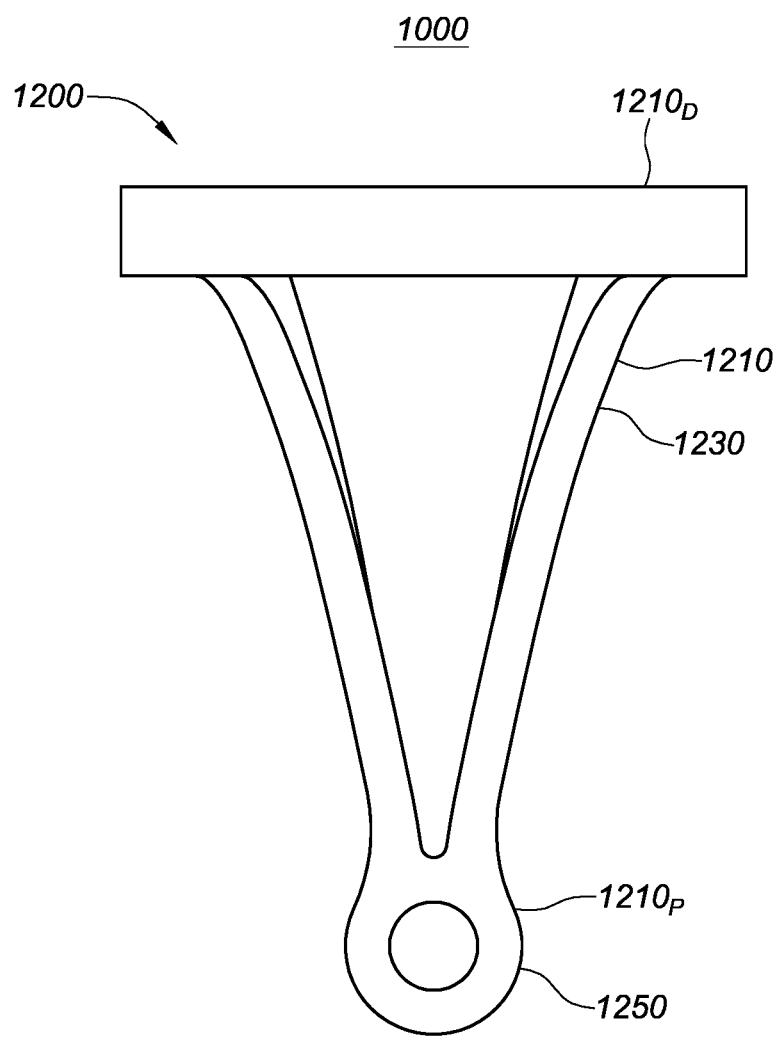
FIG. 5A is a detail drawing illustrating an exemplary embodiment of a retention member for the growth device of FIG. 2.
Figure 8:
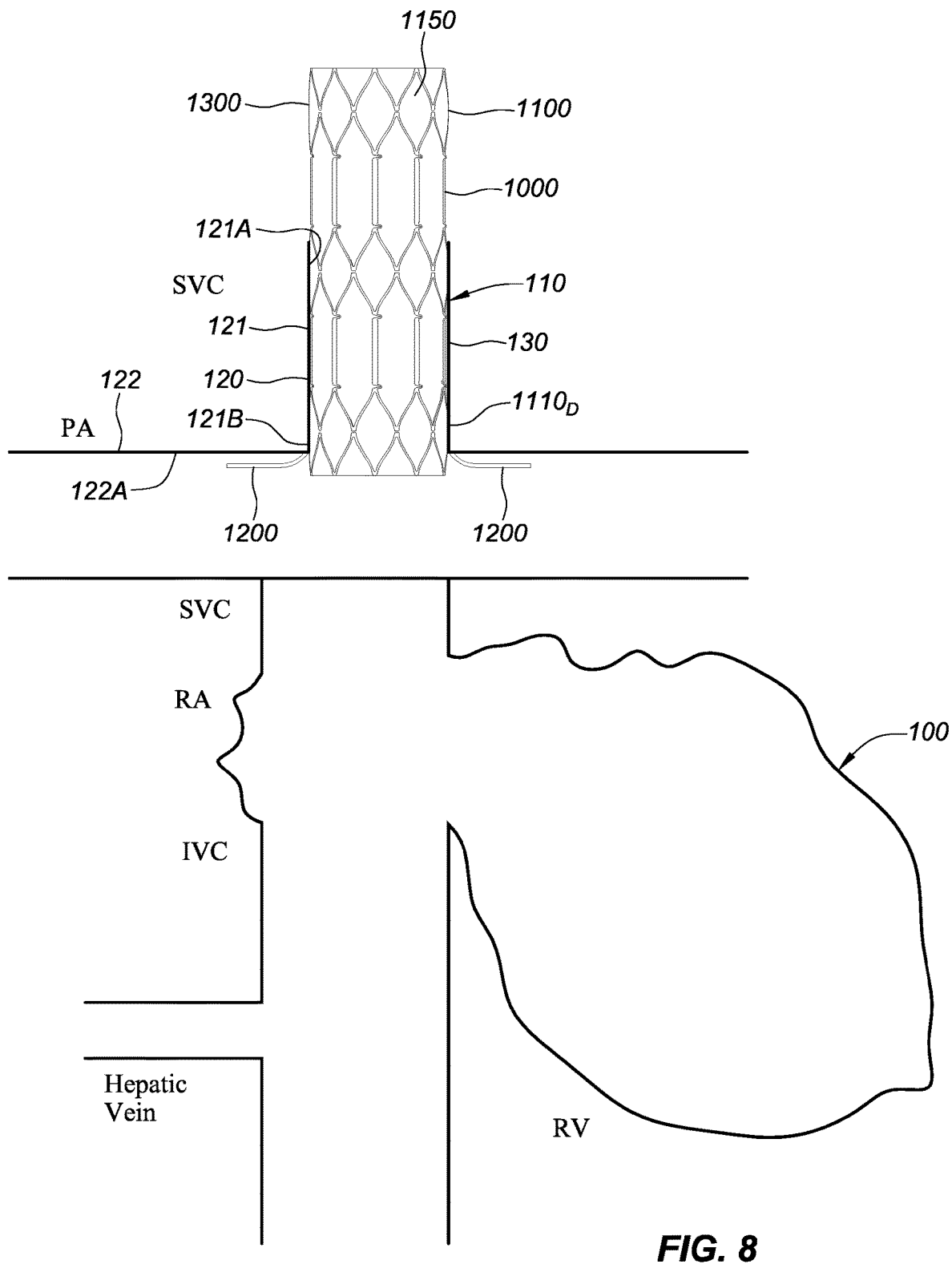
FIG. 8 is a detail drawing illustrating yet another exemplary alternative embodiment of the growth device of FIG. 2, wherein the growth device is implanted in the Glenn position within the patient.

Turning to FIG. 5A, the retention member 1200 can comprise a central retention member body 1210 with a proximal end region 1210$_P$ for coupling with the periphery 1140 of the device frame 1100 (shown in FIGS. 2 and 5A-E) and a distal end region 1210$_D$ for engaging the selected vessel or other lumen 120 (shown in FIG. 8) of the patient 100 (shown in FIG. 8). The proximal end region 1210$_P$ of the central retention member body 1210, in selected embodiments, can be configured to couple with a selected growth cell junction 1127 (shown in FIG. 5B) of the device frame 1100. For example, the central retention member body 1210 can include an engagement member 1250 for coupling with the selected growth cell junction 1127. The central retention member body 1210 can be coupled with an interior surface of the periphery 1140 (shown in FIGS. 2 and 5A-E) inside of the device frame 1100 and/or an exterior surface of the periphery 1140 outside of the device frame 1100. The central retention member body 1210 can couple with the device frame 1100 in any suitable manner, including, but not limited to, a suture, a wire, a weld, an adhesive and/or a bonding polymer layer.

Figure 5B:
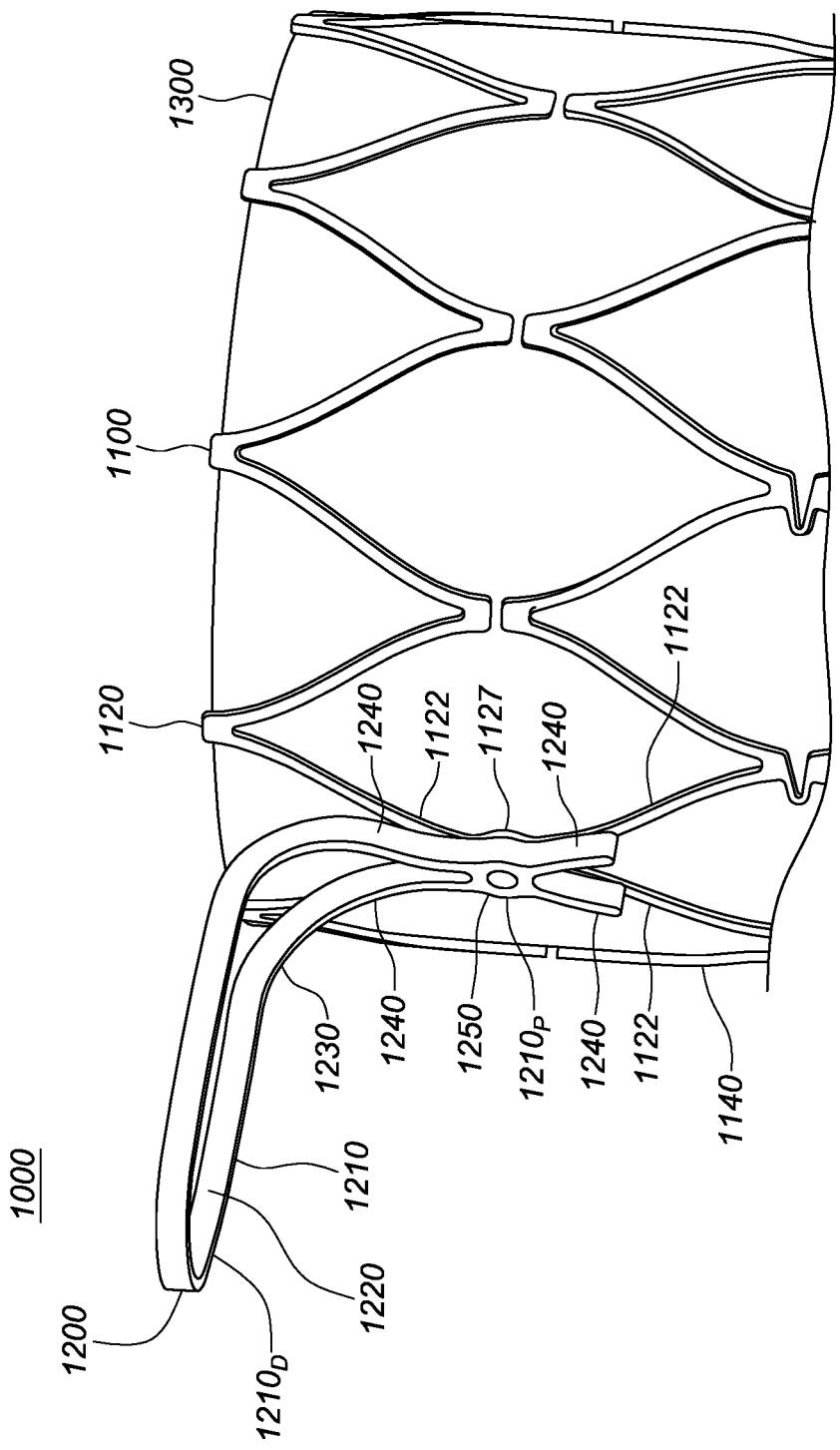
FIG. 5B is a detail drawing illustrating an exemplary alternative embodiment of the retention member of FIG. 5A, wherein the retention member comprises a hollow retention member with one or more stabilizing members.

The proximal end region 1210$_P$ of the central retention member body 1210 can be flushly coupled with the device frame 1100 as illustrated in FIG. 5B. Stated somewhat differently, the proximal end region 1210$_P$ can be disposed in a parallel configuration relative to the periphery 1140 of the device frame 1100. The central retention member body 1210 can comprise a curved member body such that the distal end region 1210$_D$ can extend from the periphery 1140 of the device frame 1100 at a predetermined angle. In selected embodiments, the central retention member body 1210 can include a curved member body portion 1230 such that the distal end region 1210$_D$ is disposed at the predetermined angle relative to the proximal end region 1210$_P$.

Each retention member 1200 can be provided with any suitable size, shape or other configuration. In selected embodiments, the retention member 1200 can include one or more stabilizing members 1240. When the retention member 1200 is coupled with the device frame 1100, each stabilizing member 1240 can be configured to engage an adjacent growth cell strut 1122 as illustrated in FIG. 5B to help increase a stability of the retention member 1200. In selected embodiments, the stabilizing members 1240 can be disposed around the engagement member 1250. The stabilizing members 1240, in other words, can extend proximally from the engagement member 1250 and/or can extend distally from the engagement member 1250. Thereby, the stabilizing members 1240 can engage one or more of the growth cell struts 1122 adjacent to the selected growth cell junction 1127. The stabilizing member 1240 can couple with the adjacent growth cell strut 1122 in any suitable manner, including, a suture, a wire, a weld, an adhesive and/or a bonding polymer layer, without limitation. The suture and/or the wire, for example, can be wrapped around the stabilizing member 1240 and the adjacent growth cell strut 1122.

The retention member 1200 of FIG. 5B can comprise a central retention member body 1210 with a proximal end region 1210$_P$ for coupling with the periphery 1140 of the device frame 1100 and a hollow distal end region 1210$_D$ for engaging the selected vessel or other lumen 120 (shown in FIG. 8) of the patient 100 (shown in FIG. 8). Stated somewhat differently, the retention member 1200 can comprise a hollow retention member with the distal end region 1210$_D$ defining a retention member opening 1220 as shown in FIG. 5B. In selected embodiments, the central retention member body 1210 can include a curved member body portion 1230 such that the distal end region 1210$_D$ is disposed at the predetermined angle relative to the proximal end region 1210$_P$. The retention member opening 1220 can be formed in any suitable manner.

The retention member 1200, for example, can comprise a wire-based retention member. The central retention member body 1210 of the retention member 1200, in other words, can formed from a wire or other thin rod that can be formed into a loop for defining the retention member opening 1220. The retention member 1200, when comprising a wire-based retention member, advantageously can be readily compressed when the growth device 1000 is crimped to the implantation state and/or can provide a wide distal end region 1210$_D$ for engaging the selected lumen 120 of the patient 100 when the growth device 1000 is later expanded into one of the stable expanded states. The wide distal end region 1210$_D$ can help prevent the retention member 1200 from torquing side to side during implantation, deployment and subsequent use.

Figure 5C:
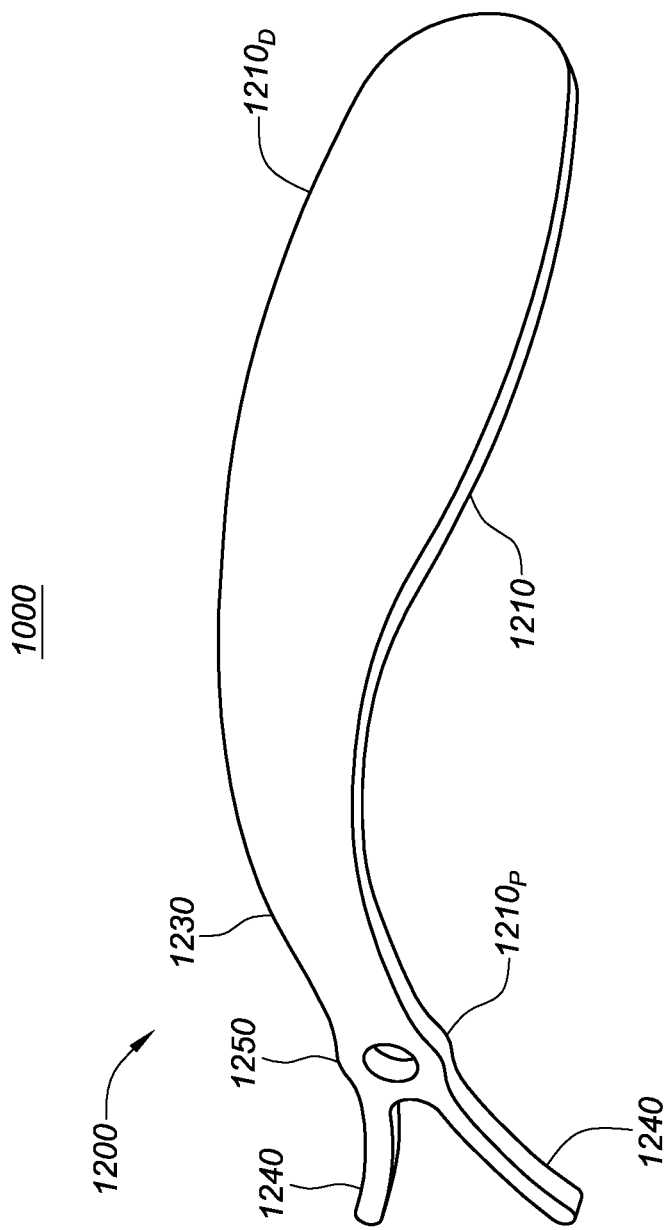
FIG. 5C is a detail drawing illustrating an exemplary alternative embodiment of the retention member of FIG. 5B, wherein the retention member comprises a solid retention member.

Additionally and/or alternatively, the retention member 1200 can comprise a central retention member body 1210 with a proximal end region 1210$_P$ for coupling with the periphery 1140 of the device frame 1100 (FIGS. 2 and 5A-E) and a solid distal end region 1210$_D$ for engaging the selected vessel or other lumen 120 (shown in FIG. 8) of the patient 100 (shown in FIG. 8) as illustrated in FIG. 5C. The central retention member body 1210, in selected embodiments, can include a curved member body portion 1230 such that the distal end region 1210$_D$ is disposed at the predetermined angle relative to the proximal end region 1210$_P$. Unlike the wire-based retention member of FIG. 5B, the solid distal end region 1210$_D$ of the retention member 1200 does not define a retention member opening 1220. The retention member 1200 with the solid distal end region 1210$_D$ advantageously can provide increased retention strength for engaging the selected lumen 120 of the patient 100 when the growth device 1000 is expanded into one of the stable expanded states.

When the growth device 1000 is deployed and/or expanded within a patient 100 (shown in FIG. 8), the retention members 1200 can engage a selected vessel or other lumen 120 (shown in FIG. 8) of the patient 100 and maintain a position of the growth device 1000 within the selected lumen 120. In other words, the retention members 1200 can help resist migration of the growth device 1000 out of the selected lumen 120. The retention members 1200 advantageously can be deployed along a length of the selected lumen 120. A length of the distal end region 1210$_D$ of the retention member 1200 thereby can be increased or otherwise maximized and/or the distal end region 1210$_D$ can engage an entry surface of the selected lumen 120 of the patient 100 in a flush manner. Additionally and/or alternatively, the deployment of the retention members 1200 advantageously can help to minimize occlusion of the selected vessel by the growth device 1000 by avoiding a natural bias of the growth device 1000 to migrate toward a center of the selected vessel.

Figure 5D:
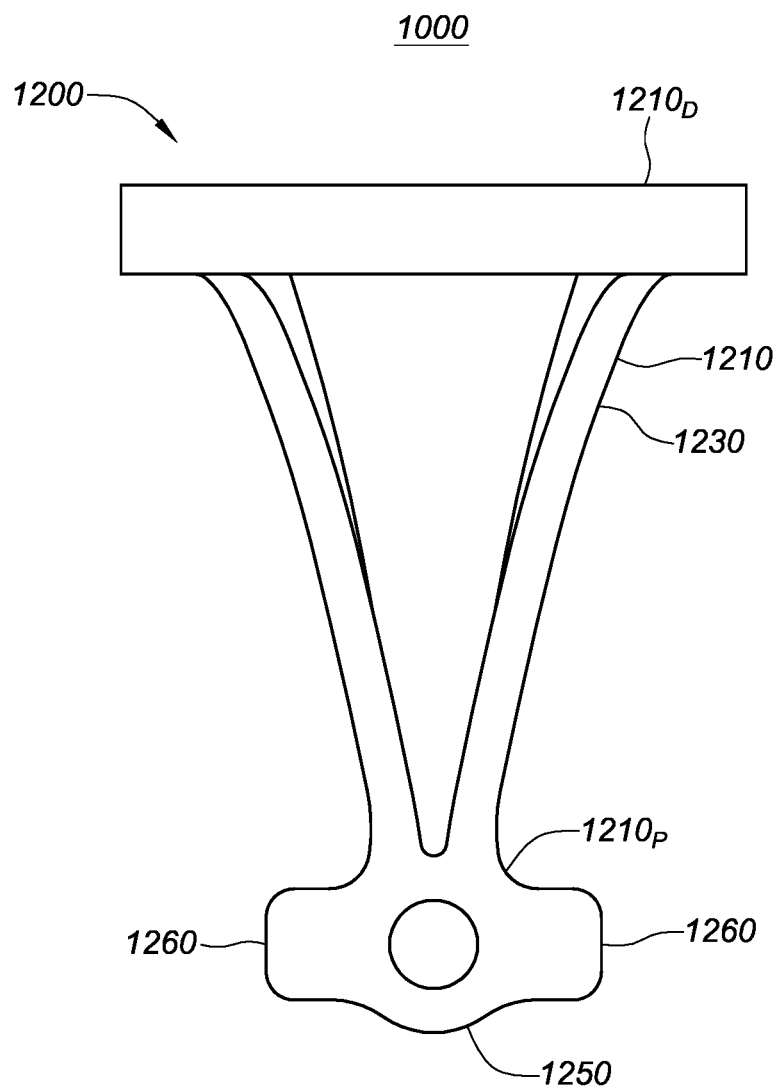
FIG. 5D is a detail drawing illustrating another exemplary alternative embodiment of the retention member of FIG. 5A, wherein the retention member includes one or more wing extension members.

The retention member 1200 optionally can include one or more wing extension members 1260 as illustrated in FIG. 5D. In the manner discussed in more detail above with reference to FIGS. 5A-C, the retention member 1200 can comprise a central retention member body 1210 with a proximal end region $1210_P$ for coupling with the periphery 1140 of the device frame 1100 (shown in FIGS. 2 and 5A-E) and a distal end region $1210_D$ for engaging the selected vessel or other lumen 120 (shown in FIG. 8) of the patient 100 (shown in FIG. 8). The central retention member body 1210, in selected embodiments, can include a curved member body portion 1230 such that the distal end region $1210_D$ is disposed at the predetermined angle relative to the proximal end region $1210_P$. Each wing extension member 1260 is shown as extending laterally from the proximal end region $1210_P$ of the retention member 1200. The wing extension member 1260, for example, can extend laterally from the engagement member 1250 of the retention member 1200. Advantageously, the wing extension member 1260 can comprise a retention aid for coupling the retention member 1200 with the device frame 1100 (shown in FIGS. 2 and 5A-E). The wing extension member 1260 likewise can help resist side to side deflection of the distal end region $1210_D$ of the retention member 1200.

Figure 5E:
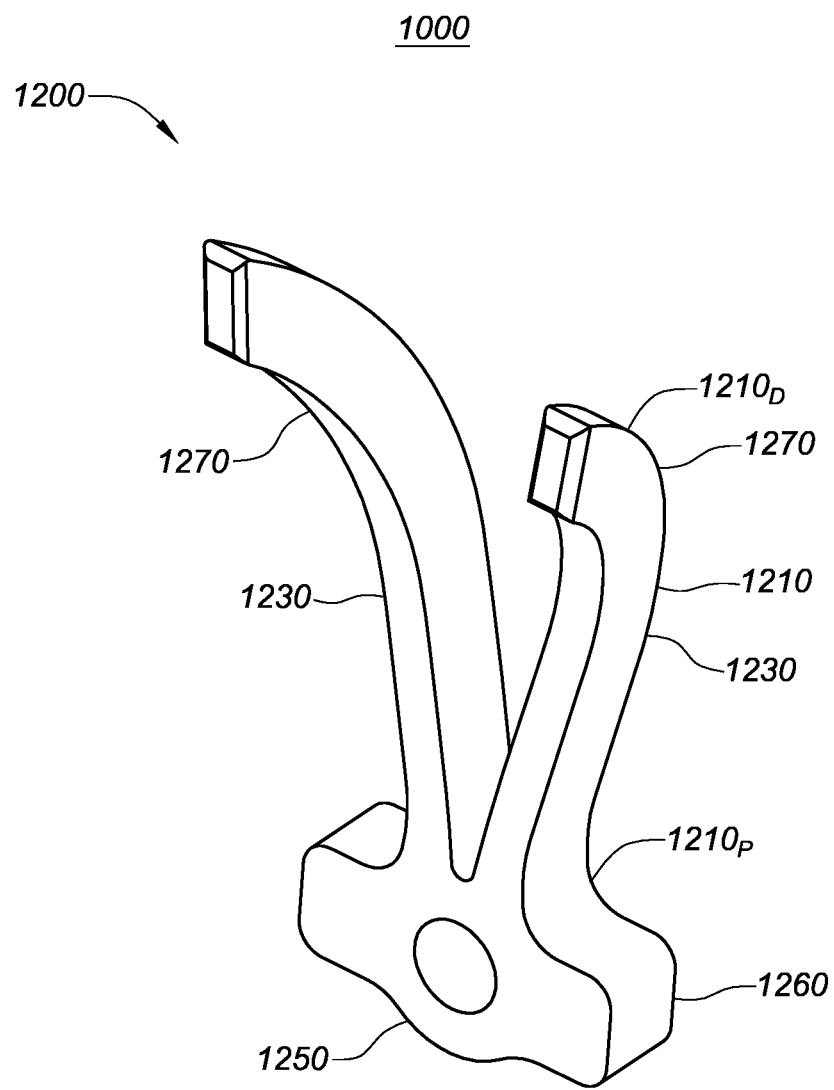
FIG. 5E is a detail drawing illustrating yet another exemplary alternative embodiment of the retention member of FIG. 5A, wherein the retention member includes a forked distal end region.

The retention member 1200 illustrated in FIG. 5E can comprise a central retention member body 1210 with a proximal end region $1210_P$ for coupling with the periphery 1140 of the device frame 1100 (shown in FIGS. 2 and 5A-E) and a forked distal end region $1210_D$ for engaging the selected vessel or other lumen 120 (shown in FIG. 8) of the patient 100 (shown in FIG. 8). Stated somewhat differently, the distal end region $1210_D$ of the retention member 1200 of FIG. 5E can be provided with a forked shape, or a V-shape, with two branches (or end regions) 1270 for engaging the selected vessel. Each of the branches 1270 can engage a separate portion of the selected vessel. The central retention member body 1210, in selected embodiments, can include a curved member body portion 1230 such that the distal end region $1210_D$ is disposed at the predetermined angle relative to the proximal end region $1210_P$. Each branch 1270 of the distal end region $1210_D$ can include a separate curved member body portion 1230 as shown in FIG. 5E.

Figure 5F:
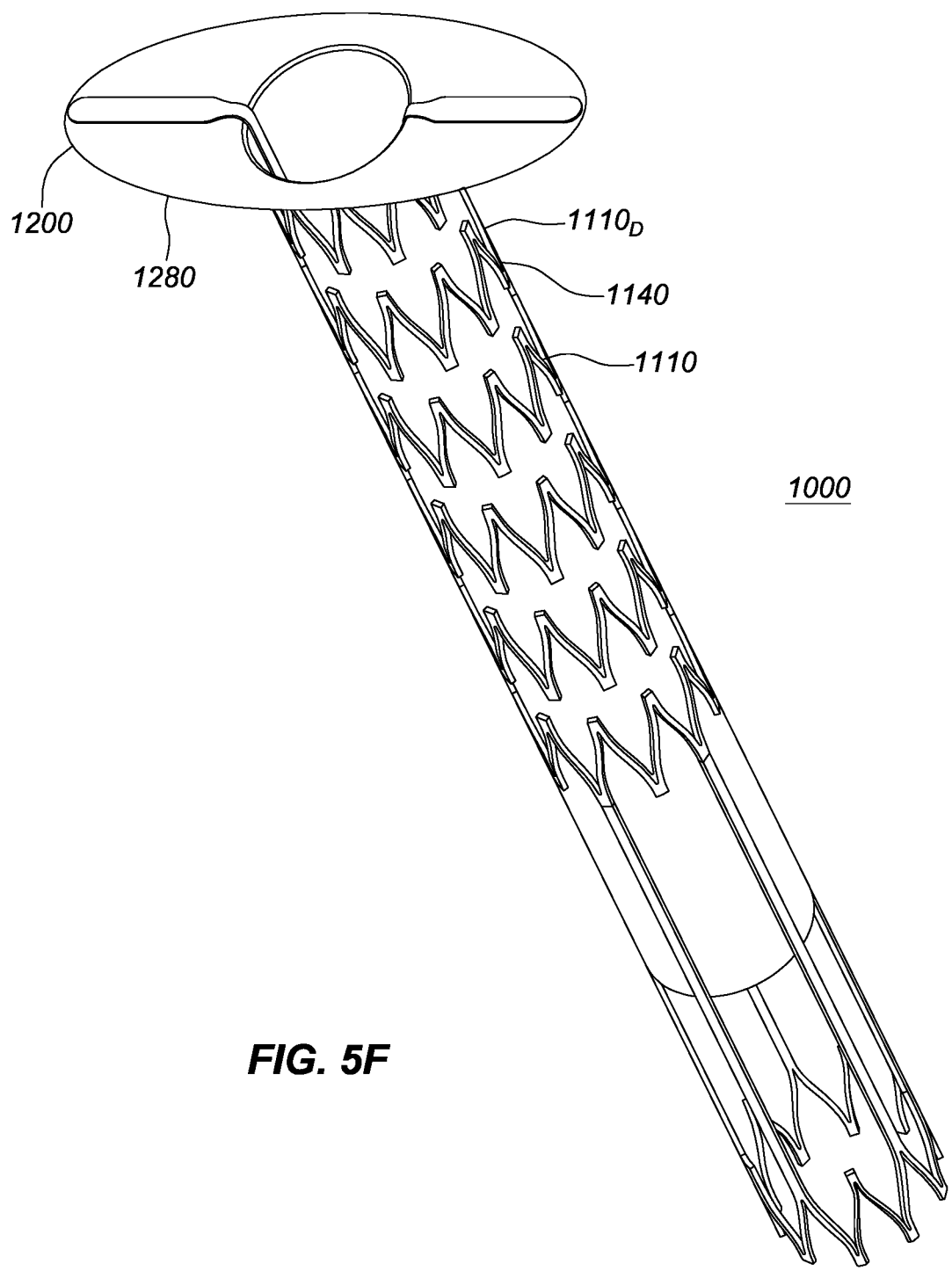
FIG. 5F is a detail drawing illustrating still another exemplary alternative embodiment of the retention member of FIG. 5A, wherein the retention member comprises a circumferential retention member.

In selected embodiments, the retention member 1200 can comprise a circumferential retention member as illustrated in FIG. 5F. The retention member 1200 can include a retention member profile 1280 that, when deployed, can extend radially from the distal end region $1110_D$ of the device frame 1100 for engaging the selected vessel or other lumen 120 (shown in FIG. 8) of the patient 100 (shown in FIG. 8). Stated somewhat differently, the retention member profile 1280 can comprised a solid profile that can extend radially from the periphery 1140 of the device frame 1100 when deployed. Although shown as comprising a solid oval retention member profile in FIG. 5F for purposes of illustration only, the retention member profile 1280 can be provided with any suitable predetermined size, shape, diameter or other dimension. For example, the retention member profile 1280 can be based upon a size, shape or other geometry of the selected vessel or other lumen 120 of the patient 100.

Returning again to FIG. 2, the growth device 1000 optionally can include a covering member 1300. The covering member 1300 advantageously can provide a radial seal for the growth device 1000. For example, the covering member 1300 can seal the growth device 1000 at an intersection of the selected vessel and a crossing source vessel of the patient 100. The covering member 1300 optionally can provide a seal for one or more walls of the source vessel.

The covering member 1300 can be provided in any suitable manner and preferably is blood impermeable. In selected embodiments, the covering member 1300 can be made of cloth, one or more braids, one or more weaves, and/or one or more polymers. If the covering member 1300 is made of cloth, the cloth may have a smooth surface void of creases and folds throughout the diameter range of the growth device 1000. The covering member, for example, can comprise a stretchable cloth material that is constantly taut at each diameter configuration. The cloth may also be tacked down and able to unfold at each diameter expansion. The cloth material may have a mechanical mechanism, similar to a one-way zip-tie or ratchet, to help ensure that no slack exists in the cloth at the lower diameter ranges. The cloth may be composed of polymers, rubbers, or other bio-inert materials.

The covering member 1300 can be coupled or otherwise associated with the device frame 1100. As shown in FIG. 2, for example, the covering member 1300 can be disposed about the periphery 1140 of the device frame 1100. The covering member 1300, for example, can be disposed about an interior surface of the periphery 1140 inside of the device frame 1100 and/or about an exterior surface of the periphery 1140 outside of the device frame 1100.

Additionally and/or alternatively, the covering member 1300 can extend from the proximal end region $1110_P$ of the device frame 1100 to the distal end region $1110_D$ of the device frame 1100, in whole or in part, depending upon a predetermined application of the growth device 1000, an implant location of the growth device 1000 within a patient 100 (shown in FIG. 8) and/or an anatomy of the patient 100, without limitation. In selected embodiments, the device frame 1100 can comprise a covered frame portion 1112 (shown in FIG. 11A) and an uncovered frame portion 1114 (shown in FIG. 11A), wherein the covering member 1300 is associated with the covered frame portion 1112 and not with the uncovered frame portion 1114. In some embodiments, partial covering of the device frame 1100 of the growth device 1000 can be utilized to overlap or otherwise cooperate with a second growth device 1000B (shown in FIGS. 10A-B) to fit a desired length of coverage. The covering member 1300 optionally can encapsulate the device frame 1100.

Advantageously, the covering member 1300 can compress and/or expand with the device frame 1100 throughout the operating range of diameters, cross-sections or other dimensions of the growth device 1000 from implantation through expansion. The covering member 1300, in other words, can be compressed when the growth device 1000 is crimped to the implantation state and/or can expand as the growth device 1000 is expanded to one or more stable expanded states.

A thickness of the covering member 1300 can be decreased to help improve a crimp profile of the growth device 1000 in the implantation state and/or can be increased to help improve an expandability and/or structural integrity of the growth device 1000. A coupling between the covering member 1300 and the device frame 1100 preferably can help ensure that the covering member 1300 remains coupled with the device frame 1100 throughout the operating range of the growth device 1000. The covering member 1300, for example, can be laminated onto the device frame 1100, sutured with the device frame 1100 and/or compressed on the device frame 1100, without limitation.

Figure 6:
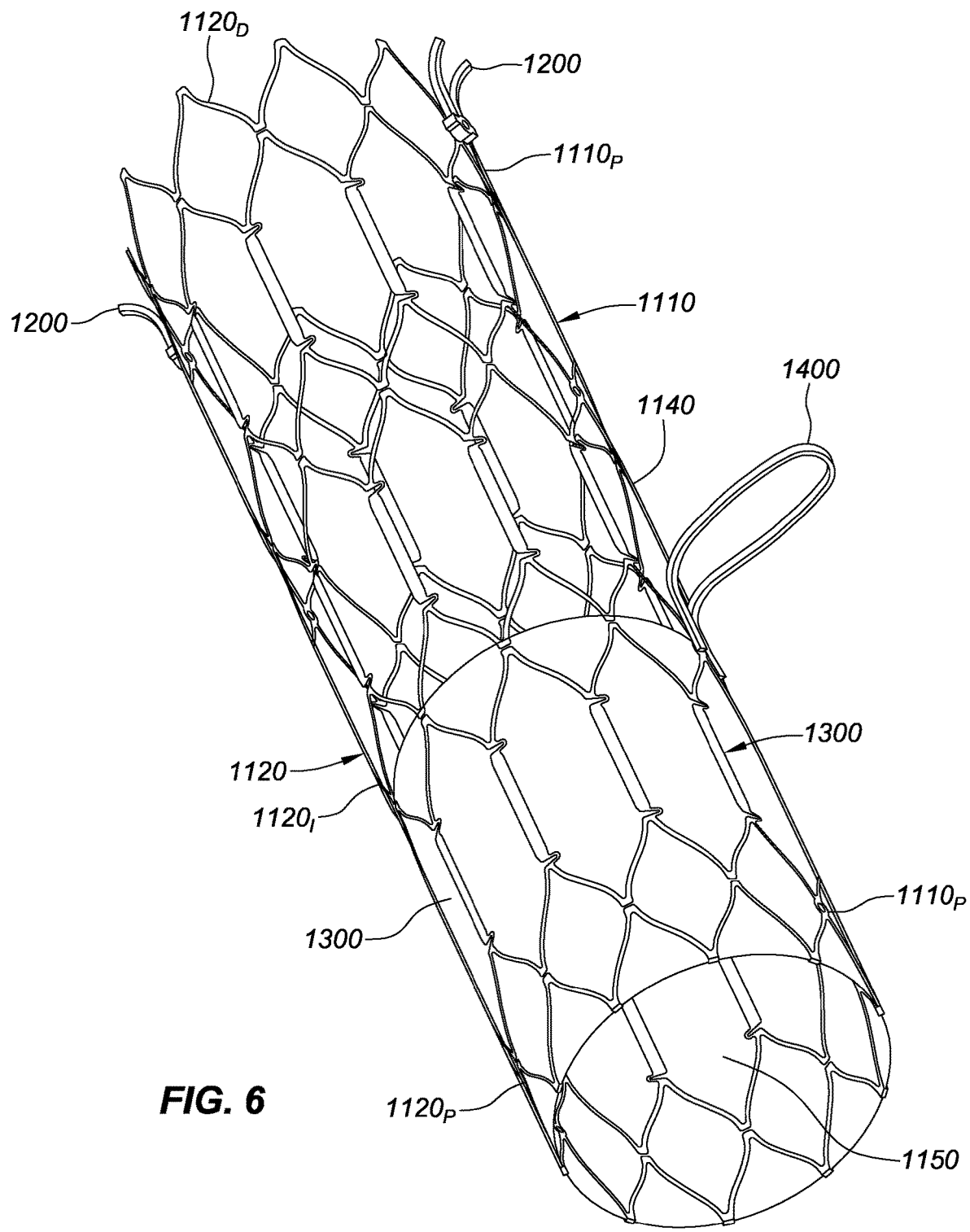
FIG. 6 is a detail drawing illustrating another exemplary alternative embodiment of the growth device of FIG. 2, wherein the growth device includes at least one anchor member.

Turning to FIG. 6, the growth device 1000 is shown as further including one or more anchor members 1400 for engaging selected vessel tissue and preventing migration of the growth device 1000 within the patient 100 and, in selected embodiments, advantageously can be utilized to hepatic veins within a patient 100. The growth device 1000 of FIG. 6 can be provided in the manner discussed in more detail above with reference to FIGS. 2, 3A-E and 4. For example, the growth device 1000 can comprise a device frame 1100 that includes a plurality of annular growth cell members 1120 and one or more annular spacing members 1130. The growth cell members 1120 and the spacing members 1130 can define a periphery 1140 of the device frame 1100 and extend from a proximal end region $1110_P$ of the device frame 1100 to a distal end region $1110_D$ of the device frame 1100. As shown in FIG. 6, each spacing member 1130 can be disposed between a pair of adjacent growth cell members 1120. Stated somewhat differently, the device frame 1100 can comprise a series (or sequence) of alternating growth cell members 1120 and spacing members 1130 that span axially between the proximal and distal end regions $1110_P$, $1110_D$ and that can provide a radial periphery 1140 for the device frame 1100. The sequence of growth cell members 1120 and spacing members 1130 thereby can define a central axial channel 1150 of the elongated device frame 1100.

The growth device 1000 of FIG. 6 optionally can include one or more retention members 1200 for engaging the selected vessel or other lumen 120 (shown in FIG. 8) of the patient 100 (shown in FIG. 8). Each retention member 1200 can be provided in the manner discussed in more detail above with reference to FIGS. 5A-E and can be disposed at the proximal end region $1110_P$ and/or the distal end region $1110_D$ of the device frame 1100 and can extend radially from the periphery 1140. Stated somewhat differently, the growth cell members 1120 can include a proximal growth cell member $1120_P$ that is disposed at the proximal end region $1110_P$ of the device frame 1100 and a distal growth cell member $1120_D$ that is disposed at the distal end region $1110_P$ of the device frame 1100, and the retention members 1200 can be coupled with the proximal growth cell member $1120_P$ and/or the distal growth cell member $1120_D$ and extend radially therefrom.

Additionally and/or alternatively, the growth device 1000 of FIG. 6 can include an optional covering member 1300 for providing a radial seal for the growth device 1000. The covering member 1300 can be provided in the manner discussed in more detail above with reference to FIG. 2. As discussed herein, the covering member 1300 can extend from the proximal end region $1110_P$ of the device frame 1100 to the distal end region $1110_D$ of the device frame 1100, in whole or in part, depending upon a predetermined application of the growth device 1000, an implant location of the growth device 1000 within a patient 100 (shown in FIG. 8) and/or an anatomy of the patient 100, without limitation. The covering member 1300 optionally can encapsulate the device frame 1100 and/or can include one or more abrasive regions (not shown) for encouraging ingrowth and/or retention of the growth device 1000 within the patient 100.

In selected embodiments, any spacing member 1130 that is covered by the covering member 1300 can have spacer member struts 1132 with spacer member strut lengths that are less than (or shorter than) spacer member strut lengths of spacer member struts 1132 that comprise an uncovered spacing member 1130. The shorter spacer member struts 1132 of the covered spacing member 1130 advantageously can help ensure that the hepatic veins of the patient 100 are not covered by any growth cell member 1120 and/or the covering member 1300.

When the growth device 1000 is utilized to treat one or more hepatic veins, for example, at least one retention member 1200 can be deployed into a selected hepatic vein to prevent migration of the anchor member(s) 1400. The hepatic veins enter the inferior vena cava (or IVC) 124 near a transition 124B (shown in FIGS. 9 and 10A-B) between the inferior vena cava 124 and the right atrium 123 of a heart of the patient 100 and should not be blocked. The retention member 1200 advantageously can help prevent the growth device 1000 from blocking the hepatic veins, which blockage could prove fatal to the patient 100. In selected embodiments, the retention member 1200 can be positioned within the most superior hepatic vein of the patient 100 during implantation of the growth device 1000. This positioning of the retention member 1200 can help to ensure that no portion of the growth device 1000 that is covered by the covering member 1300 is deployed over the hepatic veins of the patient 100.

The growth device 1000 of FIG. 6 likewise can include an intermediate growth cell member $1120_I$ that is disposed between the proximal growth cell member $1120_P$ and the distal growth cell member 1120. A first spacing member 1130 can be disposed between the proximal growth cell member $1120_P$ and the intermediate growth cell member $1120_I$, and/or a second spacing member 1130 can be disposed between the intermediate growth cell member 1120I and the distal growth cell member 1120. In selected embodiments, the growth cell members 1120 can include a plurality of intermediate growth cell members $1120_I$ with respective spacing members 1130 being disposed between adjacent intermediate growth cell members $1120_I$ as shown in FIG. 6.

As illustrated in FIG. 6, each anchor member 1400 can be disposed at a selected intermediate growth cell member $1120_I$ of the device frame 1100 and can extend radially from the periphery 1140 of the selected intermediate growth cell member 1120*i*. If the growth device 1000 includes more than one anchor member 1400, the anchor members 1400 can be disposed at the peripheries 1140 of respective intermediate growth cell members 1120*i*. In selected embodiments, the anchor members 1400 can be distributed around the periphery 1140 of a common intermediate growth cell member $1120_I$. The anchor members 1400 can be distributed around the periphery 1140 of the intermediate growth cell member(s) 1120*i* in any predetermined configuration and, as desired, can be evenly distributed around the periphery 1140.

The anchor members 1400 allow for positioning support when delivered via a delivery catheter system 2000 (shown in FIGS. 14A-D) and retention of the growth device 1000 when connecting bloodstreams of different vessels. The growth device 1000, for example, can be configured for deployment in the selected vessel or other lumen 120 (shown in FIG. 8) of the patient 100 (shown in FIG. 8). Each anchor member 1400 can be provided in any suitable manner. The anchor member 1400, for example, can be made from a polymer, a metal or other appropriate material. The anchor member 1400 may comprise paddles, hooks, tabs, spirals, or other suitable shapes. The anchor member 1400 optionally can be covered with cloth or another suitable material for promoting acute sealing, chronic ingrowth and/or retention within the selected lumen of the patient.

In selected embodiments, the device frame 1100 may be flared radially outwardly to form one or more of the anchor members 1400. This flaring may occur by utilizing a balloon expansion system 2200 (shown in FIG. 14B) of the delivery catheter system 2000 if the device frame 1100 is made of balloon-expandable materials such as stainless steel or cobalt chromium. Additionally and/or alternatively, the anchor members 1400 can be shape-set into self-expanding materials like nitinol. In some embodiments, self-expanding anchor members 1400 may be attached to balloon-expandable shunts. This enables catheter delivery as the self-expanding anchor members 1400 can take shape in a perpendicular fashion to the delivery catheter system 2000 and crimped shunt, allowing for retention during deployment and after inflation of the device frame 1100.

The anchor members 1400 may be angled towards a proximal end region of the device frame 1100 and/or towards a distal end region of the device frame 1100 depending on retention or sealing features needed. In some embodiments, the anchor members 1400 can comprise single bars, loops, or other shapes. One or more anchor members 1400 can be disposed around the periphery 1140 of the device frame 1100. In selected embodiments, a self-expanding metal sheet can be shape-set to an "L" shape and attached to the periphery 1140 of the device frame 1100 as an anchor member 1400, forming perpendicular tabs that extend into a second vessel adjoining the selected 120 after being delivered via the delivery catheter system 2000.

The delivery catheter system 2000, for example, can contain an outer sheath member 2100 (shown in FIG. 14A) that can be unsheathed to expose the growth device 1000, allowing for the shape-set perpendicular anchor members 1400 to be exposed and utilized for delivery of the growth device 1000. In these embodiments, the anchor members 1400 can fixate in the adjoining vessels and the growth device 1000 can be pulled proximally with the delivery catheter system 2000 with the anchor members 1400 acting as anchors in the second vessel of the patient.

In some embodiments, the anchor members 1400 for maintaining the growth device 1000 in the pulmonary artery 122 can be composed of nitinol, cobalt chromium, stainless steel or other metal alloys, without limitation. The anchor members 1400 can be attached to the device frame 1100 in any suitable manner, including, but not limited to, suture, welding, riveting, lamination and/or a separate mechanical lock. The anchor members 1400 can be distributed around the periphery 1140 of the device frame 1100. In selected embodiments, the anchor members 1400 can be uniformly and/or unevenly distributed around the periphery 1140. The anchor members 1400 can be oriented in a direction such that they can extend down a length of the second vessel.

Figure 7A:
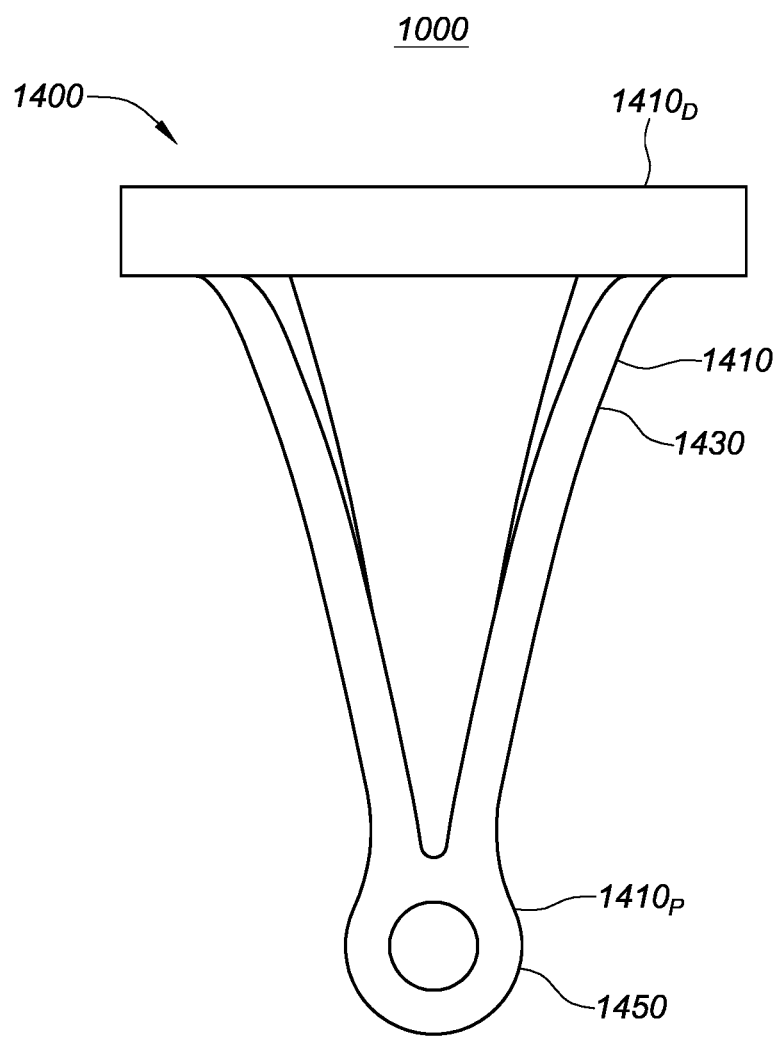
FIG. 7A is a detail drawing illustrating an exemplary embodiment of an anchor member for the growth device of FIG. 6.

Turning to FIG. 7A, the anchor member 1400 can comprise a central anchor member body 1410 with a proximal end region 1410$_P$ for coupling with the periphery 1140 of the selected intermediate growth cell member 1120$_I$ (shown in FIGS. 6 and 7B) and a distal end region 1410$_D$ for engaging tissue adjacent to the selected vessel 120 (shown in FIG. 8) of the patient 100 (shown in FIG. 8). The proximal end region 1410$_P$ of the central anchor member body 1410, in selected embodiments, can be configured to couple with a selected growth cell junction 1127 (shown in FIG. 7B) of the selected intermediate growth cell member 1120$_I$.

For example, the central anchor member body 1410 can include an engagement member 1450 for coupling with the selected growth cell junction 1127. The central anchor member body 1410 can be coupled with an interior surface of the periphery 1140 (shown in FIGS. 6 and 7B) inside of the selected intermediate growth cell member 1120$_I$ and/or an exterior surface of the periphery 1140 outside of the selected intermediate growth cell member 1120$_I$. The central anchor member body 1410 can couple with the selected intermediate growth cell member 1120$_I$ in any suitable manner, including, but not limited to, a suture, a wire, a weld, an adhesive and/or a bonding polymer layer.

Figure 7B:
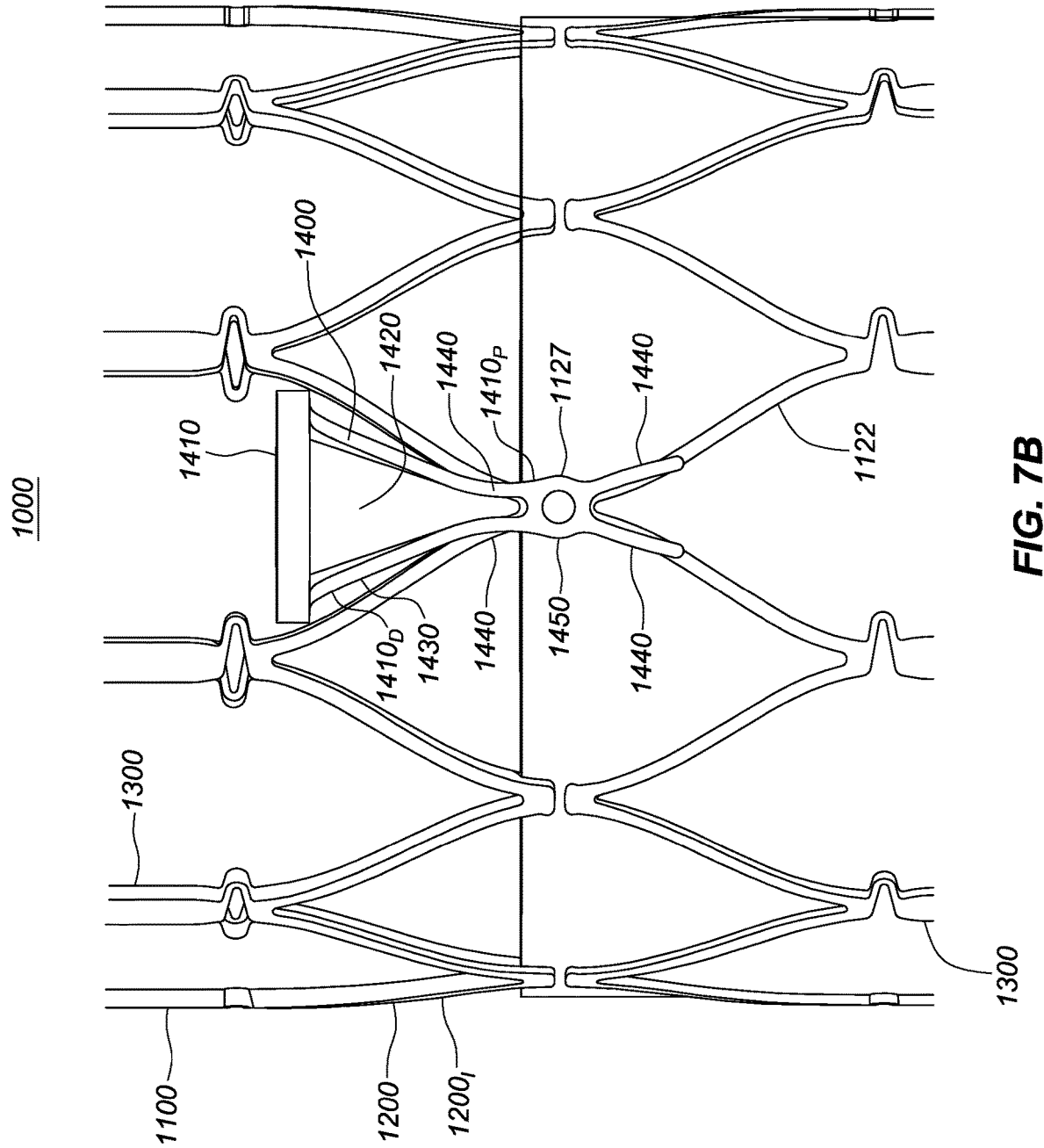
FIG. 7B is a detail drawing illustrating an exemplary alternative embodiment of the anchor member of FIG. 7A, wherein the anchor member comprises a hollow anchor member with one or more stabilizing members.

The proximal end region 1410$_P$ of the central anchor member body 1410 can be flushly coupled with the selected intermediate growth cell member 1120$_I$ as illustrated in FIG. 7B. Stated somewhat differently, the proximal end region 1410$_P$ can be disposed in a parallel configuration relative to the periphery 1140 of the selected intermediate growth cell member 1120$_I$. The central anchor member body 1410 can comprise a curved member body such that the distal end region 1410$_D$ can extend from the periphery 1140 of the selected intermediate growth cell member 1120$_I$ at a predetermined angle. In selected embodiments, the central anchor member body 1410 can include a curved member body portion 1430 such that the distal end region 1410$_D$ is disposed at the predetermined angle relative to the proximal end region 1410$_P$.

Each anchor member 1400 can be provided with any suitable size, shape or other configuration. In selected embodiments, the anchor member 1400 can include one or more stabilizing members 1440. When the anchor member 1400 is coupled with the selected intermediate growth cell member 1120$_I$, each stabilizing member 1440 can be configured to engage an adjacent growth cell strut 1122 as illustrated in FIG. 7B to help increase a stability of the anchor member 1400. In selected embodiments, the stabilizing members 1440 can be disposed around the engagement member 1450. The stabilizing members 1440, in other words, can extend proximally from the engagement member 1450 and/or can extend distally from the engagement member 1450. Thereby, the stabilizing members 1440 can engage one or more of the growth cell struts 1122 adjacent to the selected growth cell junction 1127. The stabilizing member 1440 can couple with the adjacent growth cell strut 1122 in any suitable manner, including a suture, a wire, a weld, an adhesive and/or a bonding polymer layer, without limitation. The suture and/or the wire, for example, can be wrapped around the stabilizing member 1440 and the adjacent growth cell strut 1122.

The anchor member 1400 of FIG. 7B can comprise a central anchor member body 1410 with a proximal end region 1410$_P$ for coupling with the periphery 1140 of the selected intermediate growth cell member 1120$_I$ and a hollow distal end region 1410$_D$ for engaging tissue adjacent to the selected vessel 120 (shown in FIG. 8) of the patient 100 (shown in FIG. 8). Stated somewhat differently, the anchor member 1400 can comprise a hollow anchor member with the distal end region 1410$_D$ defining an anchor member opening 1420 as shown in FIG. 7B. In selected embodiments, the central anchor member body 1410 can include a curved member body portion 1430 such that the distal end region 1410$_D$ is disposed at the predetermined angle relative to the proximal end region 1410$_P$. The anchor member opening 1420 can be formed in any suitable manner.

The anchor member 1400, for example, can comprise a wire-based anchor member. The central anchor member body 1410 of the anchor member 1400, in other words, can formed from a wire or other thin rod that can be formed into a loop for defining the anchor member opening 1420. The anchor member 1400, when comprising a wire-based anchor member, advantageously can be readily compressed when the growth device 1000 is crimped to the implantation state and/or can provide a wide distal end region $1410_D$ for engaging the selected vessel tissue of the patient 100 when the growth device 1000 is later expanded into one of the stable expanded states. The wide distal end region $1410_D$ can help prevent the anchor member 1400 from torquing side to side during implantation, deployment and subsequent use.

Figure 7C:
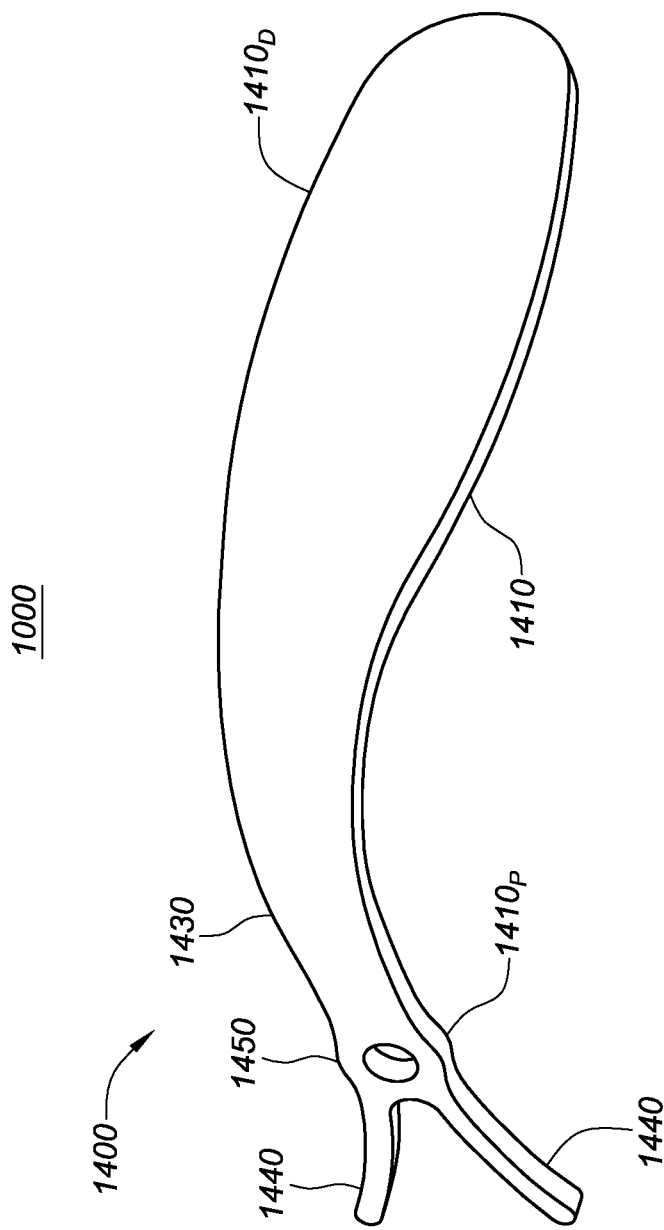
FIG. 7C is a detail drawing illustrating an exemplary alternative embodiment of the anchor member of FIG. 7B, wherein the anchor member comprises a solid anchor member.

Additionally and/or alternatively, the anchor member 1400 can comprise a central anchor member body 1410 with a proximal end region $1410_P$ for coupling with the periphery 1140 of the selected intermediate growth cell member $1120_I$ (shown in FIGS. 6 and 7B) and a solid distal end region $1410_D$ for engaging tissue adjacent to the selected vessel 120 (shown in FIG. 8) of the patient 100 (shown in FIG. 8) as illustrated in FIG. 7C. The central anchor member body 1410, in selected embodiments, can include a curved member body portion 1430 such that the distal end region $1410_D$ is disposed at the predetermined angle relative to the proximal end region $1410_P$. Unlike the wire-based anchor member of FIG. 7B, the solid distal end region $1410_D$ of the anchor member 1400 does not define an anchor member opening 1420. The anchor member 1400 with the solid distal end region $1410_D$ advantageously can provide increased anchor strength for engaging the selected vessel tissue when the growth device 1000 is expanded into one of the stable expanded states.

When the growth device 1000 is deployed and/or expanded within a patient 100 (shown in FIG. 8), the anchor members 1400 can engage the selected vessel tissue and maintain a position of the growth device 1000 within the patient 100. In other words, the anchor members 1400 can help resist migration of the growth device 1000 out of the selected lumen 120. The anchor members 1400 advantageously can be deployed along a length of the selected lumen 120. A length of the distal end region $1410_D$ of the anchor member 1400 thereby can be increased or otherwise maximized and/or the distal end region $1410_D$ can engage an entry surface of the selected lumen 120 of the patient 100 in a flush manner. Additionally and/or alternatively, the deployment of the anchor members 1400 advantageously can help to minimize occlusion of the selected vessel by the growth device 1000 by avoiding a natural bias of the growth device 1000 to migrate toward a center of the selected vessel.

Figure 7D:
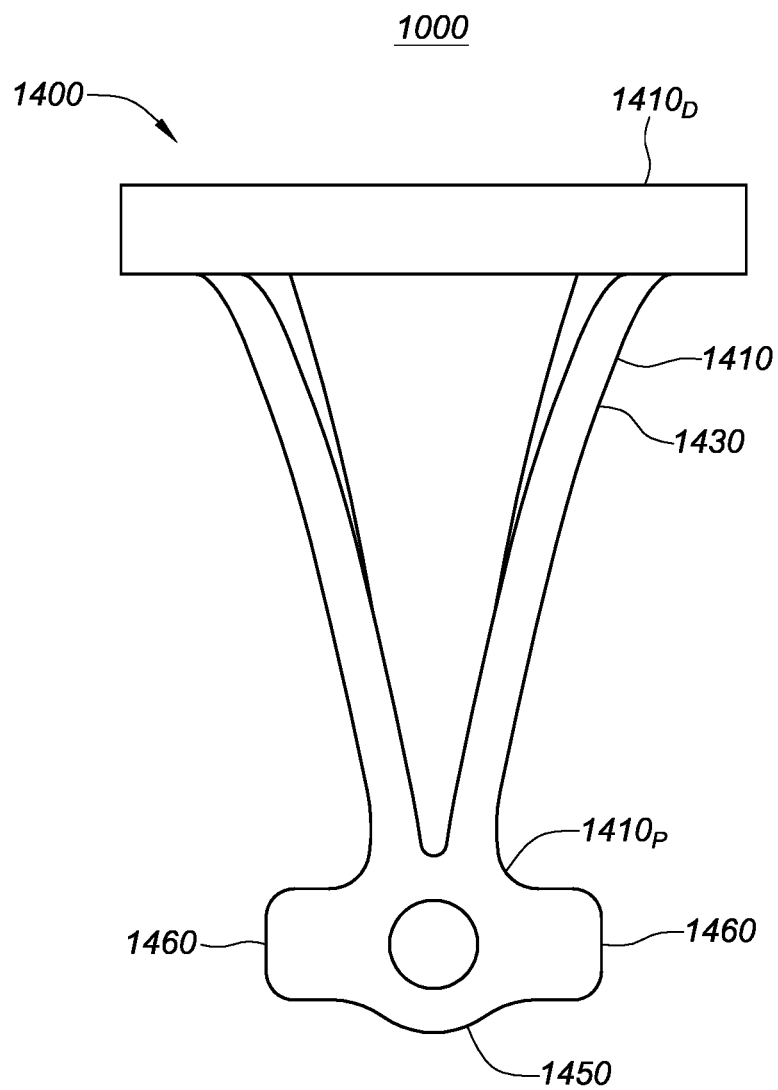
FIG. 7D is a detail drawing illustrating another exemplary alternative embodiment of the anchor member of FIG. 7A, wherein the anchor member includes one or more wing extension members.

The anchor member 1400 optionally can include one or more wing extension members 1460 as illustrated in FIG. 7D. In the manner discussed in more detail above with reference to FIGS. 7A-C, the anchor member 1400 can comprise a central anchor member body 1410 with a proximal end region $1410_P$ for coupling with the periphery 1140 of the selected intermediate growth cell member $1120_I$ (shown in FIGS. 6 and 7B) and a distal end region $1410_D$ for engaging tissue adjacent to the selected vessel 120 (shown in FIG. 8) of the patient 100 (shown in FIG. 8). The central anchor member body 1410, in selected embodiments, can include a curved member body portion 1430 such that the distal end region $1410_D$ is disposed at the predetermined angle relative to the proximal end region $1410_P$. Each wing extension member 1460 is shown as extending laterally from the proximal end region $1410_P$ of the anchor member 1400. The wing extension member 1460, for example, can extend laterally from the engagement member 1450 of the anchor member 1400. Advantageously, the wing extension member 1460 can comprise a retention aid for coupling the anchor member 1400 with the selected intermediate growth cell member 11201 (shown in FIGS. 6 and 7B). The wing extension member 1460 likewise can help resist side to side deflection of the distal end region $1410_D$ of the anchor member 1400.

Figure 7E:
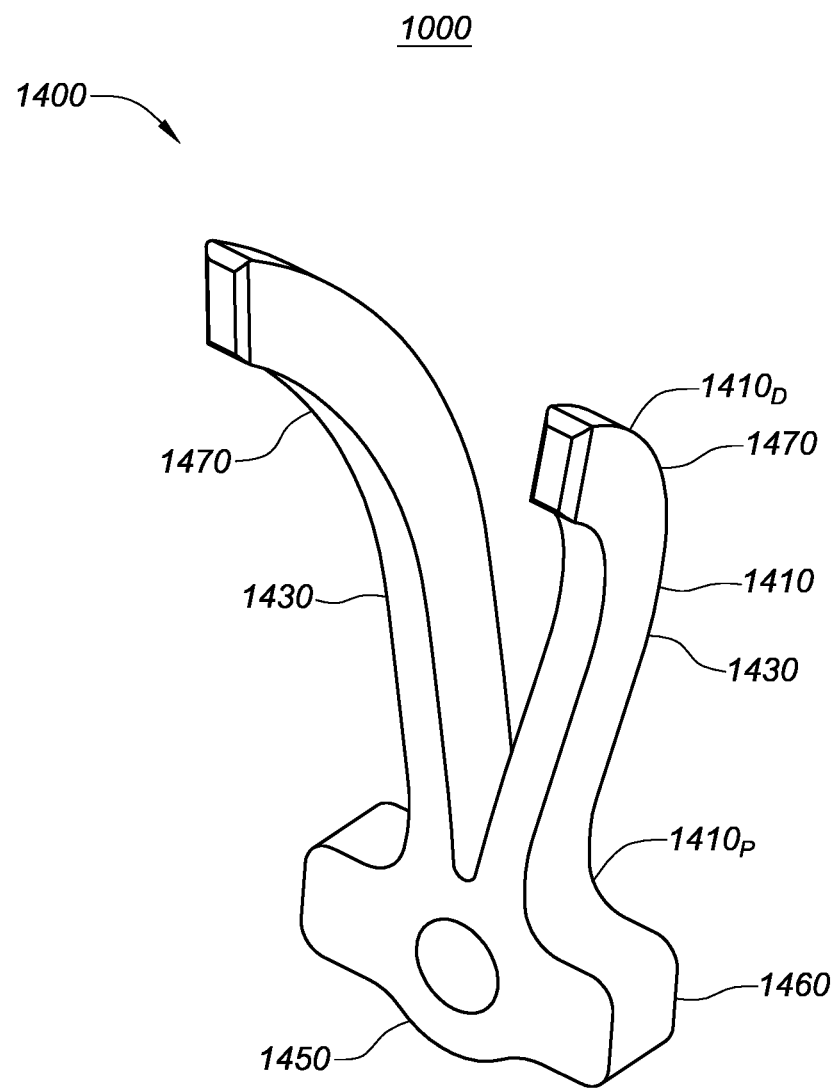
FIG. 7E is a detail drawing illustrating yet another exemplary alternative embodiment of the anchor member of FIG. 7A, wherein the anchor member includes a forked distal end region.

The anchor member 1400 illustrated in FIG. 7E can comprise a central anchor member body 1410 with a proximal end region $1410_P$ for coupling with the periphery 1140 of the selected intermediate growth cell member $1120_I$ (shown in FIGS. 6 and 7B) and a forked distal end region $1410_D$ for engaging tissue adjacent to the selected vessel 120 (shown in FIG. 8) of the patient 100 (shown in FIG. 8). Stated somewhat differently, the distal end region $1410_D$ of the anchor member 1400 of FIG. 7E can be provided with a forked shape, or a V-shape, with two branches (or end regions) 1470 for engaging the selected vessel. Each of the branches 1470 can engage a separate portion of the selected vessel. The central anchor member body 1410, in selected embodiments, can include a curved member body portion 1430 such that the distal end region $1410_D$ is disposed at the predetermined angle relative to the proximal end region $1410_P$. Each branch 1470 of the distal end region $1410_D$ can include a separate curved member body portion 1430 as shown in FIG. 7E.

In use, the growth device 1000 can be crimped or otherwise compressed into an implantation state in the manner discussed in more detail herein. The growth device 1000, when in the implantation state, can have a predetermined initial size, shape, diameter, cross-section or other dimension. Exemplary initial dimensions of the growth device 1000 can include, but are not limited to, an initial dimension between one millimeter and four millimeters. The growth device 1000, for example, can be crimped on a delivery catheter system 2000 (shown in FIGS. 14A-D) at a size that is small enough to pass through a vascular system 110 (shown in FIG. 8) of a patient 100 (shown in FIG. 8) to a selected implantation site 130 (or other area of interest) (shown in FIG. 8) within a selected vessel or other lumen 120 (shown in FIG. 8) of the patient 100. Upon reaching the selected implantation site 130, the growth device 1000 can be deployed for treating a general congenital illness of the patient 100.

The growth device 1000 of FIG. 8 is illustrated as being deployed in the Glenn position. Turning to FIG. 8, the growth device 1000 can be disposed in the superior vena cava (or SVC) 121 of the patient 100 via a delivery catheter system 2000 (shown in FIGS. 14A-D). The distal end region $1110_D$ of the device frame 1100 can extend from the superior vena cava 121 and into the pulmonary artery (or PA) 122. Stated somewhat differently, the distal end region $1110_D$ can span an intersection 121B between the superior vena cava 121 and the pulmonary artery 122. In selected embodiments, the intersection 121B can be surgically created and/or created via the growth device 1000. The intersection 121B can define a tissue opening for enabling the superior vena cava 121 to communicate with the pulmonary artery 122. The retention member(s) 1200 of the growth device 1000 can extend from the delivery catheter system 2000 and engage at least one interior vessel surface 122A of the pulmonary artery 122.

The growth device 1000 can be revealed by the delivery catheter system 2000 and prepared for expansion. A catheter expansion system, such as a balloon expansion system 2200 (shown in FIG. 14B), of the delivery catheter system 2000 can be disposed within the central axial channel 1150 of the device frame 1100. The catheter expansion system can inflate or otherwise increase in size to expand the device frame 1100 from the implantation state to a (stable) expanded state. In the expanded state, the device frame 1100 can engage at least one interior vessel surface 121A of the superior vena cava 121 and stretch tissue defining the tissue opening at the intersection 121B between the superior vena cava 121 and the pulmonary artery 122. The growth device 1000, when in the expanded state, can have a predetermined expanded size, shape, diameter, cross-section or other dimension. An exemplary expanded size, shape, diameter, cross-section or other dimension of the growth device 1000 in the expanded state can be between ten millimeters and thirty millimeters, without limitation.

Once the device frame 1100 is expanded into the expanded state, the catheter expansion system can deflate or otherwise decrease in size, and the delivery catheter system 2000 can be withdrawn from the patient 100. The growth device 1000 in the expanded state can continue to engage the interior vessel surface 121A of the superior vena cava 121 and can contain sufficient radial strength to maintain the expanded state without support from the catheter expansion system. The growth device 1000 in the expanded state as shown in FIG. 8 can enable blood to flow from the superior vena cava 121 into the pulmonary artery 122.

Advantageously, the covering member 1300 can radially seal the intersection 121B between the superior vena cava 121 and the pulmonary artery 122. The covering member 1300, in other words, can be configured to provide seal against the stretched tissue opening created between the superior vena cava 121 and the pulmonary artery 122. Additionally and/or alternatively, the covering member 1300 can provide a seal against the interior vessel surface 121A of the superior vena cava 121 to help ensure that all blood flow from the superior vena cava 121 can be directed into the pulmonary artery 122.

After implantation is complete, the growth device 1000 can be re-expanded to a second, third or other subsequent (stable) expanded state as the patient 100 grows. The growth device 1000, in other words, can be periodically re-expanded to conform with an increased size of the selected lumen 120 of the patient 100. If implanted in a pediatric patient, the growth device 1000 can be re-expanded to an increased that is suitable for an older child patient, a teenage patient and/or an adult patient as the patient grows. The growth device 1000, for example, can be initially expanded to a first expanded state of fourteen millimeters and then re-expanded to a second expanded state with a predetermined dimension of eighteen millimeters as the patient grows. The growth device 1000 later can be further re-expanded to a third expanded state with a predetermined dimension of twenty-two millimeters as the patient further grows. In other words the growth device 1000 can be periodically to the first expanded state, the second expanded state, the third expanded state, as so on, as the selected lumen 120 of the patient 100 increases in diameter.

The growth device 1000 can be re-expanded in any suitable manner. For example, the growth device 1000 can be re-expanded via introduction of a catheter expansion system in the manner analogous to the expansion of the growth device 100 during implantation. Additionally and/or alternatively, the growth device 1000 can comprise a self-growing growth device with the device frame 1100 formed, for example, from nitinol or another shape-changing material. The growth device 1000 in the re-expanded state can continue to engage the interior vessel surface 121A of the superior vena cava 121 and can contain sufficient radial strength to maintain the expanded state.

The growth device 1000, in selected embodiments, can provide a shunt from the inferior vena cava (or IVC) 124 to the pulmonary artery (or PA) 122 during a Fontan procedure. Additionally and/or alternatively, the growth device 1000 can provide a shunt from the superior vena cava (or SVC) 121 to the pulmonary artery 122 during a Glenn procedure.

The shunt, for example, can be created using a flexible stent graft to allow blood flow to travel from the inferior vena cava 124 to the pulmonary artery 122 or the superior vena cava 121 to the pulmonary artery 122. The shunt graft may have one or more retention features for anchoring the graft in the pulmonary artery 122, superior vena cava 121 and/or the inferior vena cava 124. The shunt advantageously can allow for a lumen to be created for directing blood flow. In selected embodiments, the shunt can be provided as a stent frame or other structure that is able to hold open vessels and other tissue areas for the movement of blood from one vessel to another. In some embodiments, the stent can hold vessel walls open to create a lumen connection between blood in different blood vessels. One or more portions of the device frame 1100, for example, may be attached to walls of vessels to support the lumen; whereas, other portions of the device frame 1100 may be disposed at a vessel crossing and hold open other tissue matter.

Figure 9:
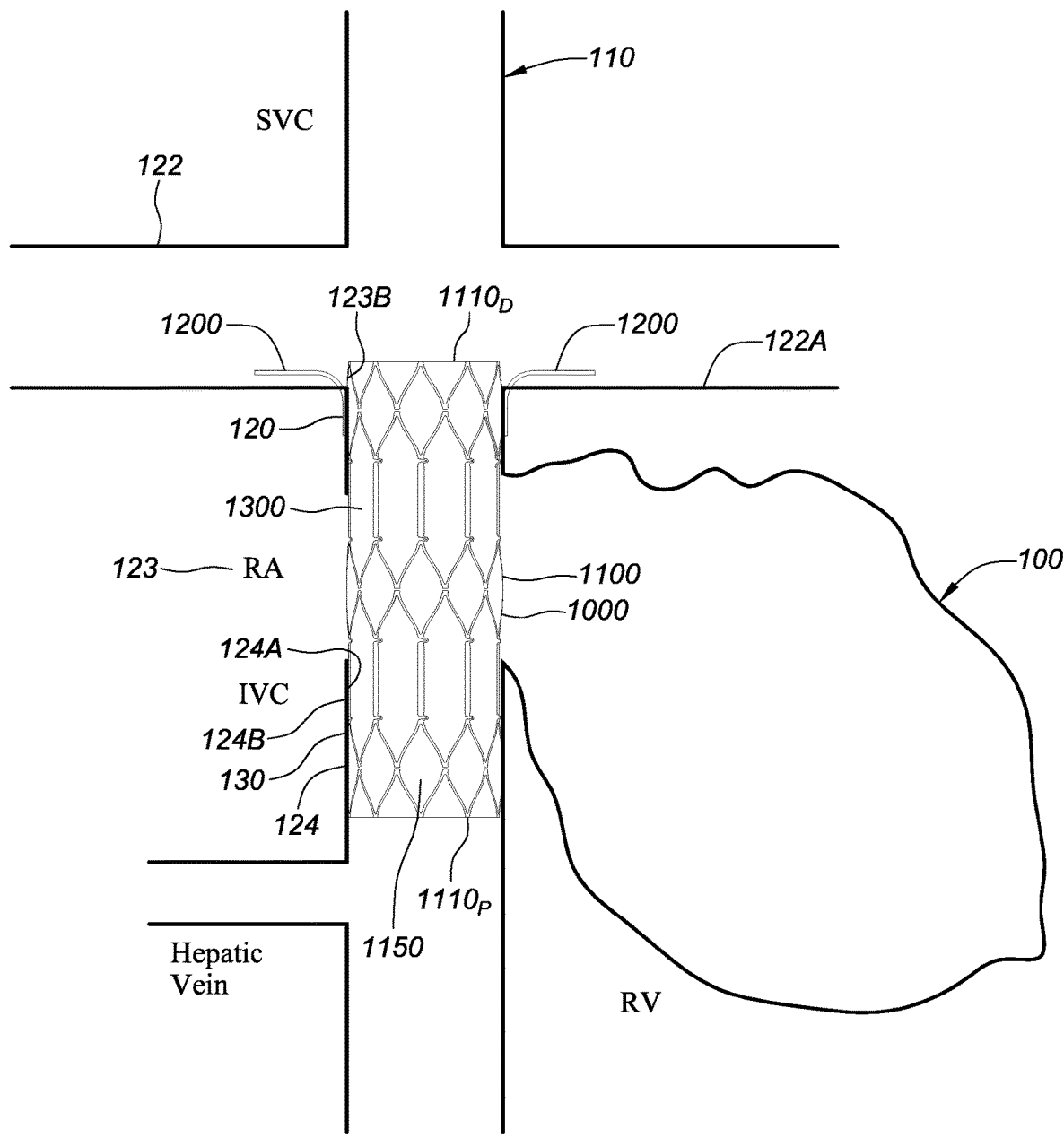
FIG. 9 is a detail drawing illustrating still another exemplary alternative embodiment of the growth device of FIG. 2, wherein the growth device is implanted in the Fontan position within the patient.

Turning to FIG. 9, the growth device 1000 is shown as being deployed in the Fontan position. The growth device 1000 can be disposed in tissue of the right atrium 123 of the patient 100 via a delivery catheter system 2000 (shown in FIGS. 14A-D). The distal end region 1110$_D$ of the device frame 1100 can extend from the tissue of the right atrium 123 and into the pulmonary artery 122. Stated somewhat differently, the distal end region 1110$_D$ can span a surgically-created intersection 123B between the right atrium 123 and the pulmonary artery 122. The intersection 123B can define a tissue opening for enabling the right atrium 123 to communicate with the pulmonary artery 122. The retention member(s) 1200 of the growth device 1000 can extend from the delivery catheter system 2000 and engage at least one interior vessel surface 122A of the pulmonary artery 122.

The proximal end region 1110$_P$ of the device frame 1100 can extend from the tissue of the right atrium 123 and into the inferior vena cava 124 of the patient 100 as illustrated in FIG. 9. An alignment of the growth device 1000 relative to a transition 124B between the right atrium 123 and the inferior vena cava 124 can be confirmed. The growth device 1000 can be revealed by the delivery catheter system 2000 and prepared for expansion. A catheter expansion system, such as a balloon expansion system 2200 (shown in FIG. 14B), of the delivery catheter system 2000 can be disposed within the central axial channel 1150 of the device frame 1100. The catheter expansion system can inflate or otherwise increase in size to expand the device frame 1100 from the implantation state to an expanded state.

In the expanded state, the device frame 1100 can engage at least one interior surface 123A (shown in FIG. 10A) of the right atrium 123 and/or at least one interior vessel surface 124A of the inferior vena cava 124. The expanded device frame 1100 can stretch tissue defining the tissue opening at the intersection 123B between the right atrium 123 and the pulmonary artery 122 and/or tissue defining the transition 124B between the right atrium 123 and the inferior vena cava 124. The growth device 1000, when in the expanded state, can have a predetermined expanded size, shape, diameter, cross-section or other dimension. An exemplary expanded size, shape, diameter, cross-section or other dimension of the growth device 1000 in the expanded state can be between ten millimeters and thirty millimeters, without limitation.

Once the device frame 1100 is expanded into the expanded state, the catheter expansion system can deflate or otherwise decrease in size, and the delivery catheter system 2000 (shown in FIGS. 14A-D) can be withdrawn from the patient 100. The growth device 1000 in the expanded state can continue to engage the interior surface 123A of the right atrium 123 and/or the interior vessel surface 124A of the inferior vena cava 124 and can contain sufficient radial strength to maintain the expanded state without support from the catheter expansion system. The covering member 1300 advantageously can radially seal the intersection 123B between the right atrium 123 and the pulmonary artery 122. The covering member 1300, in other words, can seal against the stretched tissue opening created between the right atrium 123 and the pulmonary artery 122. Additionally and/or alternatively, the covering member 1300 can provide a seal at the transition 124B between the right atrium 123 and the inferior vena cava 124 and thereby help to direct blood flow through the transition 124B.

After implantation is complete, the growth device 1000 can be re-expanded to a second, third or other subsequent stable re-expanded state as the patient 100 grows. The growth device 1000, in other words, can be periodically re-expanded to conform with an increased size of the selected lumen 120 of the patient 100. The growth device 1000 can be re-expanded in any suitable manner. For example, the growth device 1000 can be re-expanded via introduction of a catheter expansion system in the manner analogous to the expansion of the growth device 100 during implantation. Additionally and/or alternatively, the growth device 1000 can comprise a self-growing growth device with the device frame 1100 formed, for example, from nitinol or another shape-changing material. The growth device 1000 in the re-expanded state can continue to engage the interior surface 123A of the right atrium 123 and/or the interior vessel surface 124A of the inferior vena cava 124 and can contain sufficient radial strength to maintain the re-expanded state.

Two or more growth devices 1000 can be configured for implantation in the patient 100. The growth devices 1000, in selected embodiments, can comprise nested or telescoping growth devices. The growth devices 1000 advantageously can cooperate for treating general congenital illnesses in heart disease patients.

In selected embodiments, two separate growth devices 1000 can interlock to direct blood flow from the inferior vena cava 124 to the pulmonary artery 122. One of the growth devices 1000 can be placed into the inferior vena cava 124 and may extend into the right atrium 123. Retention anchors can attach to surrounding vessels and/or an interior vessel surface 124A of the inferior vena cava 124. A sealing mechanism can be located between a transition between the right atrium 123 and a hepatic vein 125 in the inferior vena cava 124. The growth device 1000 may be fully covered or partially covered by a covering member 1300. The other growth device 1000 may be placed in the pulmonary artery 122 and can extend into the right atrium 123. This growth device 1000 can have retention anchors in the pulmonary artery 122 that retain the growth device 1000 in the pulmonary artery 122.

In this embodiment, the growth device 1000 located in the inferior vena cava 124 can mate with the growth device 1000 anchored in the pulmonary artery 122 either externally or internally through radial expansion or a separate mechanism. Both growth devices 1000 can be deployed at lengths and may telescope or overlap within one another to allow for treatment of variable patient anatomical sizes. The separate growth device 1000 may allow for a greater range of patient sizing as the amount of overlap can be varied. Advantageously, the overlapping feature of the growth device 1000 likewise can be applied to the Glenn procedure as well with the retention anchors resting in the pulmonary artery 122.

Figure 10A:
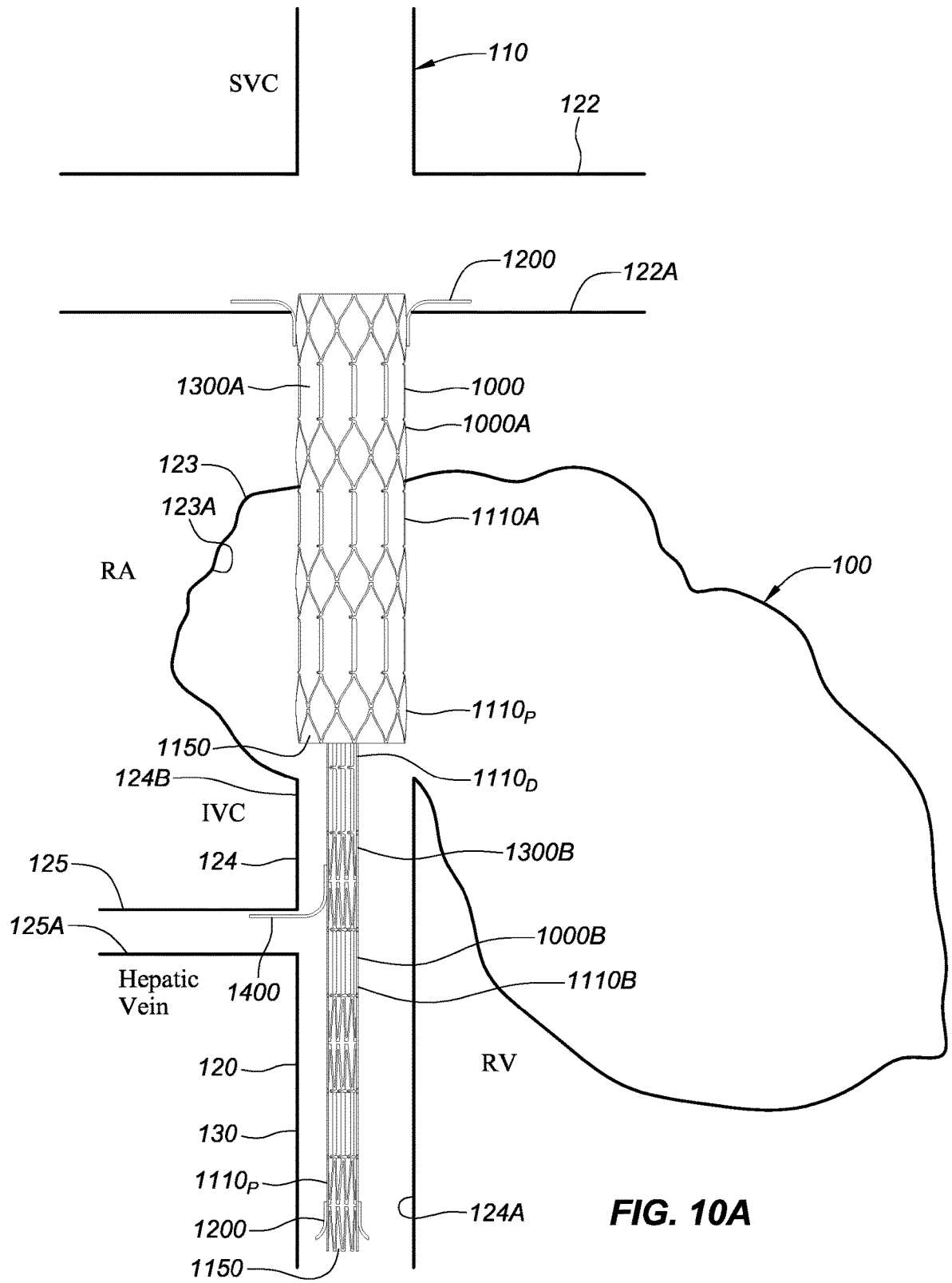
FIGS. 10A-B are detail drawings illustrating an exemplary alternative embodiment of the growth device of FIG. 9, wherein the growth device cooperates with a second growth device.
Figure 10B:
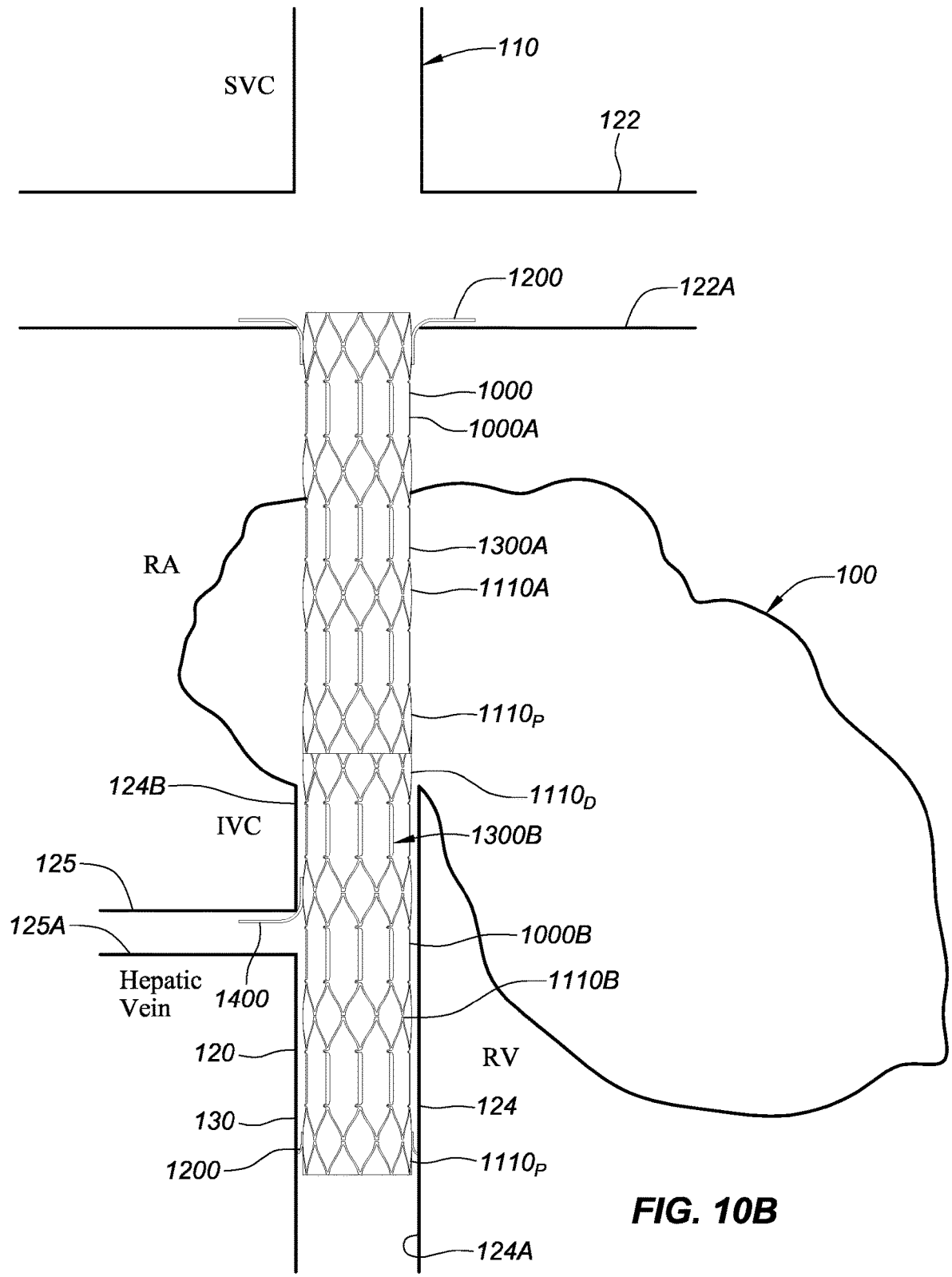

As shown in FIGS. 10A-B, for example, a first growth device 1000A can comprise a growth device 1000 having a first device frame 1110A with proximal and distal end regions $1110_P$, $1110_D$ and a first covering member 1300A. The first growth device 1000A is illustrated as having at least one retention member 1200 and being deployed in the Fontan position in the manner discussed in more detail above with reference to FIG. 9. A second growth device 1000B likewise can be configured for implantation in the patient 100. The second growth device 1000B can comprise a growth device 1000 having a second device frame 1110B with proximal and distal end regions $1110_P$, $1110_D$ and a second covering member 1300B. As illustrated in FIGS. 10A-B, one or more anchor members 1400 can be disposed on the second device frame 1110B.

If implanted in the patient 100 after the first growth device 1000A has been implanted, the second growth device 1000B can be disposed in the inferior vena cava 124 of the patient 100 as illustrated in FIG. 10A. The second growth device 1000B can extend through the inferior vena cava 124 and cooperate with the first growth device 1000A. With the second growth device 1000B being crimped to the implantation state, the distal end region $1110_D$ of the second growth device 1000B can be received within the central axial channel 1150 of the expanded first growth device 1000A. The second growth device 1000B can be radially aligned with the first growth device 1000A and can at least partially overlap with the first growth device 1000A. The first and second growth devices 1000A, 1000B thereby can form nested or telescoping growth devices.

The second growth device 1000B can extend from the proximal end region $1110_P$ of the first growth device 1000A and with the proximal end region $1110_P$ of the second growth device 1000B being positioned within the inferior vena cava 124 of the patient 100 as illustrated in FIG. 10A. The proximal end region $1110_P$ of the second growth device 1000B preferably is axially aligned with the inferior vena cava 124. As shown in FIG. 10A, a position of the second growth device 1000B can be adjusted until the proximal end region $1110_P$ of the second growth device 1000B is disposed adjacent to the transition 124B between the right atrium 123 and the inferior vena cava 124 and/or at least one anchor member 1400 of the second growth device 1000B is disposed adjacent to the hepatic vein 125 of the patient 100.

In selected embodiments, the proximal end region $1110_P$ of the second growth device 1000B can be axially aligned with the transition 124B; whereas, the anchor member 1400 of the second growth device 1000B can be configured to engage at least one interior vessel surface 125A of the hepatic vein 125. The proximal end region $1110_P$ of the second growth device 1000B, in other words, can be aligned with the hepatic vein 125 and the transition 124B. The engagement between the anchor member 1400 and the interior vessel surface 125A of the hepatic vein 125 can help ensure stability of the second growth device 1000B after deployment.

The second growth device 1000B can be revealed by a delivery catheter system 2000 (shown in FIGS. 14A-D) and prepared for expansion. A catheter expansion system, such as a balloon expansion system 2200 (shown in FIG. 14B), of the delivery catheter system 2000 can be disposed within the central axial channel 1150 of the second device frame 1100B. The catheter expansion system can inflate or otherwise increase in size to expand the second device frame 1100 from the implantation state to an expanded state.

In the expanded state, the second growth device 1000B can engage an interior surface of the proximal end region $1110_P$ of the first growth device 1000A and/or at least one interior vessel surface 124A of the inferior vena cava 124 as shown in FIG. 10B. The expanded second device frame 1100 can stretch tissue defining the transition 124B between the right atrium 123 and the inferior vena cava 124. The second growth device 1000B, when in the expanded state, can have a predetermined expanded size, shape, diameter, cross-section or other dimension. An exemplary expanded size, shape, diameter, cross-section or other dimension of the second growth device 1000B in the expanded state can be between ten millimeters and thirty millimeters, without limitation.

The anchor member 1400 of the second growth device 1000B can engage the interior vessel surface 125A of the hepatic vein 125. At least one retention member 1200 optionally can engage the interior vessel surface 124A of the inferior vena cava 124. The engagement by the anchor member 1400 and/or the retention member 1200 can help prevent migration of the second growth device 1000B.

Once the second device frame 1100B is expanded into the expanded state, the catheter expansion system can deflate or otherwise decrease in size, and the delivery catheter system 2000 can be withdrawn from the patient 100. The second growth device 1000B in the expanded state can continue to engage the interior surface of the proximal end region $1110_P$ of the first growth device 1000A and/or the interior vessel surface 124A of the inferior vena cava 124 and can contain sufficient radial strength to maintain the expanded state without support from the catheter expansion system.

The second covering member 1300 can be associated with a covered frame portion 1112 (shown in FIG. 11A) of the second device frame 1100B between the hepatic vein 125 and the transition 124B between the right atrium 123 and the inferior vena cava 124. In selected embodiments, the second covering member 1300B is associated only with the covered frame portion 1112 of the second device frame 1100B between the hepatic vein 125 and the transition 124B. The second covering member 1300B thereby can form a seal against stretched tissue between the hepatic vein 125 and the transition 124B.

After implantation is complete, the second growth device 1000B can be re-expanded to a second, third or other subsequent stable re-expanded state as the patient 100 grows. The second growth device 1000B, in other words, can be periodically re-expanded to conform with an increased size of the selected lumen 120 of the patient 100. The second growth device 1000B can be re-expanded in any suitable manner. For example, the second growth device 1000B can be re-expanded via introduction of a catheter expansion system in the manner analogous to the expansion of the growth device 100 during implantation. Additionally and/or alternatively, the second growth device 1000B can comprise a self-growing growth device with the second device frame 1100B formed, for example, from nitinol or another shape-changing material. The second growth device 1000B in the re-expanded state can continue to engage the interior surface of the proximal end region $1110_P$ of the first growth device 1000A and/or the interior vessel surface 124A of the inferior vena cava 124 and can contain sufficient radial strength to maintain the re-expanded state.

The nested or telescoping nature of the growth devices 1000 can enable precision locating for the second covering member 1300B of the second growth device 1000B. The second covering member 1300B advantageously can be precisely located regardless of variations in anatomy between patients 100. A covered end segment 1112A (shown in FIG. 11B) of the covered frame portion 1112 (shown in FIGS. 11A-B) of the second growth device 1000B can extend from the proximal end region $1110_P$ of the first growth device 1000A. In selected embodiments, the covered end segment 1112A of the second growth device 1000B can be configured to seal only the tissue between the hepatic vein 125 and the transition 124B between the right atrium 123 and the inferior vena cava 124 in selected embodiments. Since a distance between the hepatic vein 125 and the transition 124B can vary among patients, the nested growth devices 1000A, 1000B advantageously can be configured to precisely adjust a segment extension distance $D_E$ (shown in FIG. 11B) by which the covered end segment 1112A of the second growth device 1000B extends from the proximal end region $1110_P$ of the first growth device 1000A.

Figure 11A:
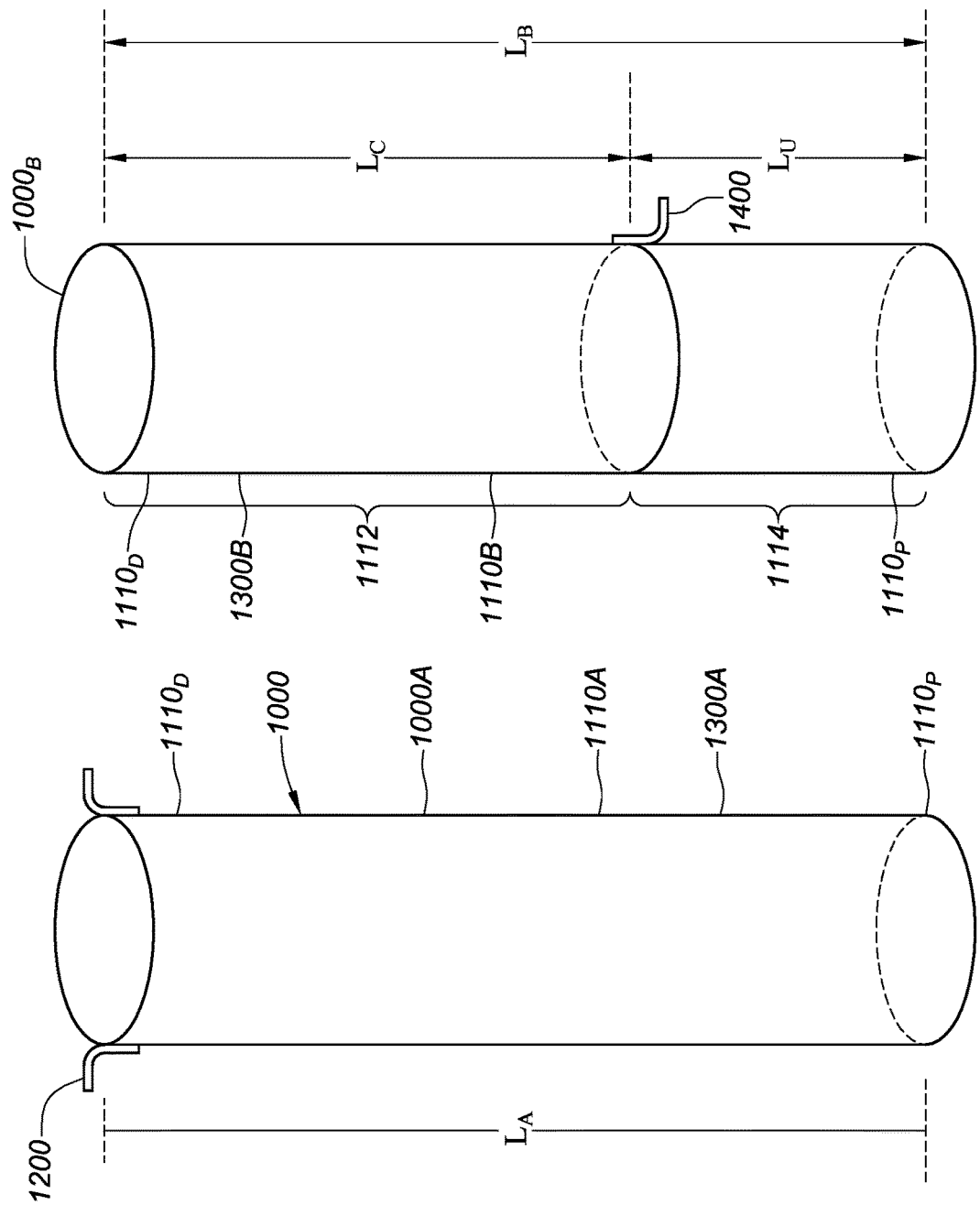
FIG. 11A is a top-level drawing illustrating an exemplary alternative embodiment of the growth devices of FIGS. 10A-B, wherein the growth devices comprise separate growth devices.

Turning to FIG. 11A, the first growth device 1000A is shown as comprising a first device frame 1100A with a first predetermined length $L_A$ between the proximal end region $1110_P$ and the distal end region $1110_D$ of the device frame 1110. In selected embodiments, the first predetermined length $L_A$ can comprise a distance between the retention member 1200 and the distal end region $1110_D$ of the first device frame 1110A. The first covering member 1300A can span from the proximal end region $1110_P$ to the distal end region $1110_D$ of the first device frame 1110A as shown in FIG. 11A.

The second growth device 1000B similarly can comprise a second device frame 1100B with a second predetermined length $L_B$ between the proximal end region $1110_P$ and the distal end region $1110_D$ of the second device frame 1100B. A second covering member 1300B can be associated with a covered frame portion 1112 of the second device frame 1100B. The covered frame portion 1112 of the second growth device 1000B can have a predetermined covered frame portion length $L_C$ that, in selected embodiments, can comprise a distance between the distal end region $1110_D$ of the second growth device 1000B and the anchor member 1400. The remainder of the second growth device 1000B can have a predetermined uncovered frame portion length Lu and preferably comprises an uncovered frame portion 1114 of the second growth device 1000B. In other words, the uncovered frame portion 1114 of the second growth device 1000B preferably is not covered by the covering member 1300.

Figure 11B:
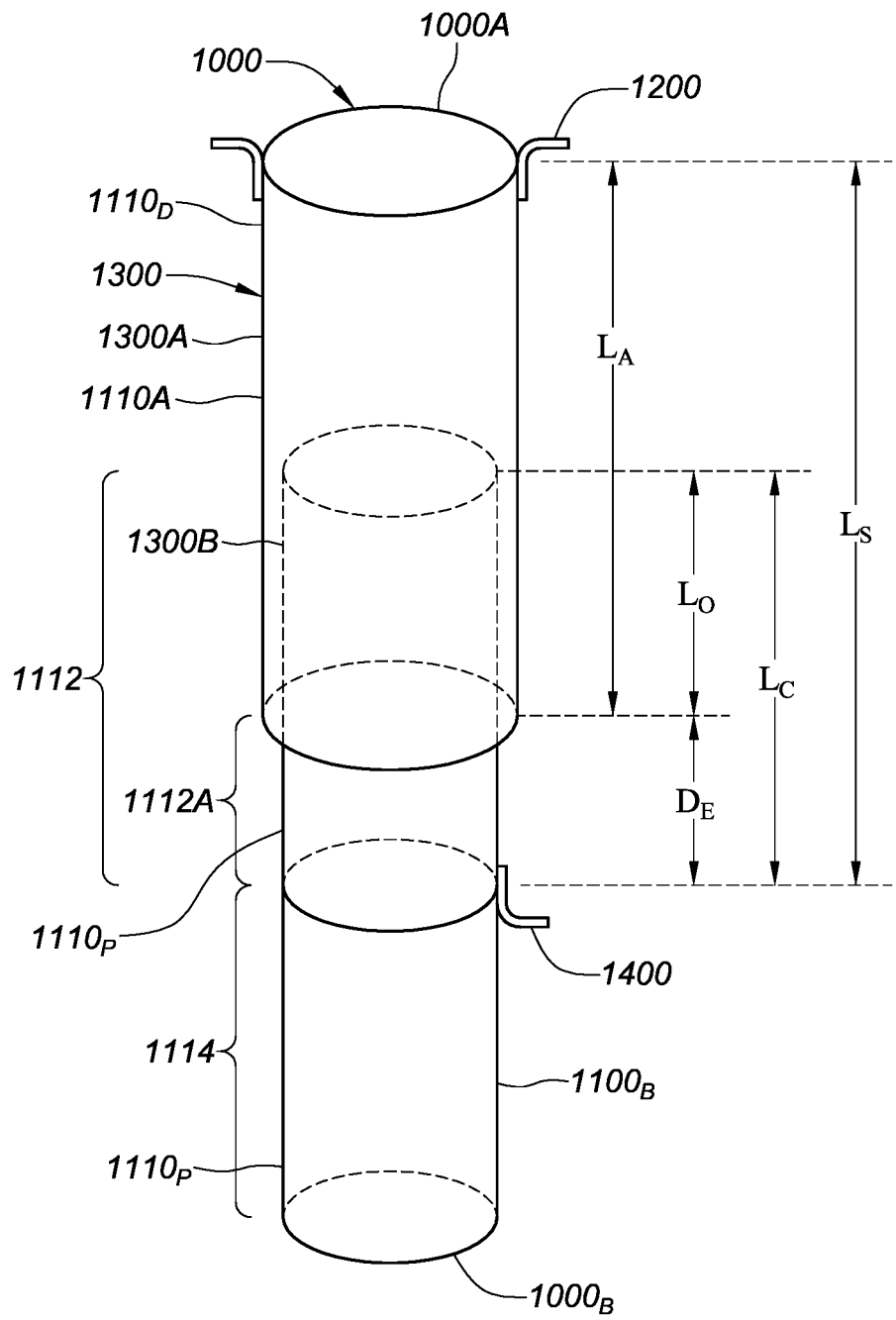
FIG. 11B is a top-level drawing illustrating an exemplary alternative embodiment of the growth devices of FIG. 11A, wherein the growth devices comprise nested growth devices.

When the first and second growth devices 1000A, 1000B are nested and configured to telescope, the second covering member 1300B can overlap or otherwise cooperate with the first covering member 1300A. In other words, the second covering member 1300B can supplement the first covering member 1300A to form a composite covering member. The composite covering member can have a predetermined composite covering member length Ls. As shown in FIG. 11B, the composite covering member length Ls can comprise a sum of the first predetermined length $L_A$ of the first growth device 1000A and the segment extension distance $D_E$ by which the covered end segment 1112A of the second growth device 1000B extends from the proximal end region $1110_P$ of the first growth device 1000A. An overlap length Lo between the nested first and second growth devices 1000A, 1000B can comprise a difference between the covered frame portion length $L_C$ of the covered frame portion 1112 and the segment extension distance $D_E$ of the covered end segment 1112A of the second growth device 1000B.

The composite covering member length Ls of the composite covering member advantageously can be adjusted to accommodate variations in patient anatomy. Stated somewhat differently, the segment extension distance $D_E$ by which the covered end segment 1112A of the second growth device 1000B extends from the proximal end region $1110_P$ of the first growth device 1000A can be adjusted based upon an anatomy of a specific patient. The covered end segment 1112A of the second growth device 1000B, for example, can be configured to seal the tissue between the hepatic vein 125 (shown in FIGS. 10A-B) and the transition 124B (shown in FIGS. 10A-B) between the inferior vena cava 124 and the right atrium 123 of a heart of a selected patient 100. A spacing between the hepatic vein 125 and the transition 124B can vary among patients 100. The segment extension distance $D_E$ by which the covered end segment 1112A of the second growth device 1000B extends from the proximal end region $1110_P$ of the first growth device 1000A can be increased and/or decreased to match the spacing between the hepatic vein 125 and the transition 124B for a specific patient 100.

The first and second growth devices can be implanted in a selected patient 100. The distal end region $1110_D$ and/or the retention member 1200 of the first growth device 1000A can be configured to engage the interior vessel surface 122A (shown in FIGS. 10A-B) of the pulmonary artery 122 (shown in FIGS. 10A-B). In the manner discussed in more detail above with reference to FIGS. 10A-B, the anchor member 1400 of the second growth device 1000B can be configured to engage the interior vessel surface 125A (shown in FIGS. 10A-B) of the hepatic vein 125 (shown in FIGS. 10A-B). The composite covering member length Ls of the nested growth devices 1000A, 1000B therefore can comprise a distance between the pulmonary artery 122 and the hepatic vein 125 of a patient 100. Since the distance between the pulmonary artery 122 and the hepatic vein 125 can vary from patient to patient, the composite covering member length Ls of the nested growth devices 1000A, 1000B advantageously can be adjusted to accommodate these variations.

Turning to FIG. 11B, the second growth device 1000B is shown as being received within the first growth device 1000A to form a nested (or telescoping) growth device arrangement. The second growth device 1000B is shown as being retracted or otherwise disposed within the first growth device 1000A by a first predetermined overlap distance $L_{O1}$. Stated somewhat differently, the first predetermined overlap distance $L_{O1}$ can comprise a distance by which the covered frame portion 1112 of the second growth device 1000B is disposed within the first growth device 1000A. The covered frame portion 1112 of the second growth device 1000B therefore can extend from the proximal end region $1110_P$ of the first growth device 1000A by a segment extension distance $D_E$.

As shown in FIG. 11B, the segment extension distance $D_E$ can comprise a difference between the predetermined covered frame portion length $L_C$ of the covered frame portion 1112 of the second growth device 1000B and the first predetermined overlap distance $L_{O1}$. An overall length $L_T$ of the nested growth devices 1000A, 1000B thus can comprise a sum of the segment extension distance $D_E$ and the first predetermined length $L_A$ of the first growth device 1000A as illustrated in FIG. 11B. If the anchor members 1400 of the second growth device 1000B is disposed at an intersection between the covered frame portion 1112 and the uncovered frame portion 1114 of the second growth device 1000B as shown in FIGS. 11A-B, for instance, the segment extension distance $D_E$ can be determined based at least in part upon a location of the hepatic vein 125 (shown in FIGS. 10A-B) in the patient 100 (shown in FIGS. 10A-B). In other words, the overall length $L_T$ of the nested growth devices 1000A, 1000B can comprise a sum of a first distance between the pulmonary artery 122 (shown in FIGS. 10A-B) and the inferior vena cava 124 (shown in FIGS. 10A-B) and a second distance between the hepatic vein 125 and the transition 124B (shown in FIGS. 10A-B) between the right atrium 123 (shown in FIGS. 10A-B) and the inferior vena cava 124 (shown in FIGS. 10A-B).

Numerical examples for illustrating exemplary manners for adjusting the nested growth devices 1000A, 1000B for implantation in specific patients are shown and described with reference to FIGS. 12A-B. Turning to FIG. 12A, the first growth device 1000A can have a first predetermined length $L_A$ of forty millimeters. The second growth device 1000B likewise can have a second predetermined length $L_B$ of sixty millimeters that includes a covered frame portion 1112 with a covered frame portion length $L_C$ of forty millimeters and an uncovered frame portion 1114 with an uncovered frame portion length Lu of twenty millimeters.

The nested growth devices 1000A, 1000B can be configured for implantation in a first patient who has a first distance of sixty millimeters between the pulmonary artery 122 (shown in FIGS. 10A-B) and the inferior vena cava 124 (shown in FIGS. 10A-B) and a second distance of ten millimeters between the hepatic vein 125 (shown in FIGS. 10A-B) and the transition 124B (shown in FIGS. 10A-B) between the right atrium 123 (shown in FIGS. 10A-B) and the inferior vena cava 124 (shown in FIGS. 10A-B). Since the anchor member 1400 of the second growth device 1000B is disposed at the intersection between the covered frame portion 1112 and the uncovered frame portion 1114 of the second growth device 1000B, the overall length $L_T$ of the nested growth devices 1000A, 1000B can comprise a sum of the first distance between the pulmonary artery 122 and the inferior vena cava 124 of sixty millimeters and the second distance between the hepatic vein 125 and the transition 124B of ten millimeters. The overall length $L_T$ of the nested growth devices 1000A, 1000B thus can comprise a length of seventy millimeters for the first patient.

The segment extension distance $D_E$ can comprise a difference of the overall length $L_T$ of seventy millimeters and the first predetermined length $L_A$ of the first growth device 1000A of forty millimeters and can be equal to thirty millimeters. Since the covered frame portion 1112 has a covered frame portion length $L_C$ of forty millimeters and extends from the proximal end region $1110_P$ of the first growth device 1000A by the segment extension distance $D_E$ of thirty millimeters, the overlap length Lo can comprise a difference between the covered frame portion length $L_C$ and the segment extension distance $D_E$, or ten millimeters.

The same nested growth devices 1000A, 1000B advantageously can be configured for implantation in a second patient as shown in FIG. 12B. The second patient can have a first distance of forty millimeters between the pulmonary artery 122 (shown in FIGS. 10A-B) and the inferior vena cava 124 (shown in FIGS. 10A-B) and a second distance of ten millimeters between the hepatic vein 125 (shown in FIGS. 10A-B) and the transition 124B (shown in FIGS. 10A-B) between the right atrium 123 (shown in FIGS. 10A-B) and the inferior vena cava 124 (shown in FIGS. 10A-B). In the manner discussed above with reference to the overall length $L_T$ of FIG. 12A, the overall length $L_T$ of the nested growth devices 1000A, 1000B for the second patient can comprise a sum of the first distance between the pulmonary artery 122 and the inferior vena cava 124 of forty millimeters and the second distance between the hepatic vein 125 and the transition 124B of ten millimeters. The overall length $L_T$ for the second patient thus can be equal to fifty millimeters.

The segment extension distance $D_E$ can comprise a difference of the overall length $L_T$ of fifty millimeters and the first predetermined length $L_A$ of the first growth device 1000A of forty millimeters and can be equal to ten millimeters for the second patient. Since the covered frame portion 1112 has a covered frame portion length $L_C$ of forty millimeters and extends from the proximal end region $1110_P$ of the first growth device 1000A by the segment extension distance $D_E$ of ten millimeters, the overlap length Lo can comprise a difference between the covered frame portion length $L_C$ and the segment extension distance $D_E$, or thirty millimeters.

Figure 13:
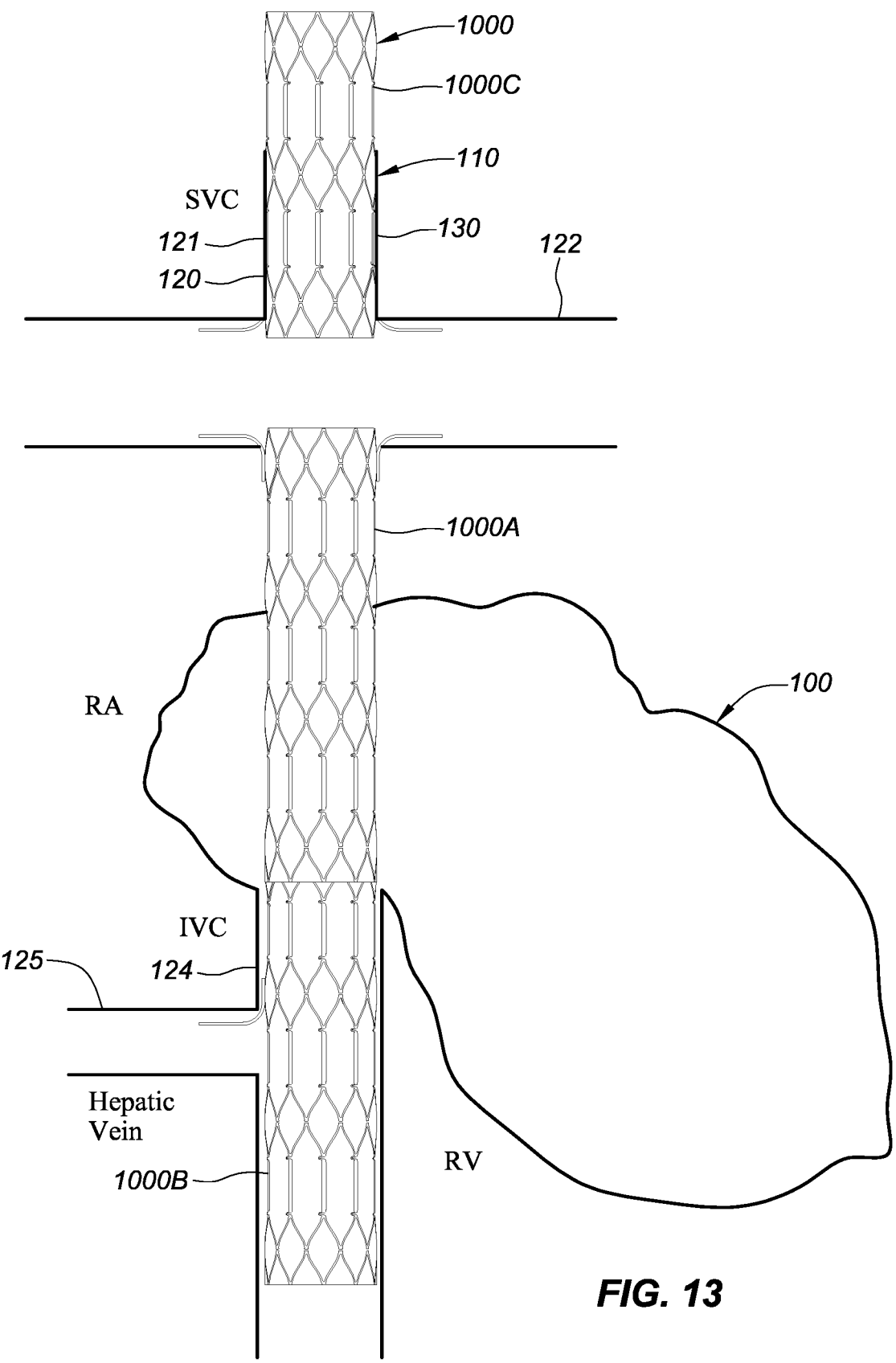
FIG. 13 is a top-level drawing illustrating an exemplary alternative embodiment of the growth devices of FIGS. 10A-B, wherein the growth devices implanted in the Fontan position within the patient cooperate with a third growth device implanted in the Glenn position.

The growth devices 1000 advantageously can be configured in any suitable number and/or arrangement for implantation in the patient 100. Turning to FIG. 13, for example, three growth devices 1000 are shown as being implanted in the patient 100. A first growth device 1000A and a second growth device 1000B can be configured as nested (or telescoping) growth devices and deployed in the Fontan position in the manner discussed in more detail above with reference to FIGS. 9 and 10A-B. In addition, a third growth device 1000C can be implanted in the Glenn position as shown and described herein with reference to FIG. 8.

In the manner discussed herein, the growth device 1000 can be implanted and deployed at a selected implantation site 130 (or other area of interest) (shown in FIG. 8) within a selected vessel or other lumen 120 (shown in FIG. 8) of the patient 100 (shown in FIG. 8) via a delivery catheter system 2000. An exemplary delivery catheter system 2000 for implanting the nested growth devices 1000A, 1000B (shown in FIGS. 10A-B) is illustrated in FIGS. 14A-D. The delivery catheter system 2000 of FIGS. 14A-D can comprise a dual balloon catheter system for streamlining implantation and deployment of the nested growth devices 1000A, 1000B.

Figure 14A:
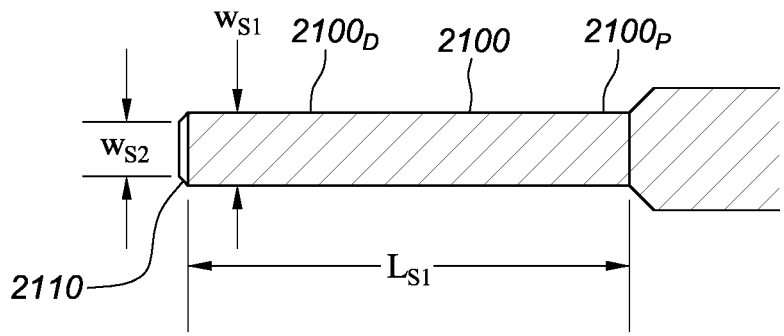
FIGS. 14A-D are detail drawings illustrating an exemplary embodiment of a delivery catheter system for implanting and deploying the growth device of FIG. 2 at a selected implantation site within the patient.

Turning to FIG. 14A, the delivery catheter system 2000 is shown as comprising a covered delivery catheter system that including an outer sheath member 2100. The outer sheath member 2100 can cover the first growth device 1000A (shown in FIG. 11A) and separate second growth device 1000B (shown in FIG. 11A). Once introduced into the patient 100 (shown in FIGS. 10A-B), the outer sheath member 2100 can steer and otherwise guide the first and second growth devices 1000A, 1000B through the vascular system of the patient 100 and to the selected implantation site 130 (or other area of interest) (shown in FIG. 8) within a selected vessel or other lumen 120 (shown in FIG. 8) of the patient 100.

Comprising an elongated sheath member with a predetermined length $L_{S1}$, the outer sheath member 2100 can have a proximal end region $2100_P$ and a distal end region $2100_D$ with a catheter insertion tip 2110. The catheter insertion tip 2110 preferably comprises a smooth tip for facilitating passage of the delivery catheter system 2000 through the vascular system of the patient 100. The distal end region $2100_D$ can have a first width $W_{S1}$; whereas, the catheter insertion tip 2110 can have a second width $W_{S2}$. An exemplary length $L_{S1}$ of the outer sheath member 2100 can comprise sixty-five centimeters, without limitation. In selected embodiments, the first width $W_{S1}$ of the distal end region $2100_D$ can comprise a width between ten and eleven French with the catheter insertion tip 2110 having second width $W_{S2}$ of nine French.

Figure 14B:
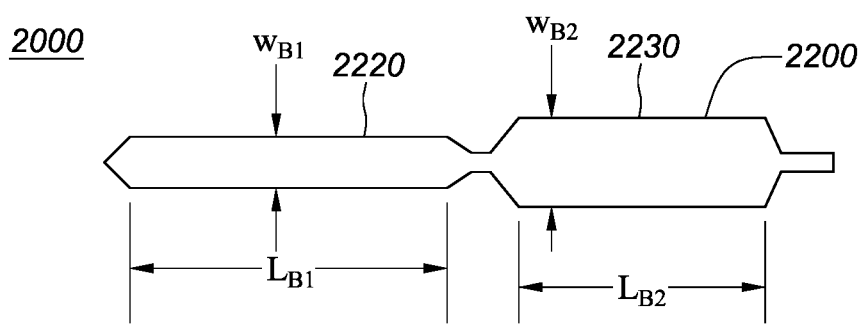
Figure 14C:
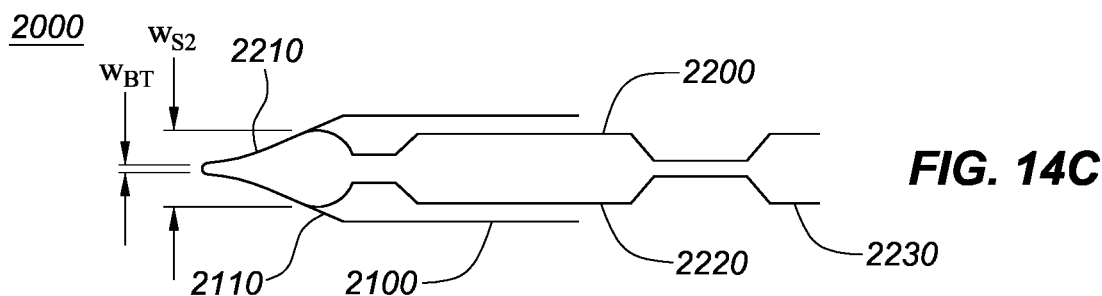

A balloon shaft member 2200 of the delivery catheter system 2000 is shown in FIGS. 14B-C. Turning to FIG. 14B, the balloon shaft member 2200 is shown as comprising a first balloon member 2220 that is disposed distally from a second balloon member 2230. The first balloon member 2220 can be configured to expand the first growth device 1000A (shown in FIG. 11A) at the selected implantation site 130 (or other area of interest) (shown in FIG. 8) within the patient 100 (shown in FIG. 8), and the second balloon member 2230 can be configured to expand the second growth device 1000B (shown in FIG. 11A) after the first growth device 1000A is expanded. The balloon shaft member 2200 advantageously can expand the first balloon member 2220 and the second balloon member 2230 in an independent manner for enable a staged procedural deployment of the first and second growth devices 1000A, 1000B.

In selected embodiments, the first balloon member 2220 can have a first balloon length $L_{B1}$ that can be the same as, or different from, a second balloon length $L_{B2}$ of the second balloon member 2230. The first balloon member 2220 likewise can expand to a first balloon width (or diameter) $W_{B1}$ that can be the same as, or different from, a second balloon width (or diameter) $W_{B2}$ to which the second balloon member 2230 can be expanded. Specific lengths and widths of the first and second balloon members 2220, 2230 can depend, for instance, upon an anatomy of the patient 100. As a nonlimiting example, the first balloon member 2220 can have a first balloon length $L_{B1}$ of about sixty millimeters and/or a first balloon width $W_{B1}$ of between ten and twelve millimeters. Additionally and/or alternatively, the second balloon member 2230 can have a second balloon length $L_{B2}$ of about seventy millimeters and/or a second balloon width $W_{B2}$ of between twelve and fourteen millimeters, without limitation.

Turning to FIG. 14C, the balloon shaft member 2200 is shown as being disposed within the outer sheath member 2100. The balloon shaft member 2200 can include a balloon catheter tip 2210. As shown in FIG. 14C, the balloon catheter tip 2210 can have a predetermined balloon tip width (or diameter) $W_{BT}$. Exemplary balloon tip widths $W_{BT}$ can include, but are not limited to, 0.018 inches. The balloon catheter tip 2210 preferably can mate with the catheter insertion tip 2110 (shown in FIG. 14A) of the outer sheath member 2100 (shown in FIG. 14A) to create a smooth transition for facilitating passage of the delivery catheter system 2000 through the vascular system of the patient 100. A self-expanding growth device 1000 can be delivered without the balloon shaft member 2200 or, if additional deployment force is needed, with the balloon shaft member 2200.

In some embodiments of the delivery catheter system 2000, the first balloon member 2220 can deploy the first growth device 1000A into the pulmonary artery 122 or other vessel, which can be followed by a second balloon member 2230 deploying the second growth device 1000B into the first growth device 1000A and the inferior vena cava 124 or the superior vena cava 121. In this embodiment, the first and second balloon members 2220, 2230 can have different lengths and diameters depending on the target anatomy. For example, if the pulmonary artery 122 of the patient 100 has a diameter that is smaller than a diameter of the inferior vena cava 124 or superior vena cava 121, the first balloon member 2220 can have a diameter that is smaller than a diameter of the second balloon member 2230. The first and second growth devices 1000A, 1000B can be deployed together using a single delivery system with one or more balloon members 2220, 2230 and/or can be deployed independently via separate delivery systems.

If deployed via the single delivery system, the first growth device 1000A can be uncovered and deployed with the second growth device 1000B remaining encapsulated further back within the delivery system. In this embodiment, after the first growth device 1000A is deployed, the delivery system can be advanced into the first growth device 1000A wherein the second growth device 1000B can be aligned and deployed into the first growth device 1000A as well as the inferior vena cava 124 or superior vena cava 121. Once the second growth device 1000B is deployed and in position, the balloon members 2220, 2230 can be removed by pulling the delivery system backwards out of the first and second growth devices 1000A, 1000B.

In some embodiments, the growth device 1000 can be deployed using a tapered balloon member. If the pulmonary artery 122 is smaller than the inferior vena cava 124 or superior vena cava 121, a portion of the tapered balloon member for deploying the first growth device 1000A into the pulmonary artery 122 can have a diameter that is smaller than a diameter of a portion of the tapered balloon member for deploying the second growth device 1000B into the inferior vena cava 124 or superior vena cava 121.

In some embodiments, the balloon shaft member 2200 can have one or more tapered components connected to the leading end region of the first balloon member 2220 and/or the second balloon member 2230 that can help decrease a likelihood of the first and second balloon members 2220, 2230 engaging the first and second growth devices 1000A, 1000B during removal of the delivery catheter system 2000. The tapered components can be larger in diameter than the deflated first and second balloon members 2220, 2230 such that the tapered elements can interact with the first and second growth devices 1000A, 1000B instead of the first and second balloon members 2220, 2230 interacting with the growth devices 1000A, 1000B.

Figure 14D:
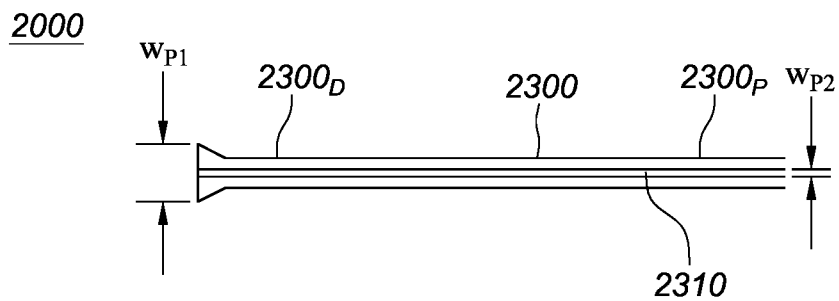

The delivery catheter system 2000 optionally can include a pusher shaft member 2300 as illustrated in FIG. 14D. The pusher shaft member 2300 advantageously can help stabilize the first and second growth devices 1000A, 1000B (shown in FIGS. 10A-B) during deployment. Stated somewhat differently, the pusher shaft member 2300 can help ensure that the first and second growth devices 1000A, 1000B remain axially centered relative to the first and second balloon members 2220, 2230 (shown in FIG. 14B), respectively, when the first and second growth devices 1000A, 1000B are loaded into the delivery catheter system 2000 and/or as the first and second growth devices 1000A, 1000B are implanted and deployed at the selected implantation site 130 (shown in FIG. 8) within the selected lumen 120 (shown in FIG. 8) of the patient 100 (shown in FIG. 8).

Turning to FIG. 14D, the pusher shaft member 2300 is shown as comprising an elongated member with a proximal end region 2300$_P$ and a distal end region 2300$_D$. The proximal end region 2300$_P$ of the pusher shaft member 2300 can have a first predetermined width (or diameter), and/or the distal end region 2300$_D$ region can have a second predetermined width (or diameter) $W_{P1}$. The second predetermined width (or diameter) $W_{P1}$ can comprise any suitable width (or diameter) and, in selected embodiments, can comprise a width (or diameter) of about eight French, without limitation.

The pusher shaft member 2300 can define an internal channel 2310. As shown in FIG. 14D, the internal channel 2310 can span between the proximal end region 2300$_P$ and a distal end region 2300$_D$ of the pusher shaft member 2300. The internal channel 2310 can have an internal width (or diameter) $W_{P2}$. In selected embodiments, the internal width $W_{P2}$ of the internal channel 2310 can be configured to receive the balloon shaft member 2200 (shown in FIGS. 14B-C). The internal width $W_{P2}$ of the internal channel 2310, in other words, can comprise a predetermined width (or diameter) that is greater than the first balloon width (or diameter) Wm (shown in FIGS. 14B-C) of the first balloon member 2220 (shown in FIGS. 14B-C) and/or can be greater than the second balloon width (or diameter) Wm (shown in FIGS. 14B-C) of the second balloon member 2230 (shown in FIGS. 14B-C).

Figure 14E:
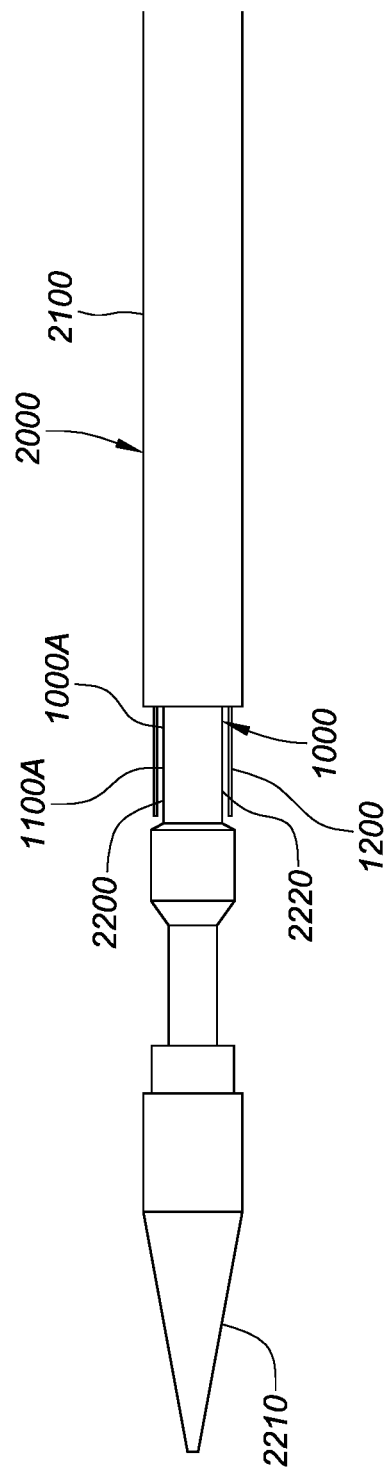
Figure 14G:
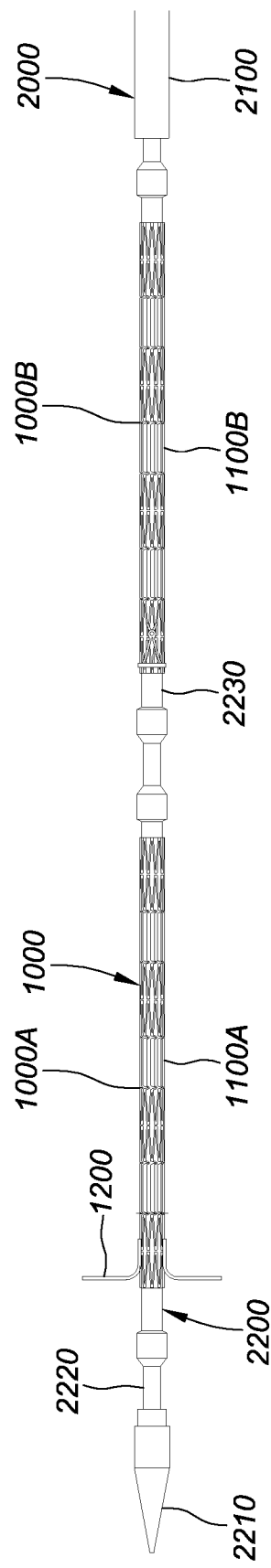
Figure 15A:
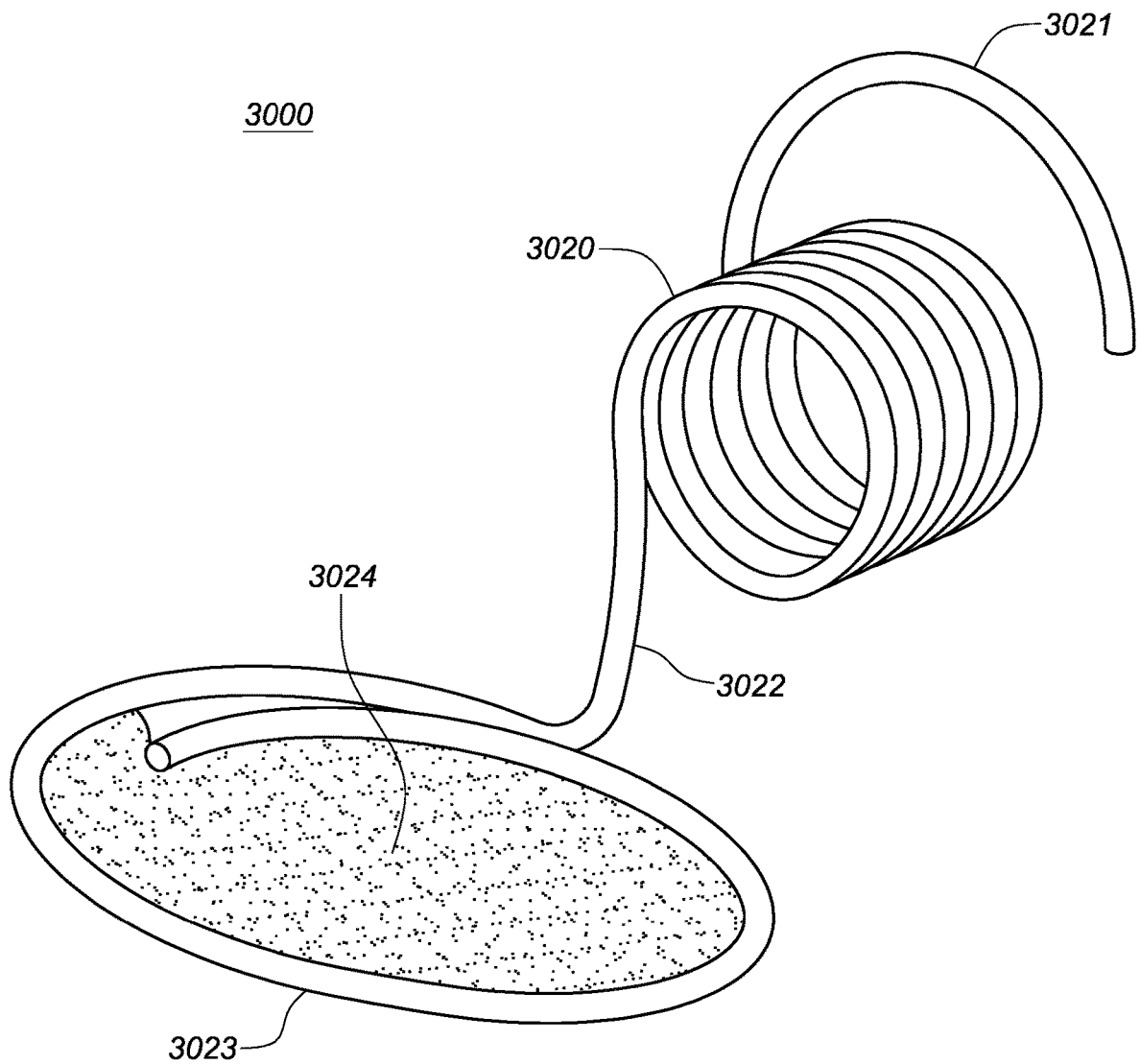
FIGS. 15A-E are detail drawings illustrating an exemplary embodiment of a transcatheter growth device, wherein the transcatheter growth device includes a wireframe-based shunt that has a coil device for docking into a superior vena cava (or SVC) of a patient.
Figure 15B:
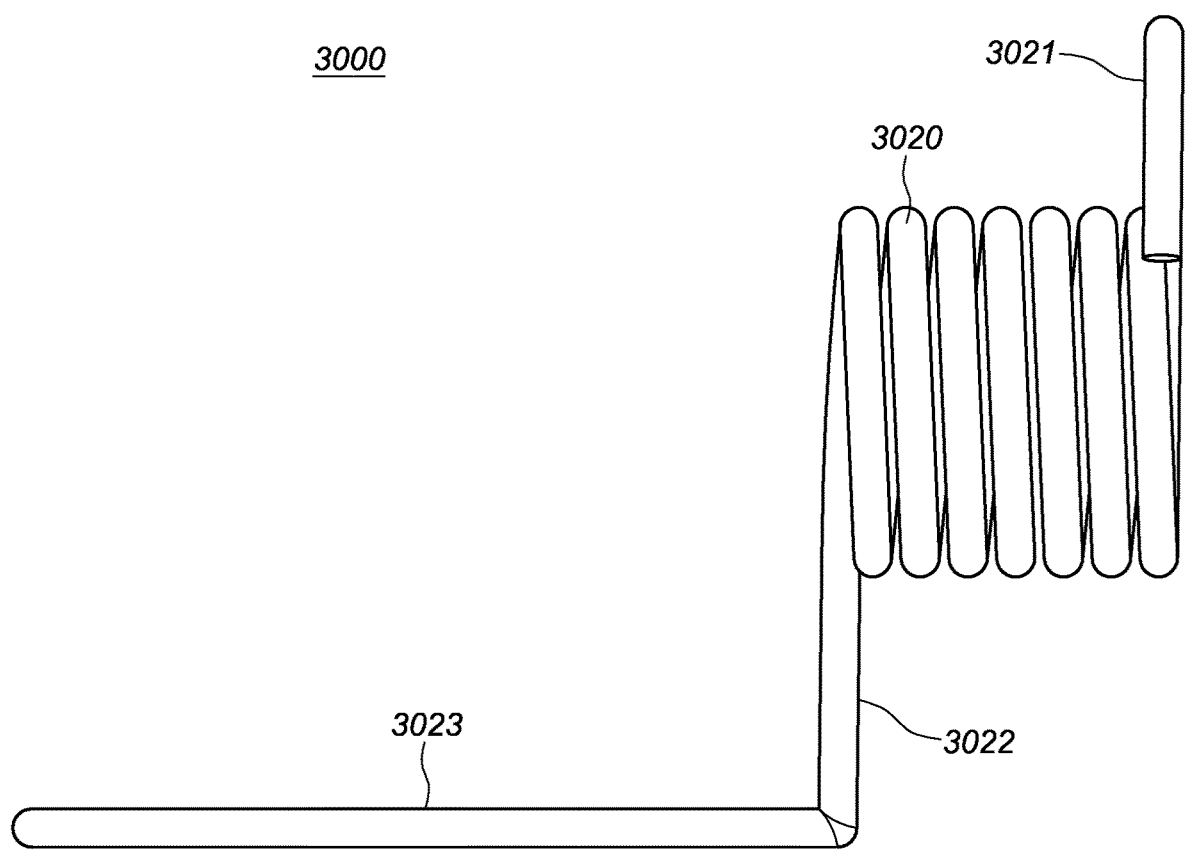
Figure 15C:
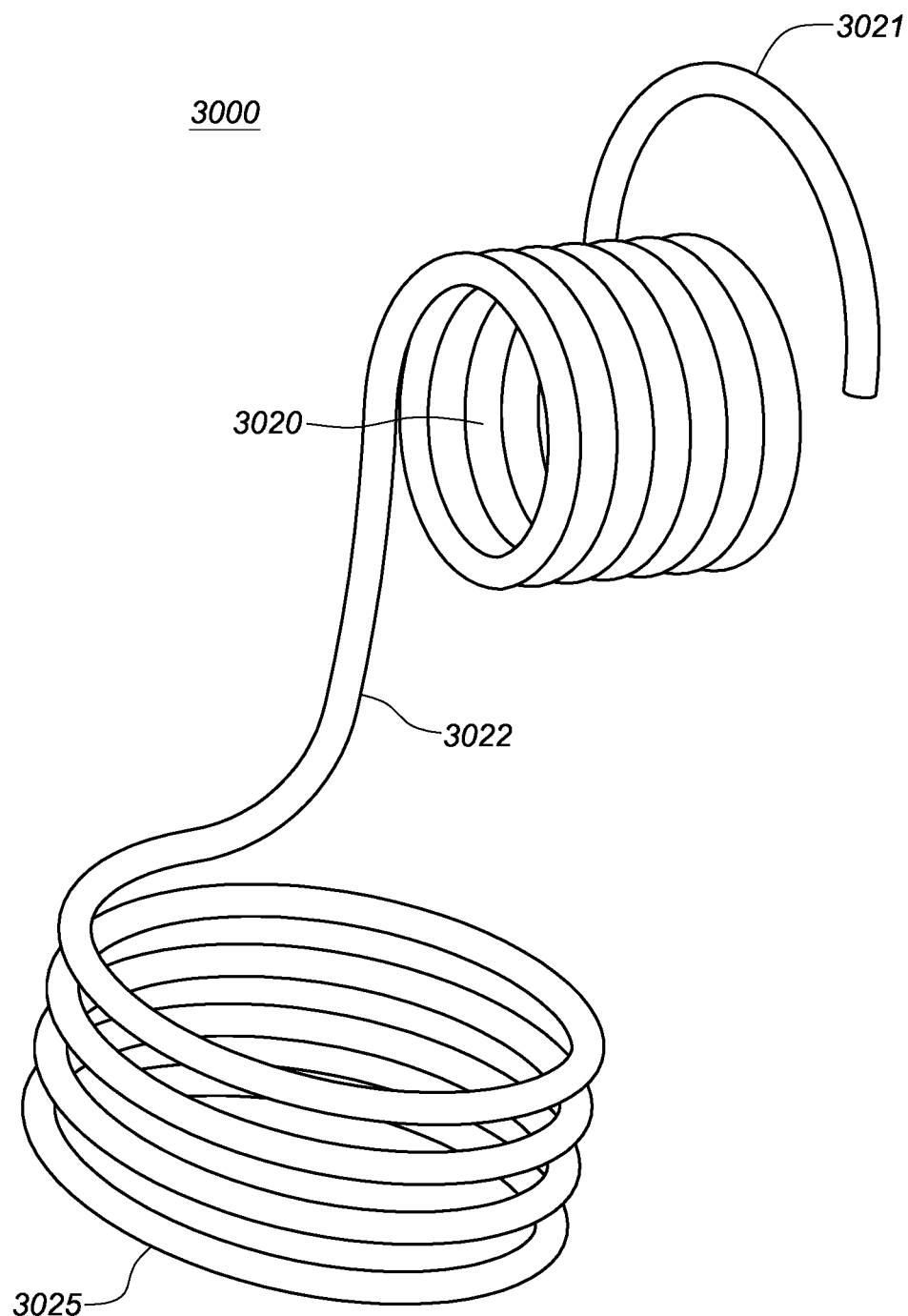
Figure 15D:
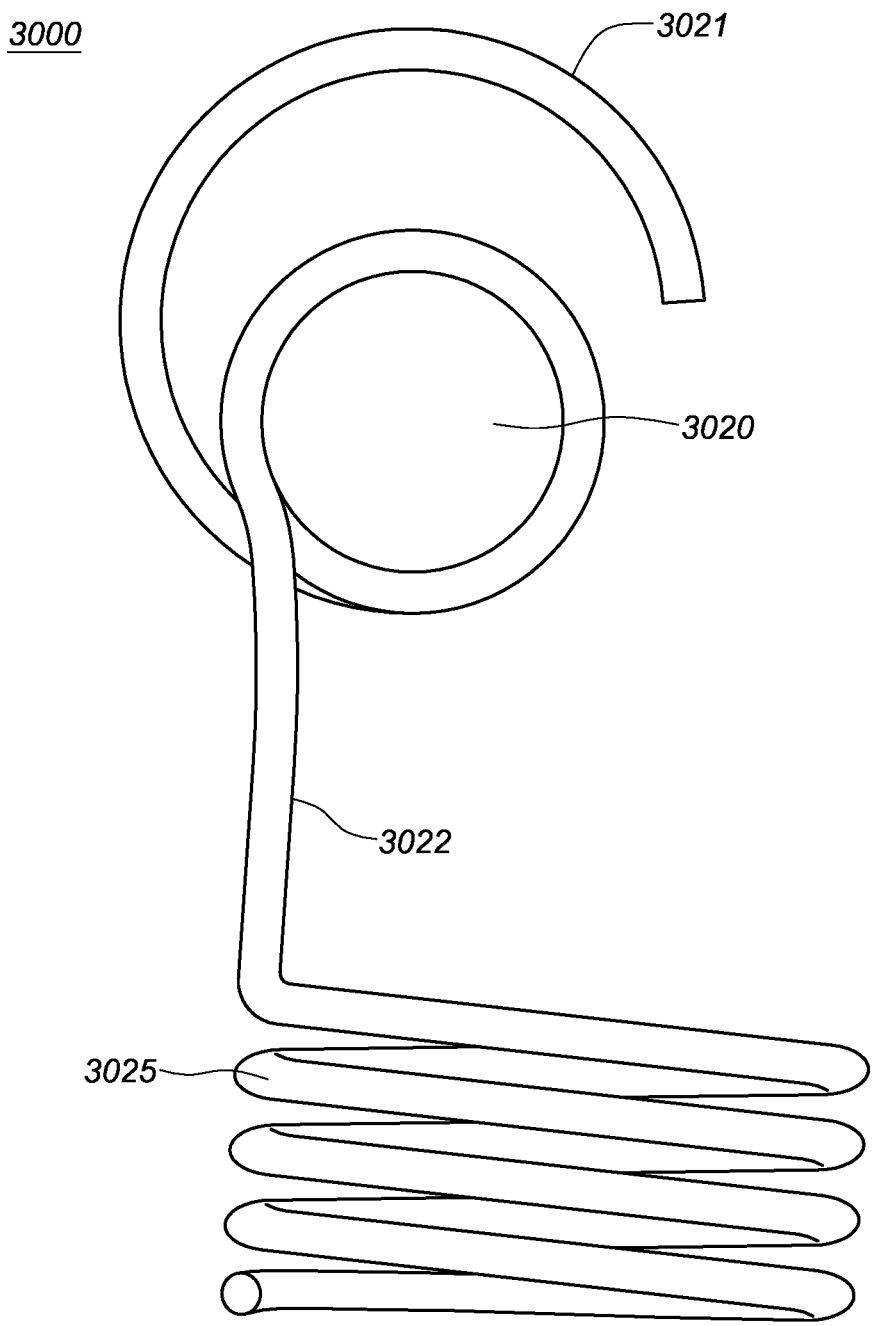
Figure 15E:
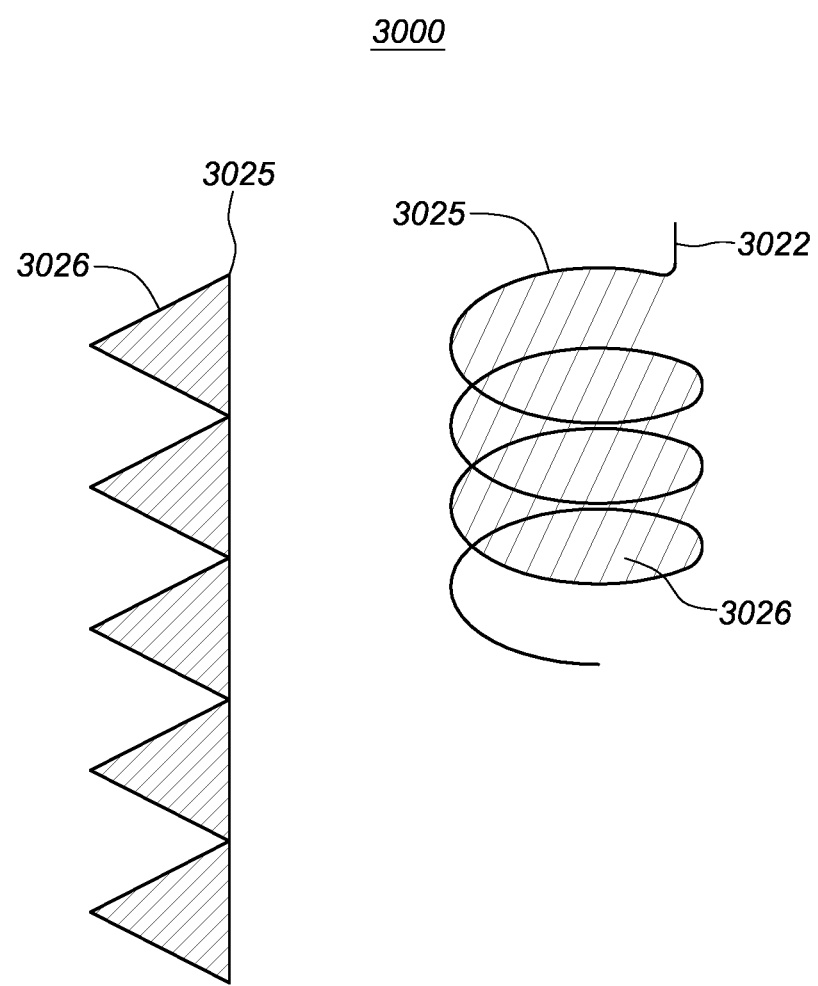

FIGS. 14E-G illustrate an exemplary embodiment of the delivery catheter system 2000 with the first and second growth devices 1000A, 1000B being disposed on the balloon expansion system 2200. Turning to FIG. 14E, for example, the outer sheath member 2100 of the delivery catheter system 2000 is shown as being distally retracted relative to the balloon catheter tip 2210 for partially exposing the first growth device 1000A during implantation. The first growth device 1000A can be disposed on the first balloon member 2220 in the manner discussed above with reference to FIGS. 14A-D. With the outer sheath member 2100 partially retracted, the retention member(s) 1200 of the first growth device 1000A can be partially revealed. The retention member(s) 1200 are illustrated as being a straight or other implantation state with the retention member(s) 1200 axially aligned with the first device frame 1100A for facilitating insertion into the selected vessel or other lumen 120 (shown in FIG. 8) of the patient 100 (shown in FIG. 8).

As the outer sheath member 2100 continues to retract, the retention member(s) 1200 of the first growth device 1000A can be fully revealed and permitted to deploy as shown in FIG. 14F. The retention member(s) 1200, in other words, can transition from the implantation state to a deployed state for engaging the selected vessel or other lumen 120 (shown in FIG. 8) of the patient 100 (shown in FIG. 8) in the manner discussed herein. The first growth device 1000A can be revealed, in its entirely with further retraction of the outer sheath member 2100. FIG. 14G illustrates that the second growth device 1000B can be disposed on the second balloon member 2230 in the manner discussed above with reference to FIGS. 14A-D and likewise can be revealed in its entirely via additional retraction of the outer sheath member 2100.

Once the first growth device 1000A is fully revealed, the first balloon member 2220 can inflate or otherwise increase in size to expand the first growth device 1000A from the implantation state to the (stable) expanded state in the manner discussed above with reference to FIGS. 14A-D. Additionally and/or alternatively, the second balloon member 2230 can inflate or otherwise increase in size to expand the second growth device 1000B from the implantation state to the (stable) expanded state. The first and second growth devices 1000A, 1000B can be expanded and otherwise deployed simultaneously and/or in any predetermined sequence.

In selected embodiments, the first growth device 1000A can be expanded before the second growth device 1000B is expanded. The first growth device 1000A, for example, can be expanded to the expanded state. The second growth device 1000B in the implantation state then can be disposed within the central axial channel 1150 (shown in FIG. 2) of the expanded first growth device 1000A as shown and described with reference to FIGS. 11B and 12A-B and expanded to the expanded state. The periphery 1140 (shown in FIG. 2) of the expanded second device frame 1100B thereby can engage the periphery 1140 of the expanded first device frame 1100A, deploying the first and second growth devices 1000A, 1000B in the nested or telescoping arrangement.

The second growth device 1000B alternatively can be expanded before the first growth device 1000A is expanded. The second growth device 1000B, for example, can be expanded to the expanded state. The first growth device 1000A in the implantation state then can be disposed within the central axial channel 1150 of the expanded second growth device 1000B as shown and described with reference to FIGS. 11B and 12A-B and expanded to the expanded state. The periphery 1140 of the expanded first device frame 1100A thereby can engage the periphery 1140 of the expanded second device frame 1100B, deploying the first and second growth devices 1000A, 1000B in the nested or telescoping arrangement.

In some embodiments, the growth device 1000 may be delivered on a catheter that is less than three millimeters in diameter, and expanded to a first expanded state that is equivalent to a vessel size of a congenital child. The growth device 1000 may be re-expandable as the patient grows to keep up with the somatic growth of the patient. For example, the growth device 1000 can be deployed to a diameter of twelve millimeters and can be re-expanded with vessel growth as the patient ages. The growth device 1000 can be initially deployed to an initial diameter ranging from four millimeters to twenty millimeters and can then be re-expanded to twenty-four millimeters, or larger, in diameter. The growth device 1000 may hold open various vessels to maintain an open lumen for blood flow as the patient grows. Some embodiments of the growth deice 1000 can have a covering member 1300 on an external surface of the device frame 1100 that seals against the vessel walls to prevent blood flow around the growth device 1000.

In some embodiments, the delivery catheter system 2000 can be composed of high-durometer materials that promote implant deployment stability, delivery system control and delivery system torque transfer.

Additional and/or alternative embodiments and/or features of the growth device 1000 are shown and described herein with reference to FIGS. 15-35. The growth device 1000, for example, can be provided as a shunt device and/or shunt graft.

In some embodiments of the Glenn and the Fontan shunt graft, the graft may be composed of a single stent scaffold with interconnected regions to promote stability and flexibility of the graft. These interconnected regions can have a suitable shape, such as a "V" or "C," and/or can have eliminated stent cell connections, or some other mechanical feature to promote flexibility of the shunt graft. The shunt graft scaffold can have straight vertical features or vertically connected apices that can reduce the amount of foreshortening as the shunt graft grows. In this embodiment, the shunt graft scaffold can be a single component that may span the entire length of the graft but can also span a portion of the graft. The shunt graft scaffold can be, but is not limited to, two millimeters to twenty-four millimeters or more in diameter. The shunt graft scaffold can be composed of, but is not limited to, cobalt chromium, nitinol, stainless steel, or other metal alloys. In some embodiments, the shunt graft scaffold can have retention features to encourage retention of anchoring mechanisms and the sealing mechanism. The retention features can be, but are not limited to, circular eyelets, rectangular tabs, stent struts, or some other mechanical lock. In some embodiments, the shunt graft scaffold can be made of thicker or thinner material to promote or restrict the amount that the shunt graft recoils after expansion.

In other embodiments, the shunt graft scaffold can be composed of multiple, individual stent components that may not be mechanically attached to each other using metal or some other attachment mechanism but can be supported using a flexible cloth. In this embodiment, the stents in the scaffold can be aligned and spaced relative to each other to promote flexibility of the overall shunt graft.

In some embodiments, the shunt graft can be covered by a cloth for sealing against the walls of the vessels in both the Glenn and the Fontan positions. The cloth can be a braid, weave, flexible polymer, or some other material that seals on the vessel and directs blood flow through the center of the shunt graft. The cloth can be made of a flexible material, but is not limited to, expanded polytetrafluoroethylene (or PTFE), Dacron, polyethylene terephthalate (or PET), or some other biocompatible cloth. In this embodiment, the cloth can be compressed to a size with the shunt graft of two millimeters in diameter and can be expanded to a size of twenty-four millimeters in diameter.

Figure 16:
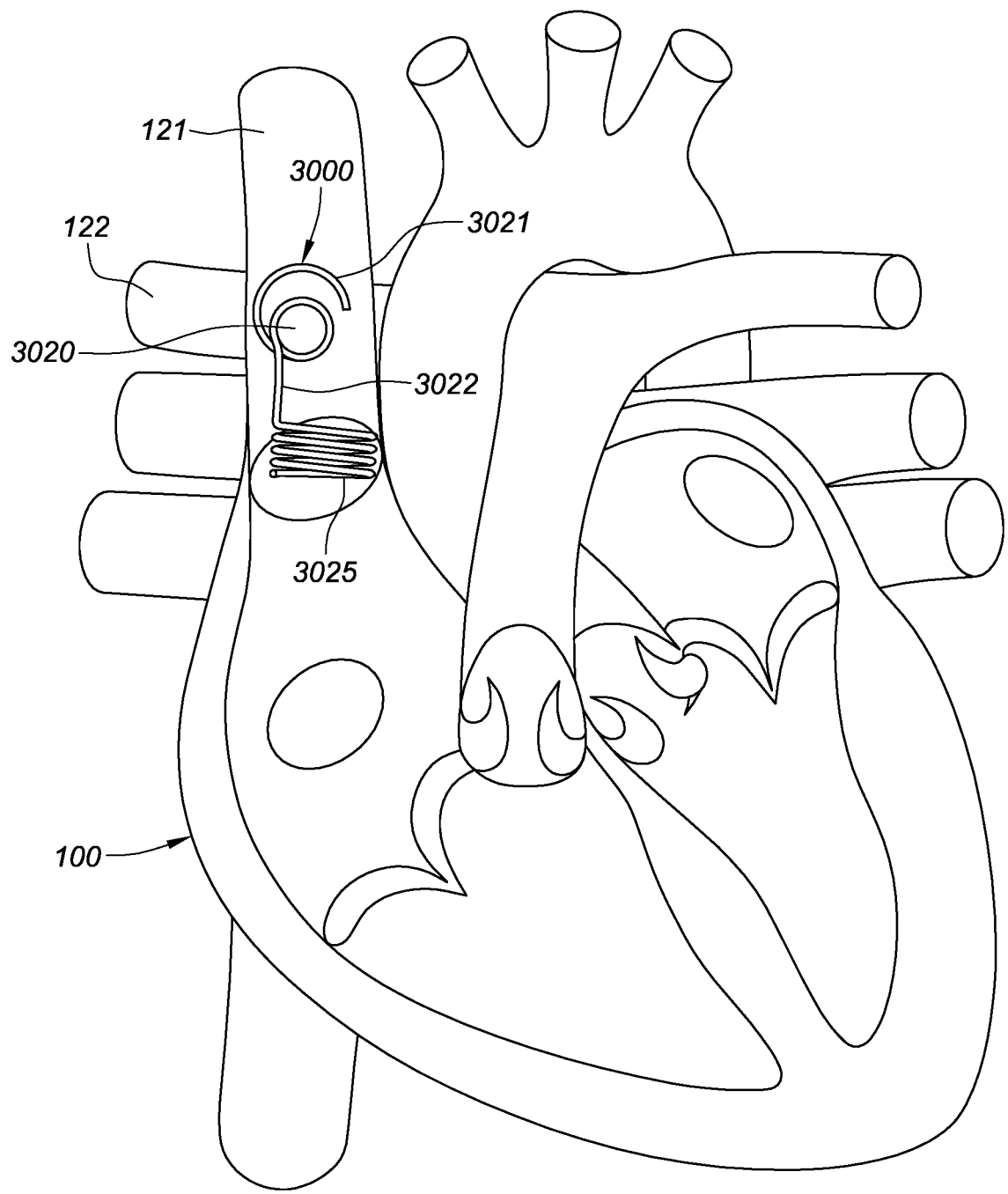
FIG. 16 is a detail drawing illustrating an exemplary embodiment of the wireframe shunt of FIGS. 15A-E, wherein the wireframe shunt implant is disposed in the anatomy of a patient.
Figure 17A:
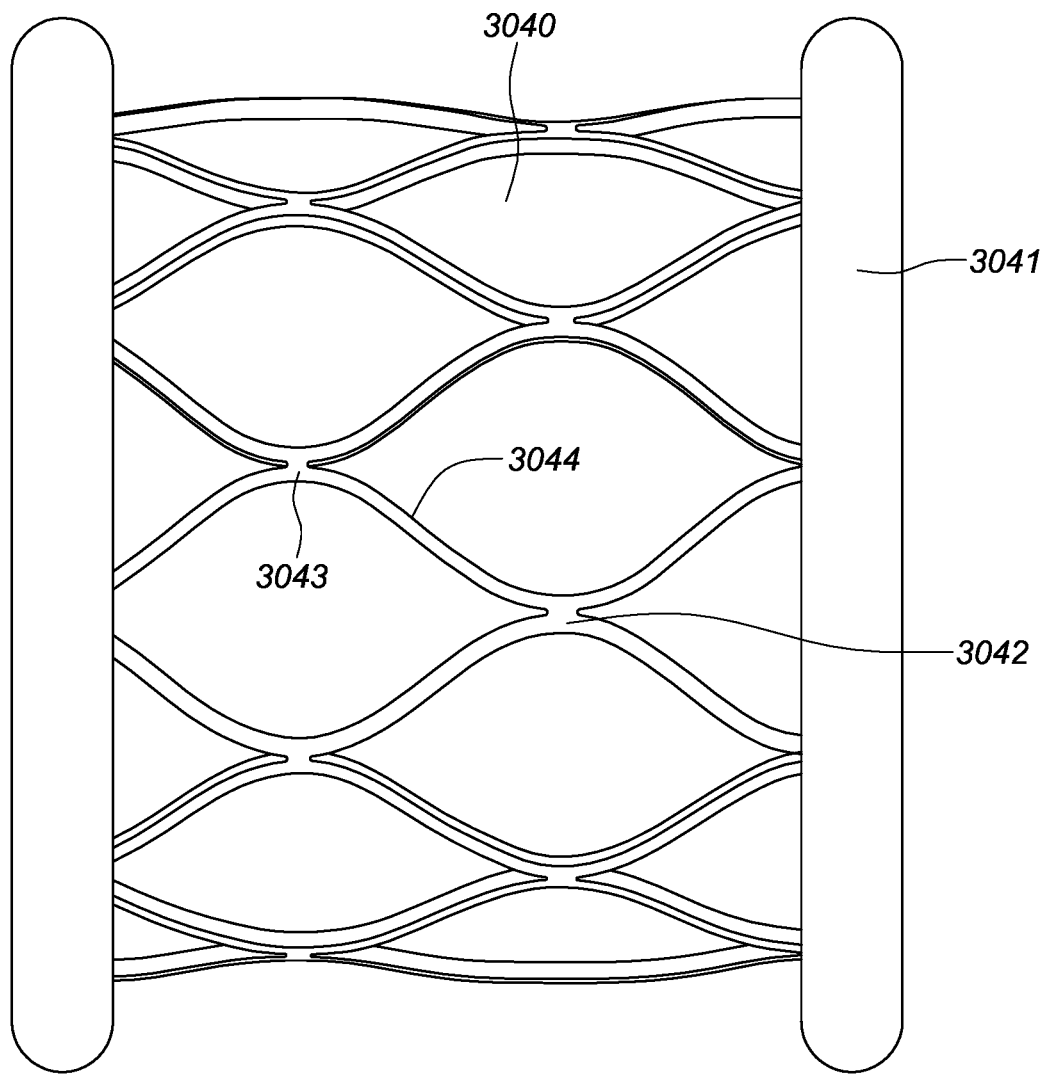
FIGS. 17A-B are detail drawings illustrating an exemplary embodiment of a transcatheter growth device, wherein the transcatheter growth device includes a growth shunt that has sealing and fixation rings of cloth (or foam material) at each end region.
Figure 17B:
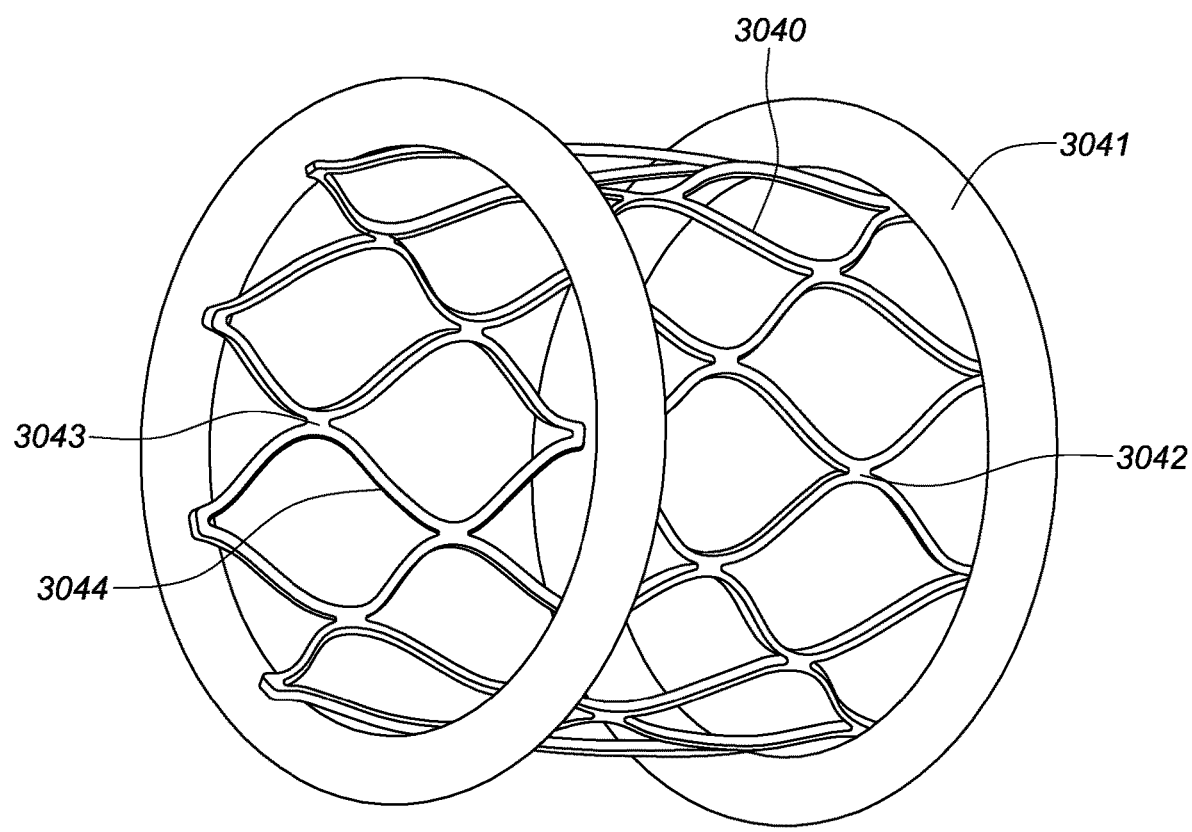
Figure 18:
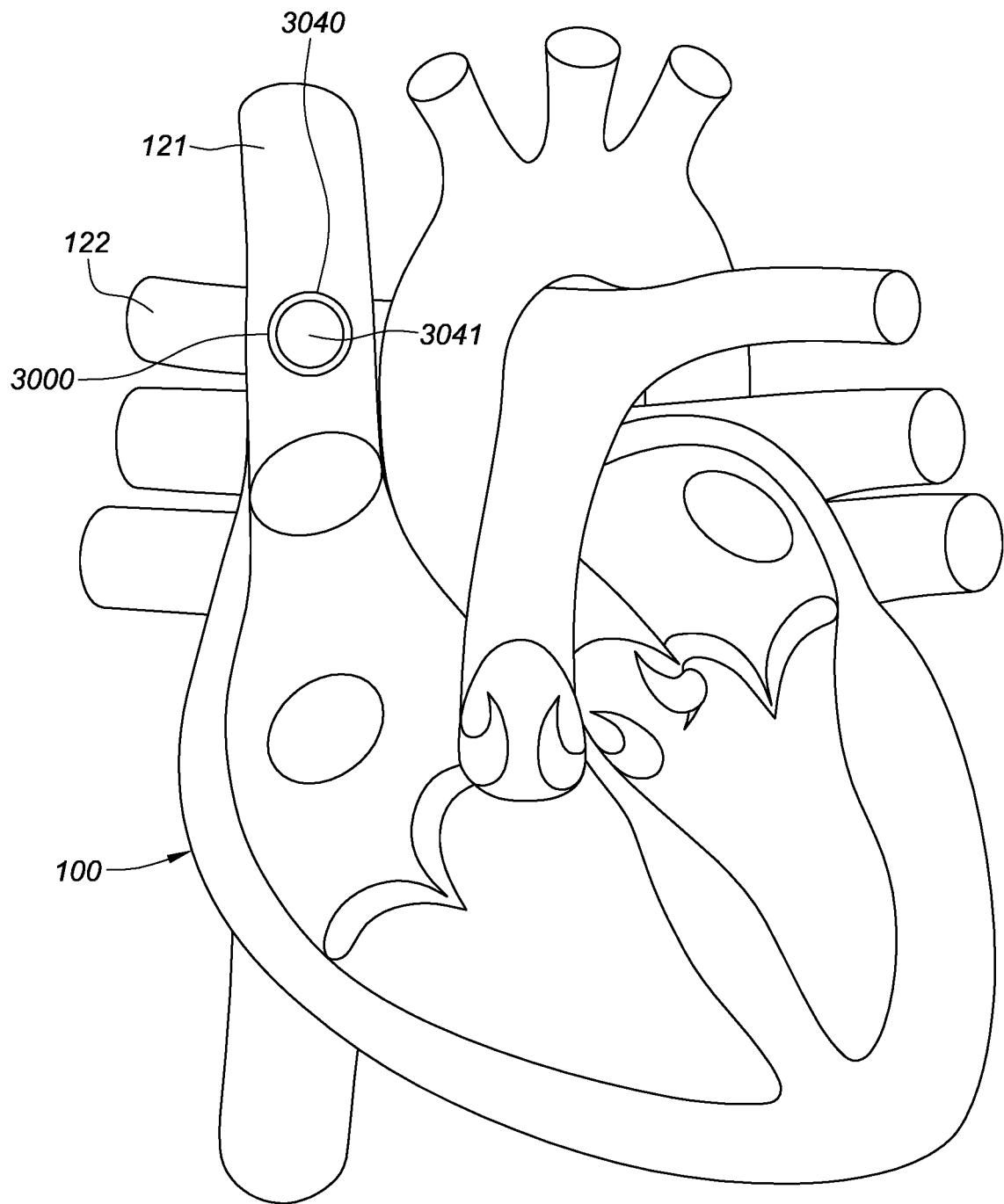
FIG. 18 is a detail drawing illustrating an exemplary embodiment of the shunt implant of FIGS. 17A-B, wherein the shunt implant is disposed in the anatomy of a patient.
Figure 19C:
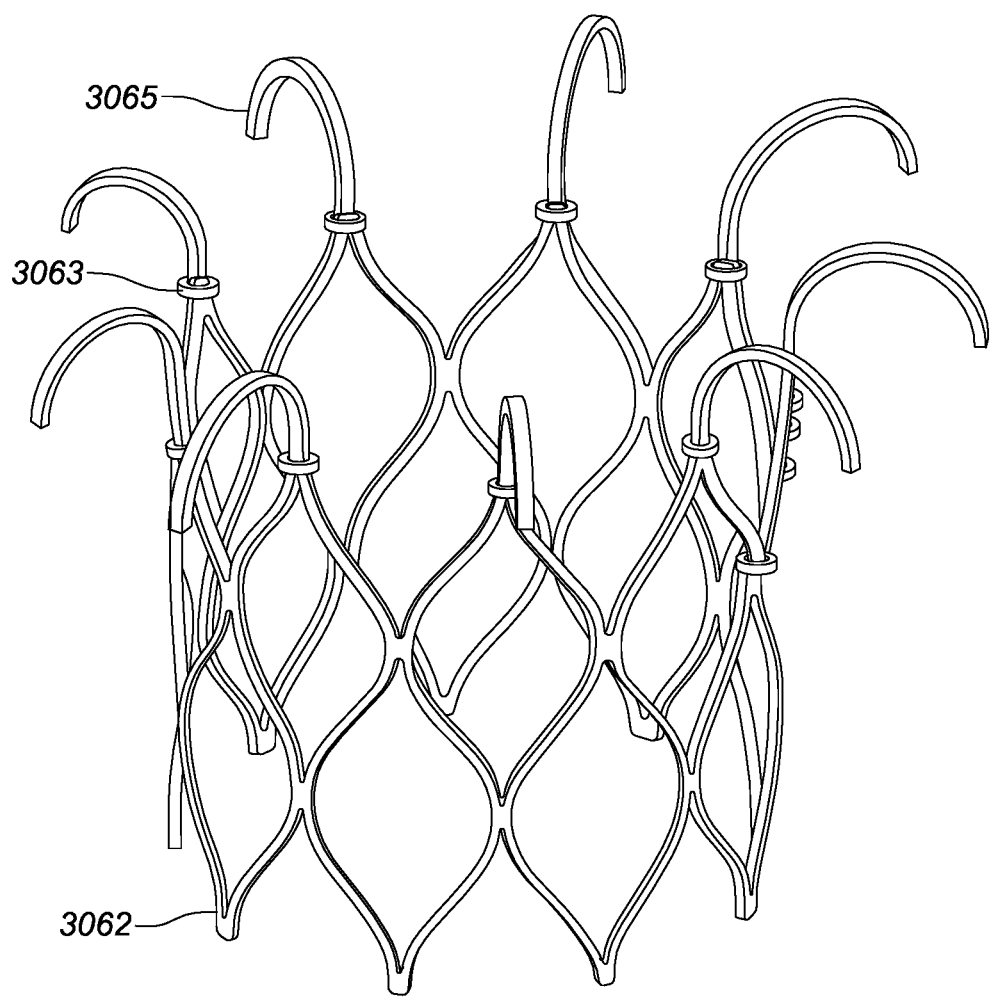
Figure 20A:
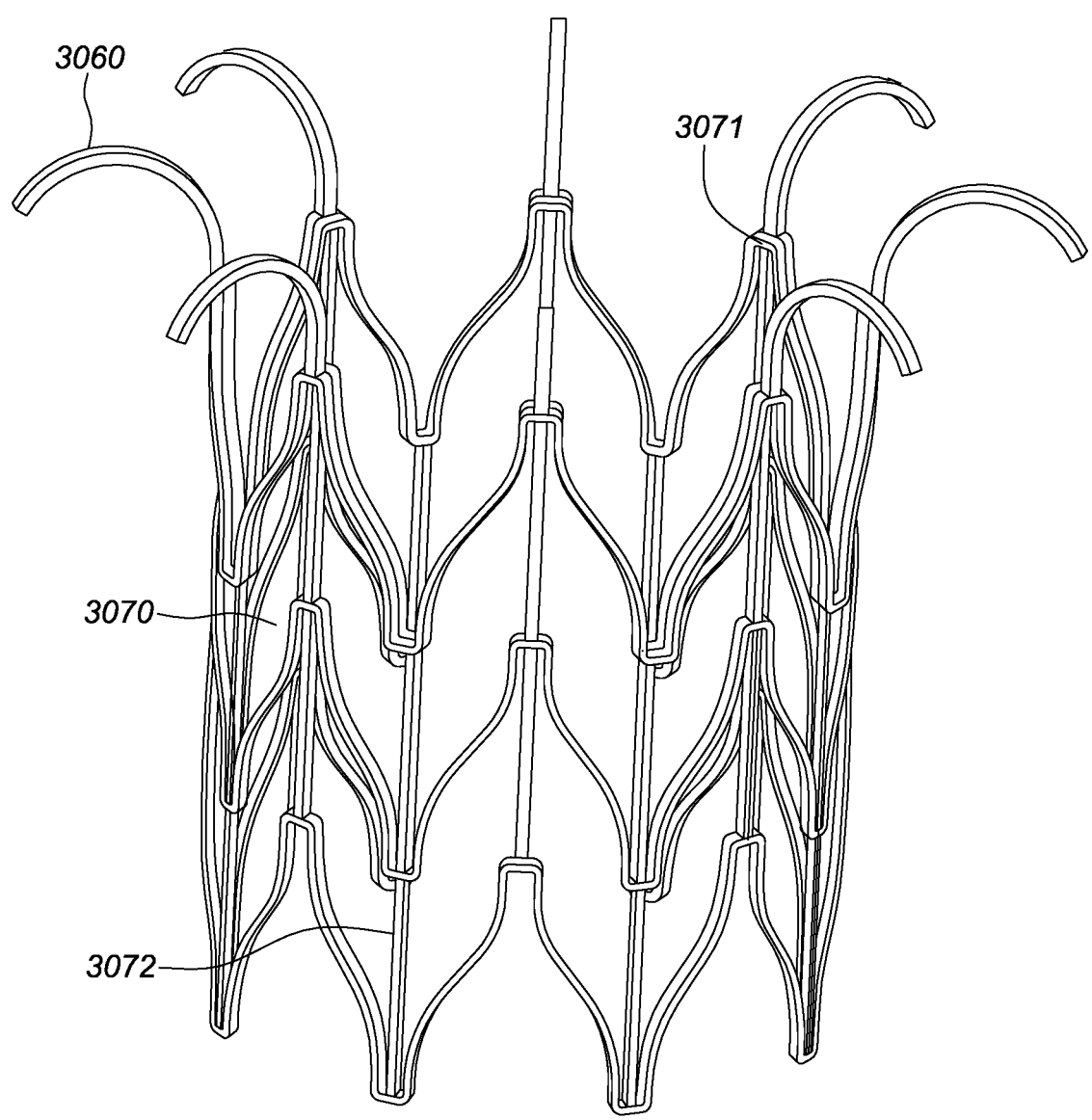
FIGS. 20A-B are detail drawings illustrating another exemplary embodiment of the dual frame shunt implant of FIGS. 19A-C, wherein the dual frame shunt implant is configured to minimize foreshortening of a length of the transcatheter growth device during expansion.
Figure 20B:
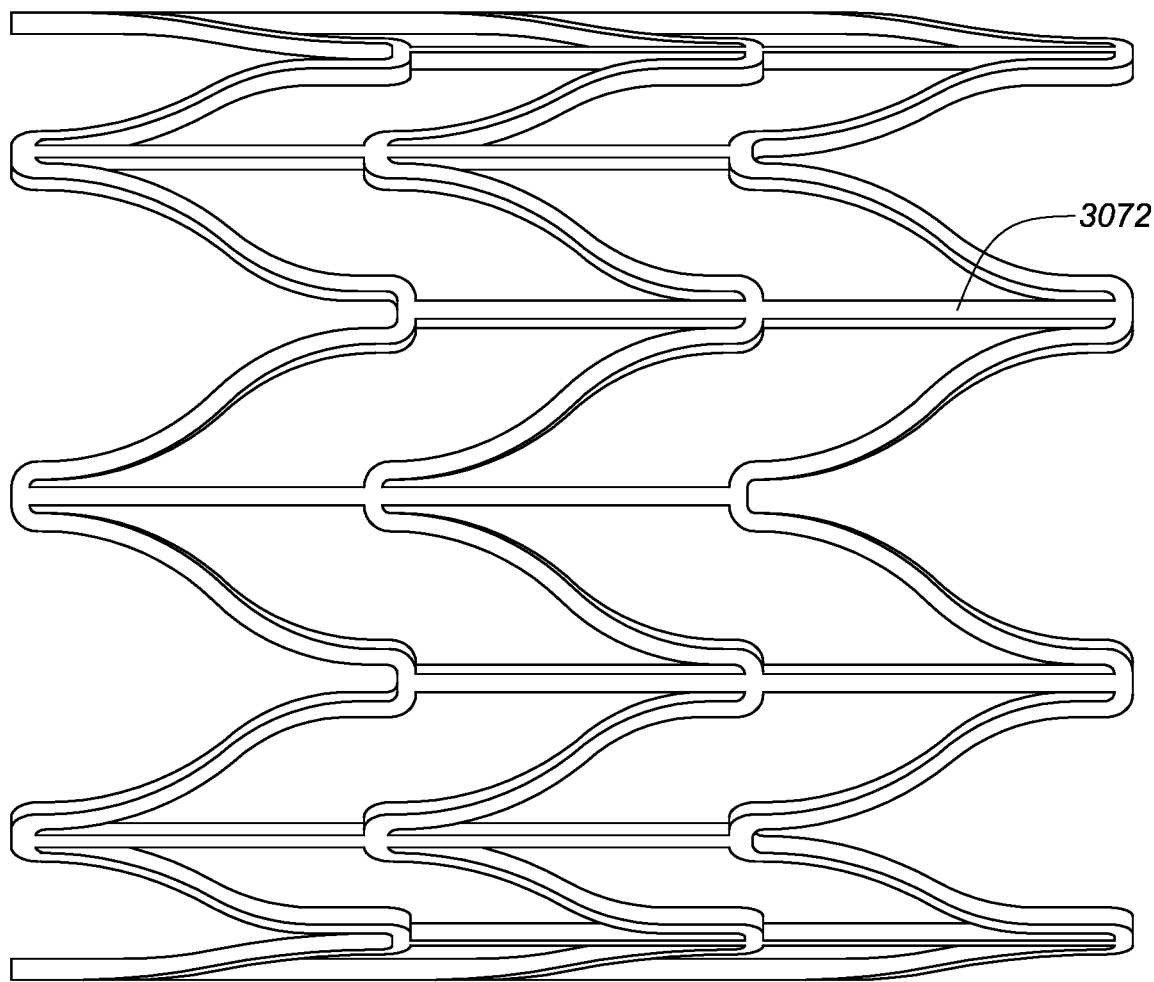
Figure 21:
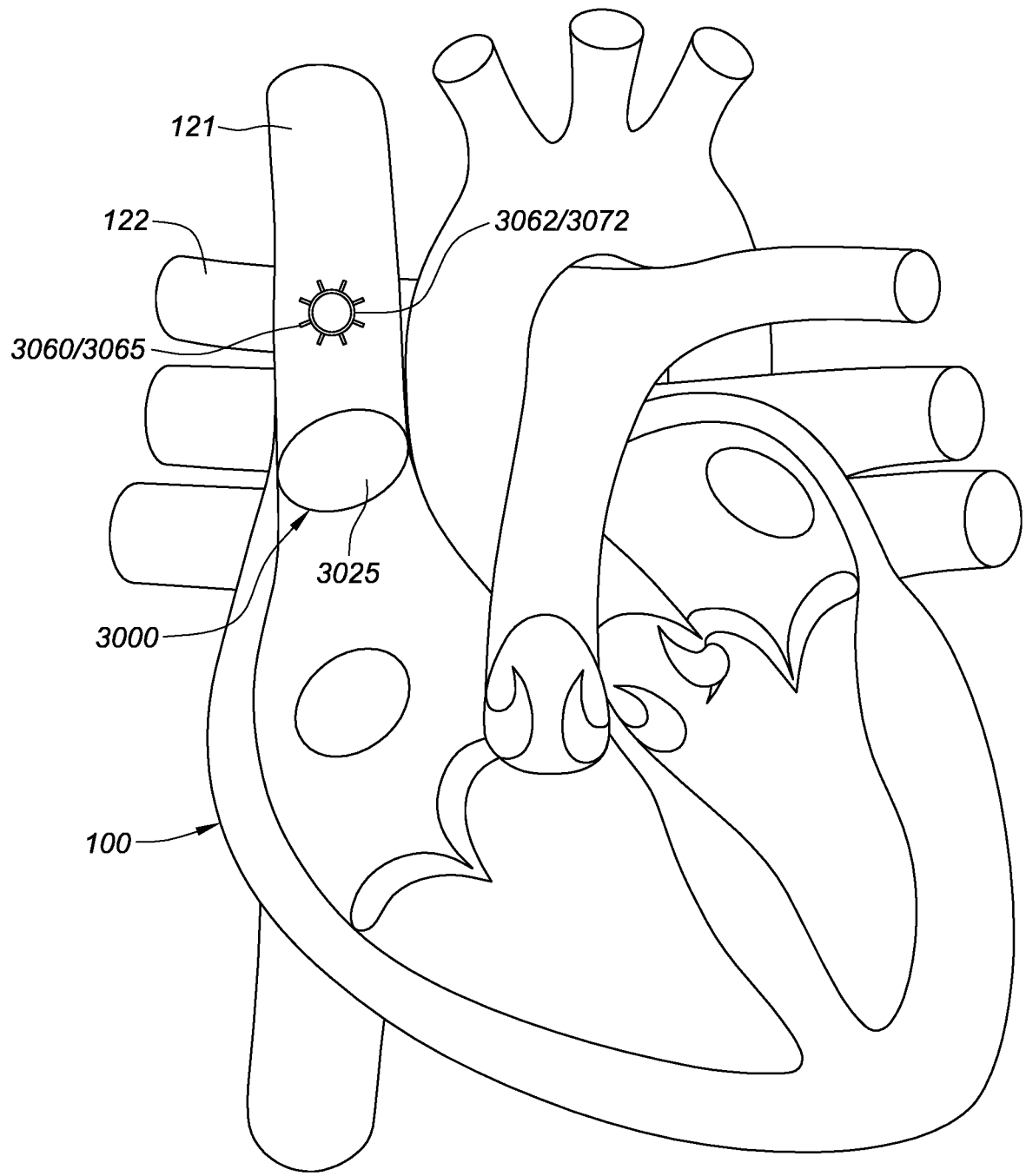
FIG. 21 is a detail drawing illustrating another alternative embodiment of the dual frame shunt implant, wherein the dual frame shunt implant is disposed in the anatomy of a patient.
Figure 22A:
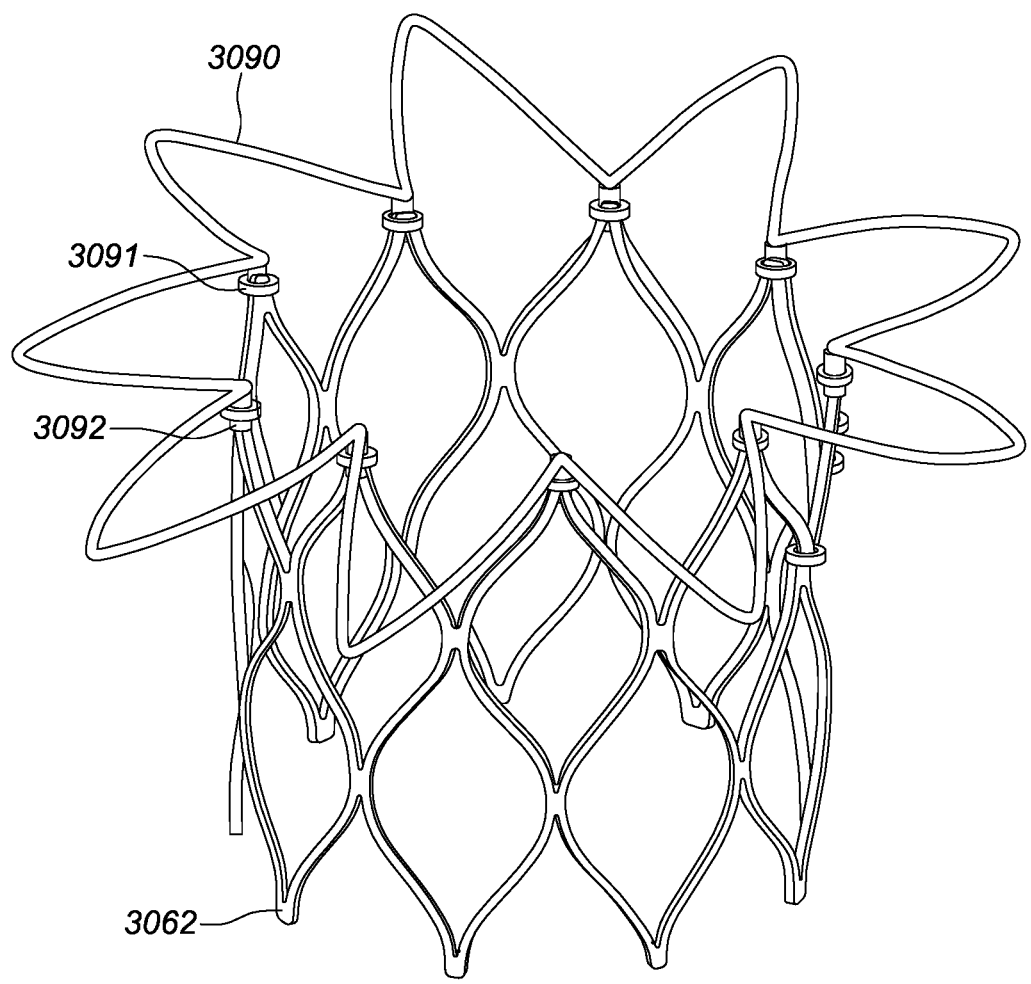
FIGS. 22A-C are detail drawings illustrating an exemplary embodiment of a transcatheter growth device, wherein the transcatheter growth device includes a single or dual material frame shunt implant with flat rings (or flanges) on one side and/or both end regions of the shunt implant.
Figure 22B:
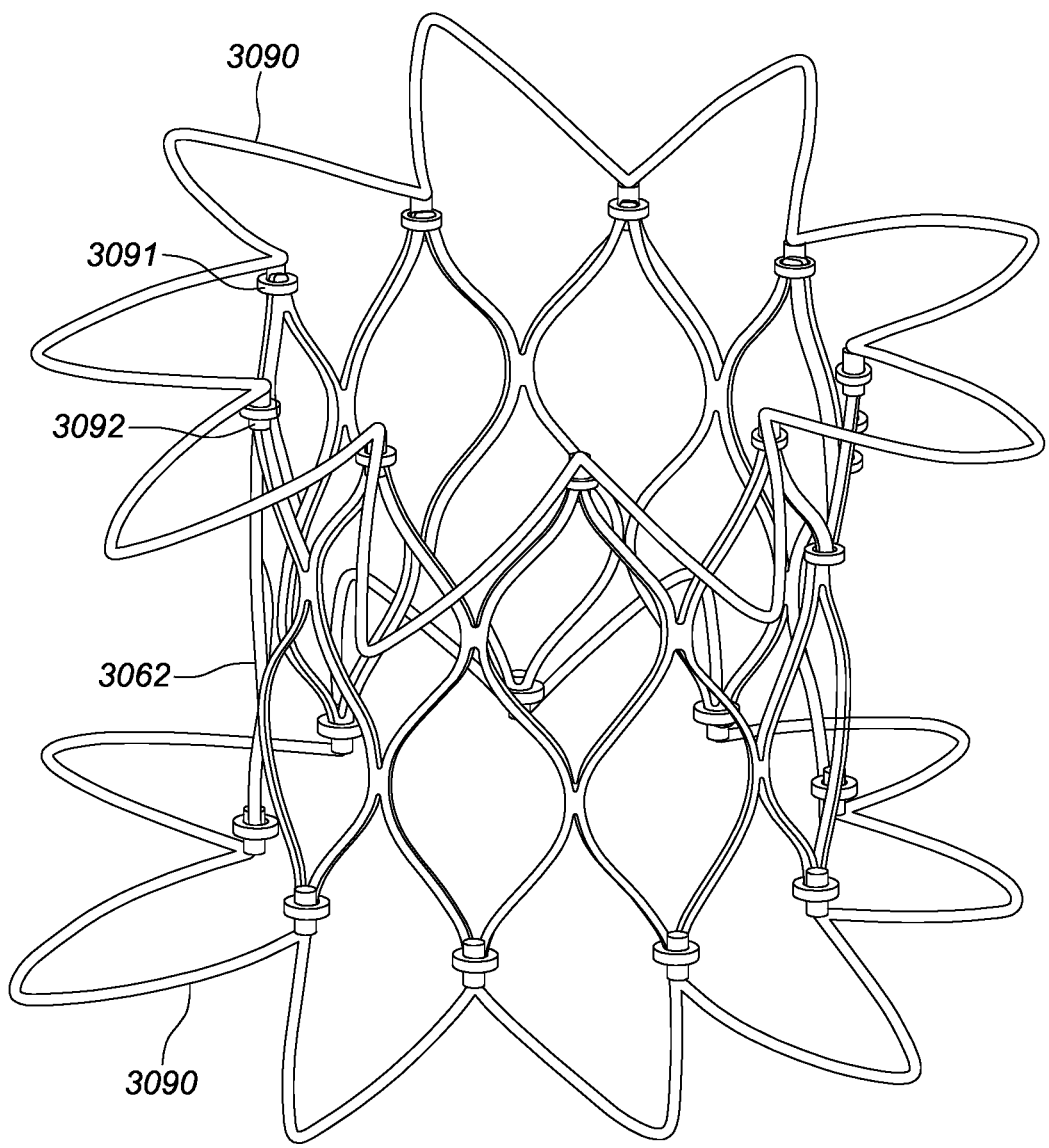
Figure 22C:
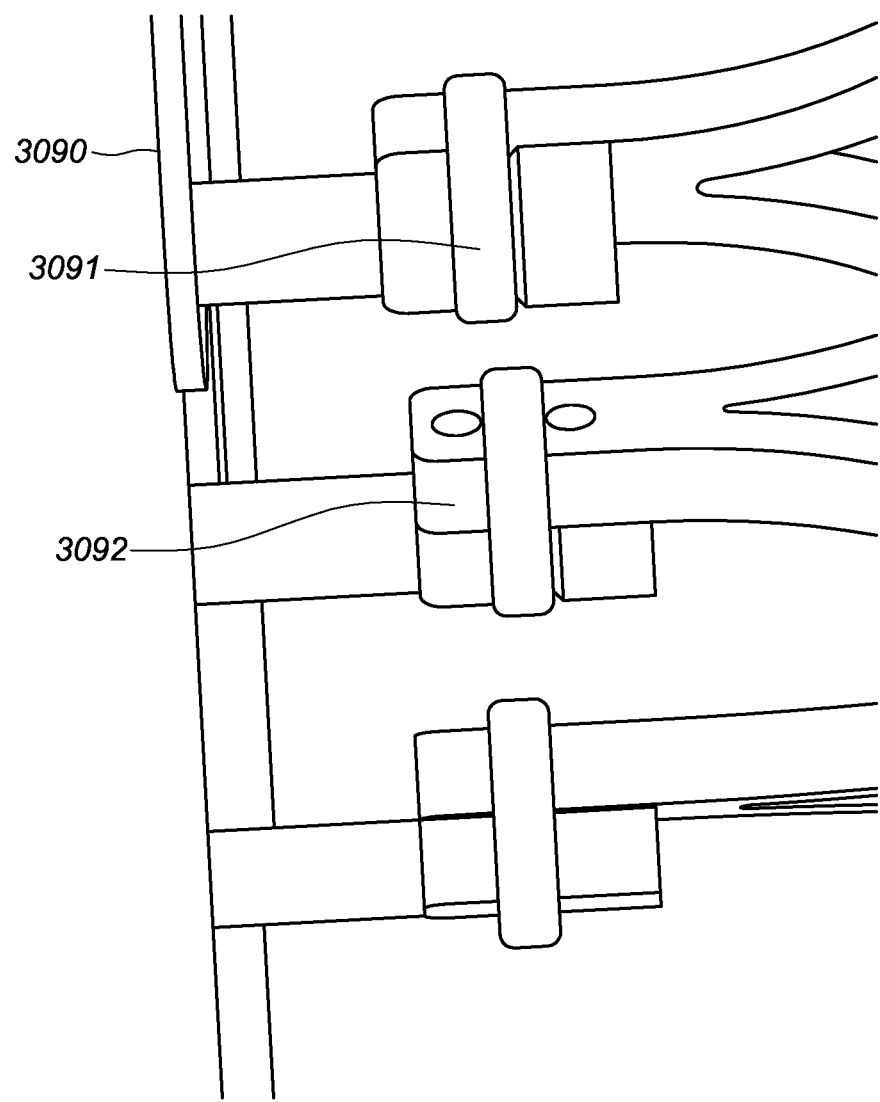

In some embodiments, a shunt 3000 can be created from the superior vena cava 121 to the pulmonary artery 122 during the Glenn procedure. In other embodiments, the shunt 3000 can be created from the inferior vena cava 124 to the pulmonary artery 122 during a Fontan procedure. As illustrated in FIGS. 15-16, for example, this shunt 3000 may be created using a wire frame (or coil) 3020 to hold the vessels together and create a fluid pathway between the vessels. The coil 3020 of the shunt 3000 can allow for blood fluid flow to travel from the superior vena cava 121 to the pulmonary artery 122. The coil 3020 of the shunt 3000 can be, but is not limited to, six millimeters to ten millimeters or more in diameter. The coil 3020 of the shunt 3000 may allow for expansion as the patient grows through the deployment of a stent (not shown) into the coil 3020 of the shunt 3000. The coil 3020 of the shunt 3000 may then unravel and expand with the stent. The wire frame and coil implant design can vary in pitch and diameter to achieve adequate vessel sealing and fluid flow. The material of the wire frame embodiment can be comprised of, but is not limited to, metal and metal alloys, polymer, biodegradable polymers, metal alloys, and/or a combination of multiple materials. This embodiment can have an optional attachment mechanism on the end region to allow for deployment and retrieval in a delivery system catheter. Some embodiments may also have flares or varying pitches and diameters throughout the coil and wire frame to allow for adequate fixation into the tangential vessels such as the pulmonary artery 122 and superior vena cava 121.

In some embodiments of the coil implant design, there may be a hook device 3021 on an end region of the coil implant 3020 that can provide adequate fixation in the pulmonary artery 122. This hook device 3021 can vary from a partial circle to a full circle.

As illustrated in FIGS. 17-23, the Glenn and/or Fontan shunt 3000 may be an expandable frame with a single or dual material implant. Materials utilized for either frame component can range from, but is not limited to, nitinol, cobalt chromium, stainless steel, other metal alloys, medical grade clothes and foams, and polymer and biodegradable polymer materials. In some embodiments, the frame can allow for a growth feature to be expanded later after the development and vascular growth of the patient. The frame body 3062, 3070 can range in diameter from one millimeter to twenty millimeters or more (or any subrange in between). The second frame component 60, 65, 90 and material can provide adequate fixation and connection between the connected superior vena cava 121 and pulmonary artery 122. This fixation feature can optionally be embodied through a flare, hooks, outward radial force onto the vessel, and/or barb mechanisms. These fixation mechanisms can be created from a laser cut hypo tube, a wire, or another fixation mechanism, without limitation. The multi-frame implants can be attached together by various mechanisms 3061, 3063, 3091 such as, but not limited it, suture attachment 3061, 3063, 3091, welding, mechanically locking, or with adhesive. In multi-frame implants, some embodiments of the transcatheter growth devices can consist of a bare metal frame on frame contact, or there may be a cloth or polymer spacer in between the frames in the attachments. In some multi-material embodiments, there may be implant grade foam 3041 or cloth on the end regions of the metal frame to allow for fixation and sealing of the shunt 3000. In a single frame embodiment, this design can include a straight tube frame or a tube frame with flares on one or both end regions of the shunt and a straight midsection. These embodiments provide a mechanism to shunt into a single ventricle patient with the ability to expand to adult sizes. As shown in FIG. 20B, one or more selected struts of the shunt 3000 can be disposed in a chevron configuration. The selected struts in the chevron configuration advantageously can help to limit foreshortening with beam members connecting strut apexes.

For some embodiments, the shunt implant 3000 may comprise of nitinol hooks that are connected by cloth to create the fluid blood flow channel from the superior vena cava 121 to the pulmonary artery 122 or the inferior vena cava 124 to the pulmonary artery 122. These hooks may grab onto the pulmonary artery 122 to pull the vessel towards the superior vena cava 121 and fixation in place. The second set of hooks may latch onto the superior vena cava 121 or inferior vena cava 124 wall. The cloth connected the two set of hooks 3060, 3065 or flanges 3090 may be wire reinforced for structural stability and can be expanded to larger sizes. For some embodiments, the shunt implant 3000 can be re-dilated and/or re-expanded to adult sizes through an active balloon inflation mechanism or may grow passively with the body. In some embodiments, the frame design may enable the implant to reach the target diameter ranges without fractures and while maintaining structural stability. The individual strut body may be designed in a S-shape to help with strain distribution across the diameter range. The strut junctions may be increased to allow for larger radial force, and the strut connector radius may be designed in a way that allows for smaller crimping and larger expansion ranges.

One embodiment of the implants 3000 for the Glenn Procedure involves two separate implant and delivery catheter systems for delivering the superior vena cava 121 to pulmonary artery 122 shunt and then subsequently implanting a superior vena cava 121 occluding device. FIGS. 15-16 illustrate an exemplary embodiment of a combination device that can complete both desired outcomes, the superior vena cava 121 to pulmonary artery 122 shunt coil 3020 and the superior vena cava 121 occlusion coil 3023, 3025, in a single implant. The shunt coil and the superior vena cava 121 occlusion coil could have a connector feature 3022. One embodiment shows a coil with a polymer like polytetrafluoroethylene (PTFE) or another type of cloth material 3026 that may fold on itself to create a superior vena cava occlusion once the coil 3020 is released from the catheter.

Figure 23A:
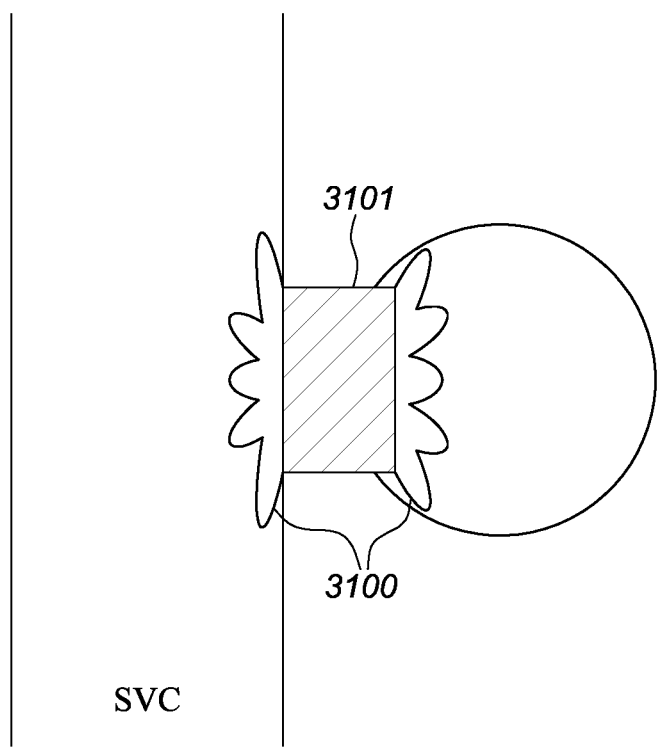
FIGS. 23A-B are detail drawings illustrating an exemplary embodiment of a transcatheter growth device, wherein the transcatheter growth device includes a dual ring shunt that is connected by fluid-impermeable cloth and optionally structurally supported with a wire and/or rows of cells.
Figure 23B:
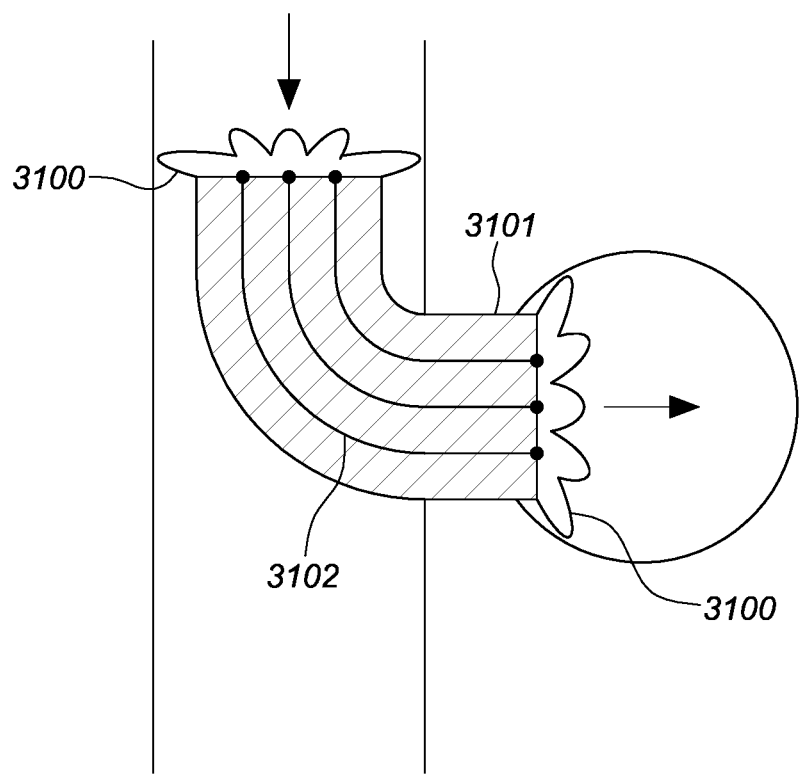

FIG. 23 illustrates a dual ring implant 3000 that can include two or more rings and/or that can be connected by an impermeable cloth or polymer covering to divert blood flow from the superior vena cava 121 into the pulmonary artery 122. The ring implant 3000 may provide multiple purposes such as allowing for a re-dilation mechanism to grow to adult sizes. The implant rings may also provide adequate fixation through oversizing into the superior vena cava 121. FIG. 23 illustrates the ring expansion into the superior vena cava 121 to divert all flow from the superior vena cava 121 into the pulmonary artery 122 while blocking flow from the inferior vena cava 124 and/or the right atrium 123. Some embodiments of this implant ring system have a target location for re-entry for a later procedure to open the blood flow channel from the inferior vena cava 124 and/or the right atrium 123 into the superior vena cava 121 or other openings and connections. The covering on the implant system 3000 may be structurally reinforced by metal wire 3102 or polymer strands 3102 to help ensure patency of the blood conduit. Some embodiments of this covering are braided strands, and some are monofilament strands. One embodiment does not utilize cloth or another polymer for the conduit, but rather two expandable implant rings 3100 that can be connected by cloth 3101 and/or can be isolated to the junction between the superior vena cava 121 and the pulmonary artery 122.

The expandable rings may be crimped down to fit into a four to eight French catheter and may be expanded to twenty millimeters. The expandable rings may be flared or straight and could have a canted angle. The flared end regions of the expandable ring could be formed due to the shape memory and superelasticity properties of nitinol or may be manually created with a balloon expansion that inflates to a larger diameter at the end regions of the balloon. The impermeable cloth 3101 advantageously can allow for a complete blood diversion from the superior vena cava 121 to pulmonary artery 122 and to seal off the junction between the pulmonary artery 122 and the superior vena cava 121 to any blood leaks.

Figure 24A:
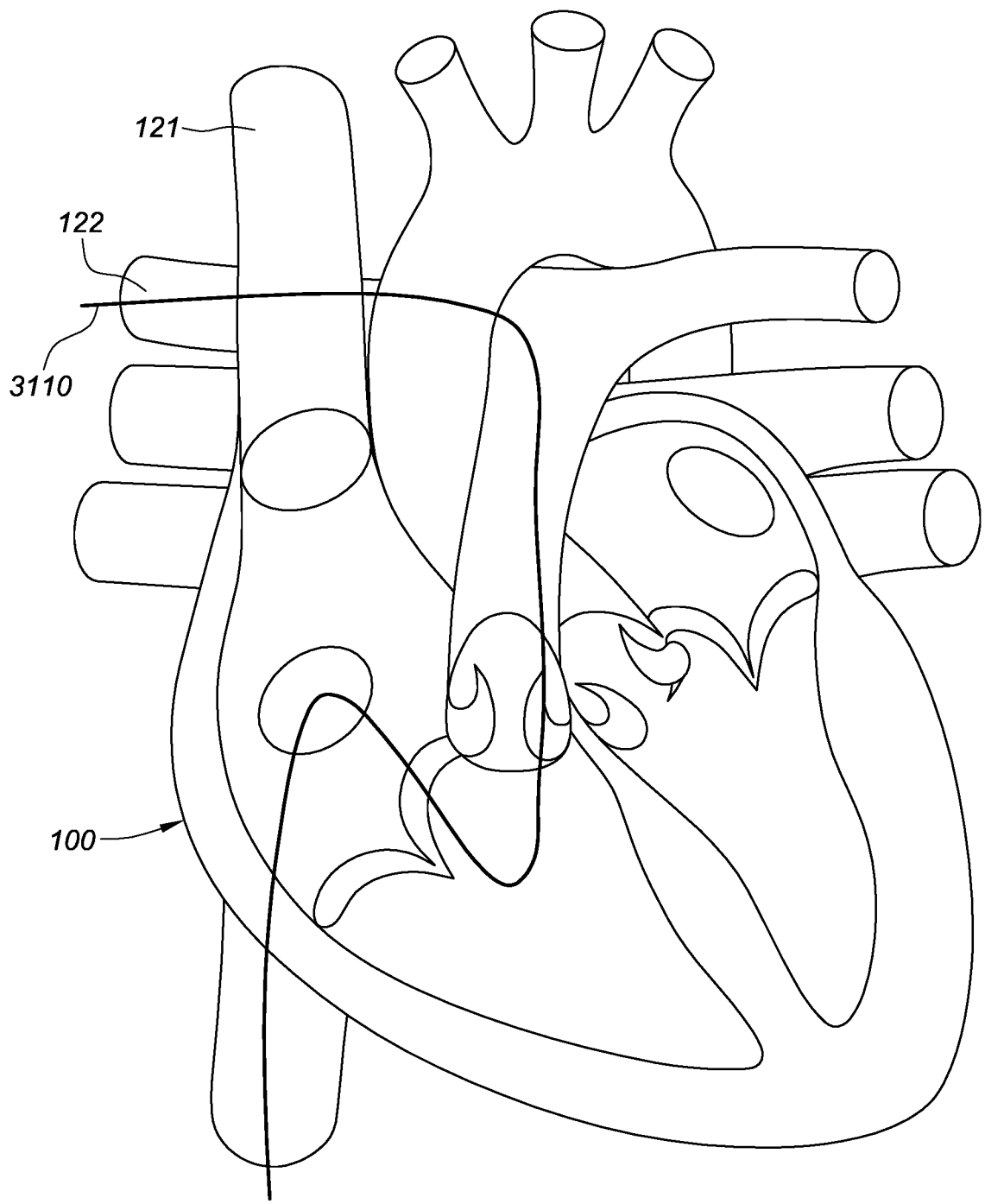
FIGS. 24A-C are detail drawings illustrating selected techniques for visualizing a crossing of the pulmonary artery (or PA) and the superior vena cava (or SVC) of a patient, wherein the techniques can involve guidewires, fluoroscopy markets and/or a balloon filled with contrast solution.
Figure 24B:
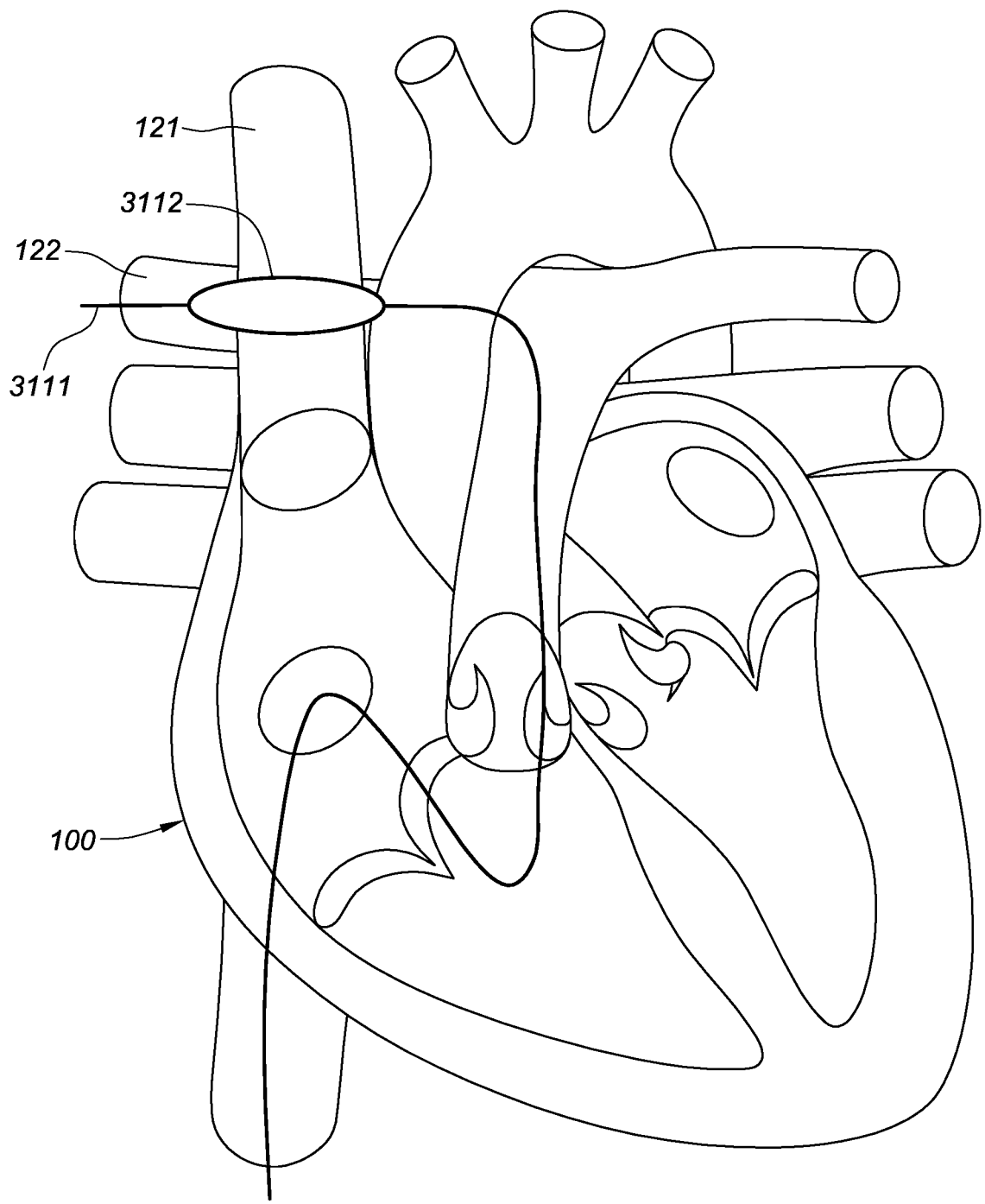
Figure 24C:
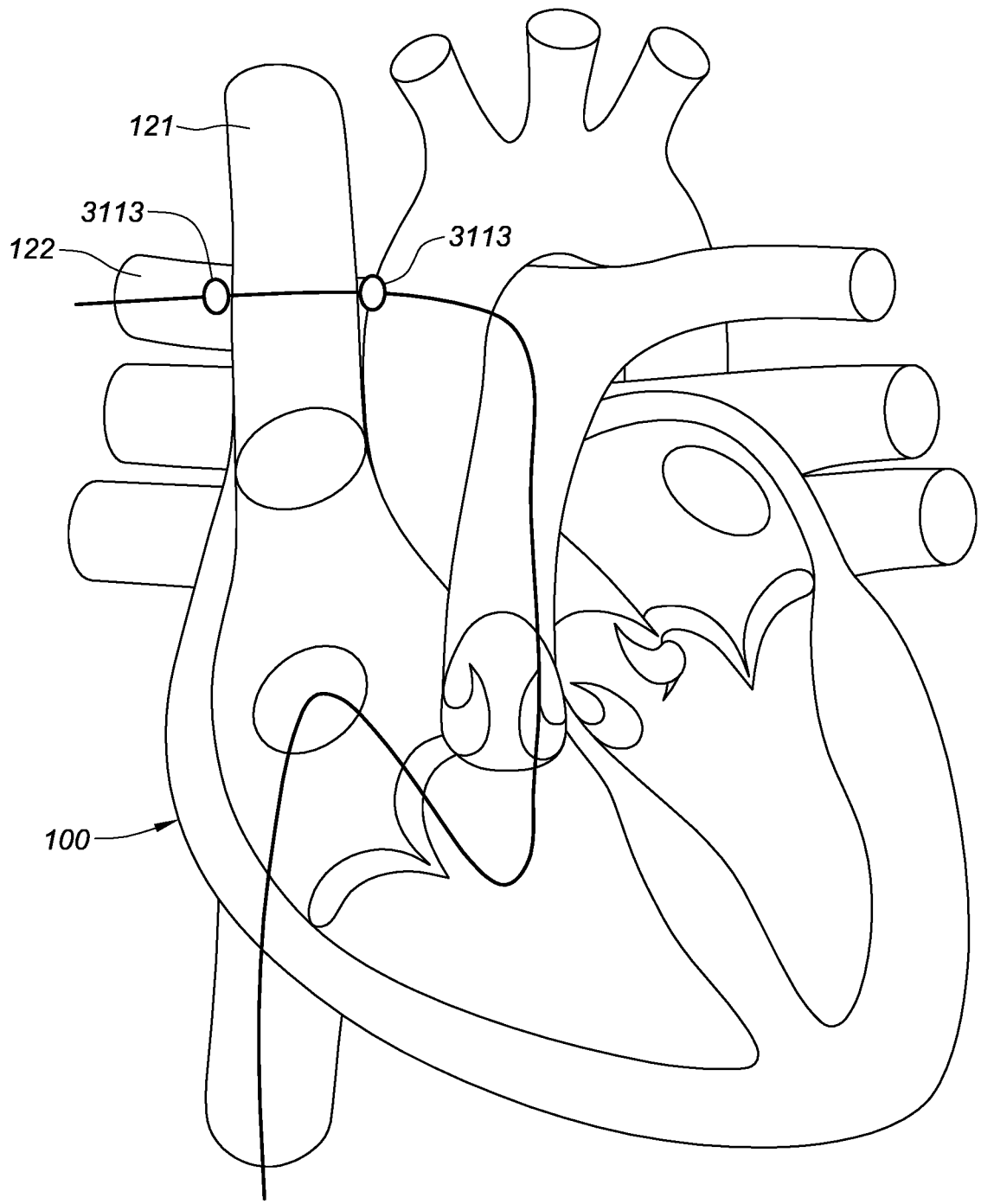
Figure 25:
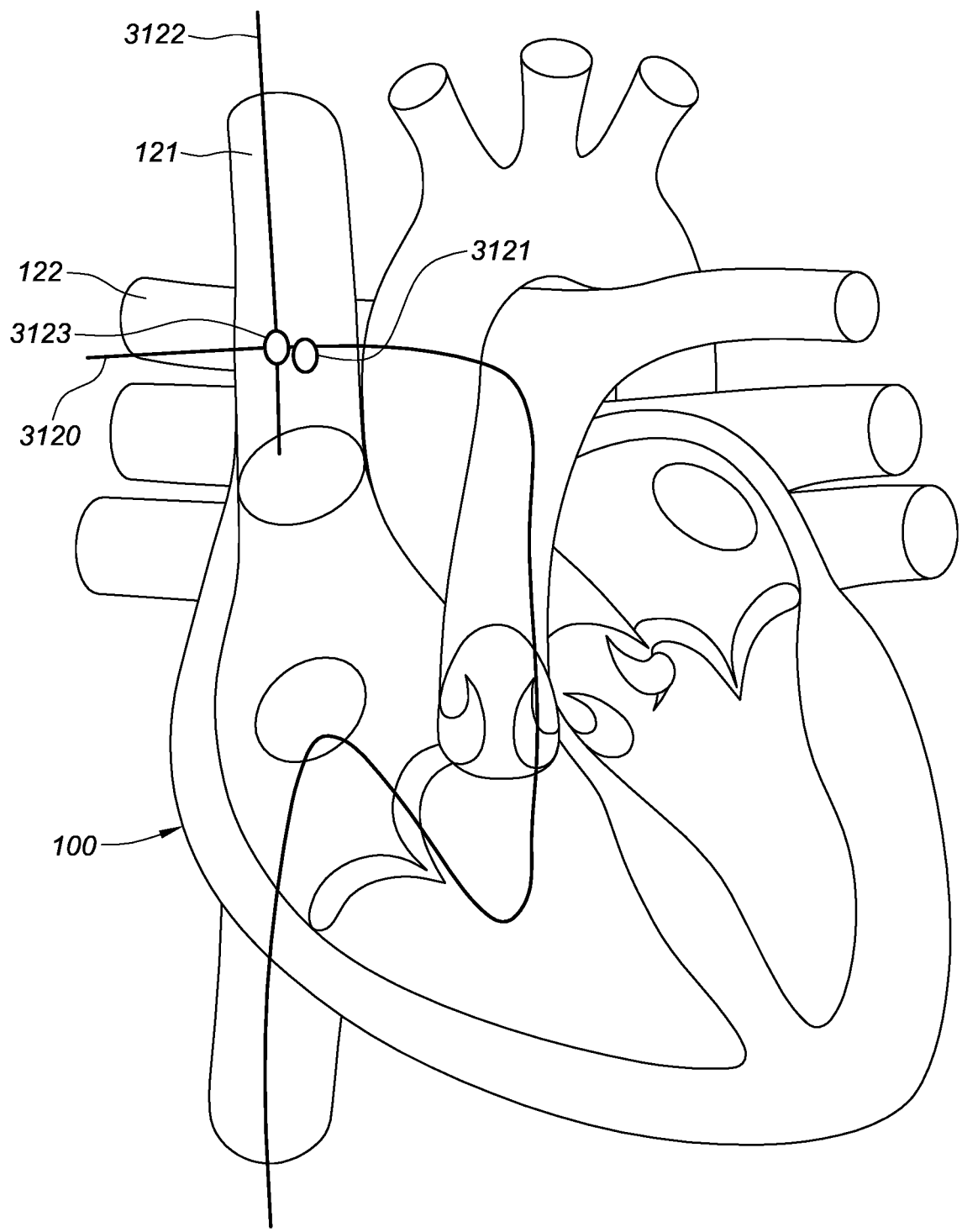
FIG. 25 is a detail drawing illustrating a use of one or more magnets to line up the crossing of the SVC and PA.
Figure 26:
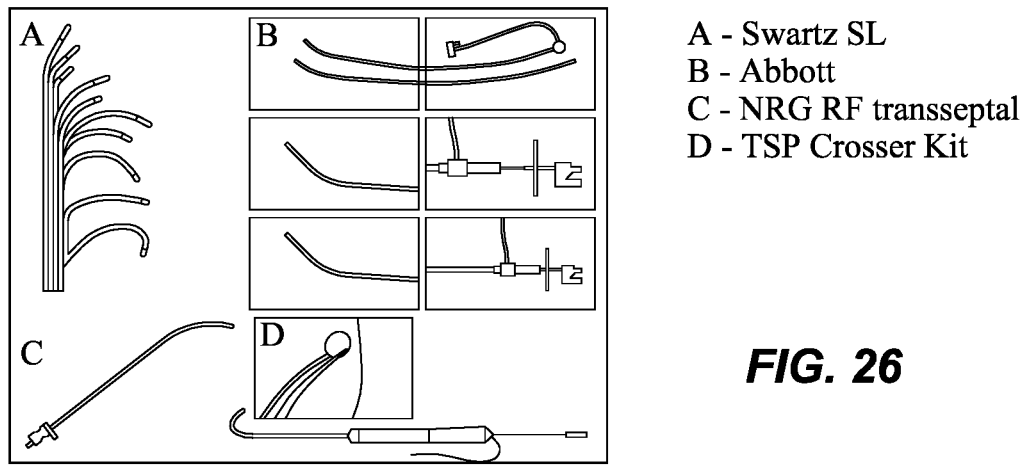
FIG. 26 is a detail drawing illustrating selected crossing systems for creating access into the PA from the SVC.

FIGS. 24-26 demonstrate exemplary procedural mechanisms and techniques that can allow for access of the pulmonary artery 122 through the superior vena cava 121.

Some embodiments related to the pulmonary artery 122 access from the superior vena cava 121 illustrate various visualization techniques to provide guidance for puncture location. The visual guidance may consist of a single guidewire 3110 placed into the pulmonary artery 122 to provide a fluoroscopic indication for where the pulmonary artery 122 and superior vena cava 121 cross in the anatomy. Fluoroscopic markers 3113 can be used to further highlight the target area. These markers can be made of material ranging from, but not limited to, gold, tantalum, platinum, or other metal alloys. A visual indicator could involve the use of a balloon catheter 3112 that is inflated with contrast solution for full pulmonary artery 122 vessel visualization. Once the visual indicator is in position, the fluoroscopic imaging machinery can be oriented at different angles to get the best visual position for gaining access into the pulmonary artery 122 from the superior vena cava 121.

Turning to FIG. 25, magnets 3121, 3143 can be utilized for properly aligning an exact location of where the superior vena cava 121 and pulmonary artery 122 cross. This can be accomplished by placing a first magnet 3121 in the pulmonary artery 122 and a second magnet 3123 in the superior vena cava 121. Once the first and second magnets 3121, 3123 come close enough, the magnetic fields should pull them together to give an indication of where the access should be created. The magnets 3121, 3123 can be standalone catheters 3122, 3140 and/or can be integrated into a needle access catheter (not shown). Once the magnetic connection is made, a curved or straight needle (not shown) can be translated out of the delivery system in the direct of the pulmonary artery 122. Some embodiments of the magnets 3121, 3123 can comprise electromagnets 3121, 3143, and/or some magnets 3121, 3123 can comprise polarity magnets. Electromagnets can be engaged with an electric current to provide the ability to turn the magnets from working to null.

Puncture catheters advantageously can be utilized to create a hole in a vessel wall for catheter access om the manner illustrated in FIG. 26. FIG. 26 can serve as an example embodiment that can be elaborated for different indications. In some embodiments, the catheter can have a steerable tip for positioning before puncture, and in other embodiments the catheter may have a pre-curve built in, ranging from ten degrees to ninety degrees and beyond.

Some embodiments contain a puncture needle that exits the catheter to create access that may have a pre-curve built into the design that can actuate manually. The pre-curve for both the catheter and the needle may be manually created in an operating room before insertion into the patient. The needle used to create access from the superior vena cava 121 to the pulmonary artery 122 may have a location on the proximal side of the handle to connect electrodes. In selected embodiments, the electrodes can be energized to generate thermal energy at the needle tip to allow for easier puncture into the pulmonary artery 122 or other vessel wall. The needle material can be, but is not limited to, stainless steel, nitinol, or a durable polymer. There may be a sealing cloth or foam around the body of the needle to ensure there is no excess bleeding once access is created.

In some embodiments of the puncture needle, the needle can be shaped in a corkscrew fashion. The corkscrew-shaped need can allow for turning of the needle in a circular rotation to penetrate through a vessel wall. In other embodiments, the needle can be shaped like a hook to allow for force to be applied to a vessel to bring the vessel closer to the catheter. Selected embodiments of the needles may be manually actuated, automatically actuated or actuated in another manner.

Figure 27:
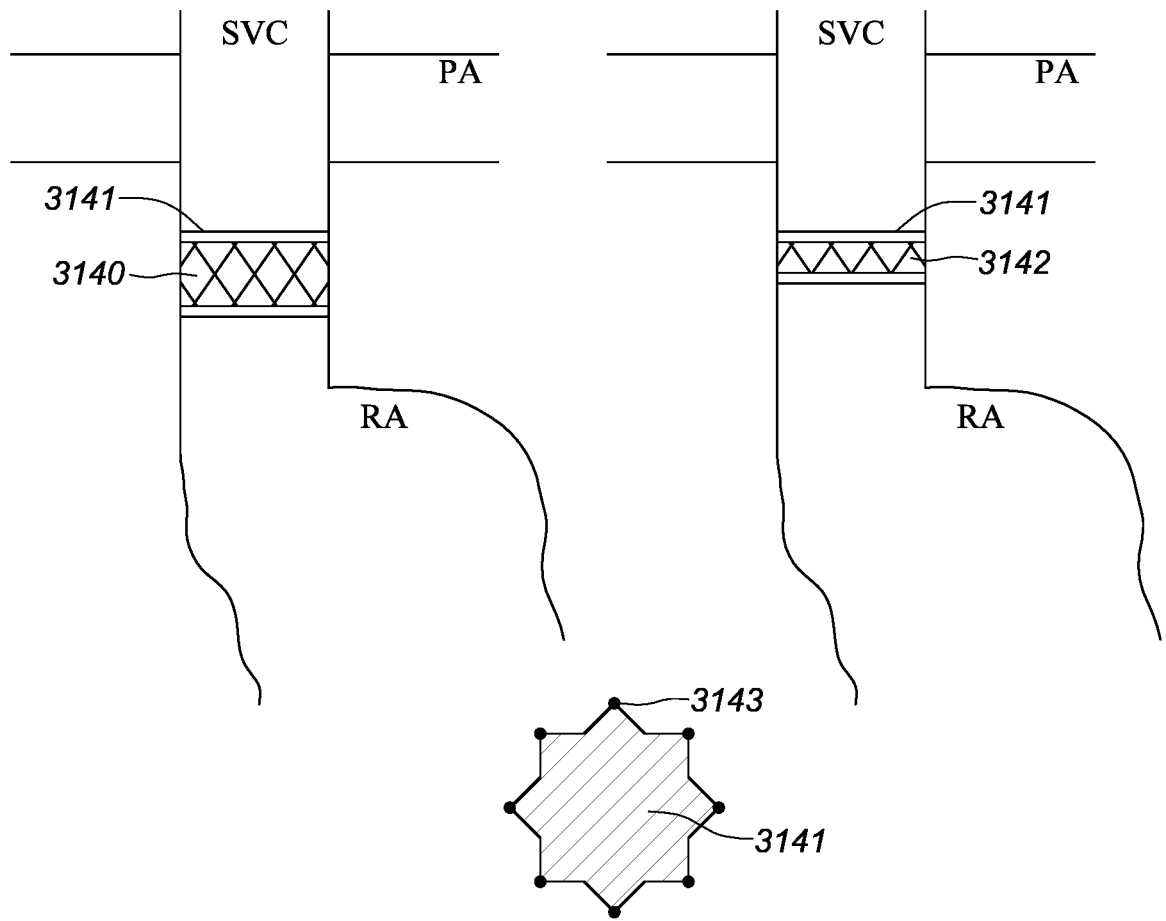
FIG. 27 is a detail drawing illustrating an exemplary embodiment of a transcatheter growth device, wherein the transcatheter growth device includes a covered end region for blocking flow from the SVC to the right atrium (or RA).

Turning to FIG. 27, an implant occlusion system can be used to inhibit blood fluid flow from the superior vena cava (or SVC) 121 into the right atrium (or RA) 123. This occlusion implant may have a metal frame 3140, 3142 with an impermeable cloth 3141 covering the entirety of one end region to help ensure that no blood can flow from the superior vena cava 121 into the right atrium 123.

The material used for the SVC to RA occlusion implant can be, but is not limited to, nitinol, cobalt chromium, stainless steel, polymers, or biodegradable polymers. The frame used for the occlusion implant may allow for repeated re-dilations later in the life of the patient.

To expand the occlusion implant device, a custom-designed balloon may be used. Additionally and/or alternatively, the implant may be self-expanding.

The impermeable cloth 3141 for diverting blood fluid flow can be made from polyethylene terephthalate (or PET) or, potentially, a biodegradable polymer. The cloth may allow for tissue ingrowth and healing. The cloth may have a perforation in the design for re-access with a needle at a later stage procedure in the life of the patient. The cloth can be made to be stretchable to encompass a broad range of deployment diameters. The cloth components of the occlusion implant may have sealing foam or other sealing devices attached on the edges of the implant to ensure no blood flow may leak around the implant 3000.

In one embodiment, the occlusion implant device can have a foam or other sealing material 3141 filling the orifice of the frame. This can allow for catheter components to pass through the foam for proper trackability. Once the catheter components are removed, the foam can relax and seal off any blood flow passing through the barrel of the implant. In other words, the foam or sealing material can provide a seal for blood flow but can be able to open for a catheter to cross, then re-sealing after the catheter is removed from the barrel of the device. This foam material can range from a thermally lifted PET or other polymer material. The foam can have shape memory and superelastic properties, as well. The density of the foam may allow for blood to be trapped and clotted so that over a short period of time, the barrel of the implant is completely shut off to fluid blood flow.

In some embodiments, the frame of the occlusion implant can be made of a biodegradable material that can degrade over time and be a scaffold for tissue ingrowth. This degradation can occur over a wide range of time and, once the implant has fully degraded, the anatomy of the patient can have full autonomy to grow and develop. The biodegradable material can provide initial structure for the occlusion implant and radial strength, while degrading over time to leave the occlusion without the biodegradable material.

For fixation into the walls of the superior vena cava 121 or inferior vena cava 124, the occlusion implant can have an individual or a combination of fixation mechanisms. One of these fixation mechanisms may be to utilize barbs or friction elements, such as rough surface textured cloths and metals. The occlusion implant may also utilize radial force and oversizing from self-expansion or balloon expansion, as a form of fixation. The implant may have a flare on one end region or both, which would provide enhanced fixation and potentially enhanced sealing capabilities. The SVC occlusion implant may also utilize the roof of the RA with a flange to ensure there is no migration upwards.

FIGS. 28-32 illustrate various transcatheter Fontan approaches to adequately divert flow from the inferior vena cava 124 to the superior vena cava 121 and pulmonary artery 122, completing the passive blood fluid flow loop of deoxygenated blood to the lungs.

Figure 28:
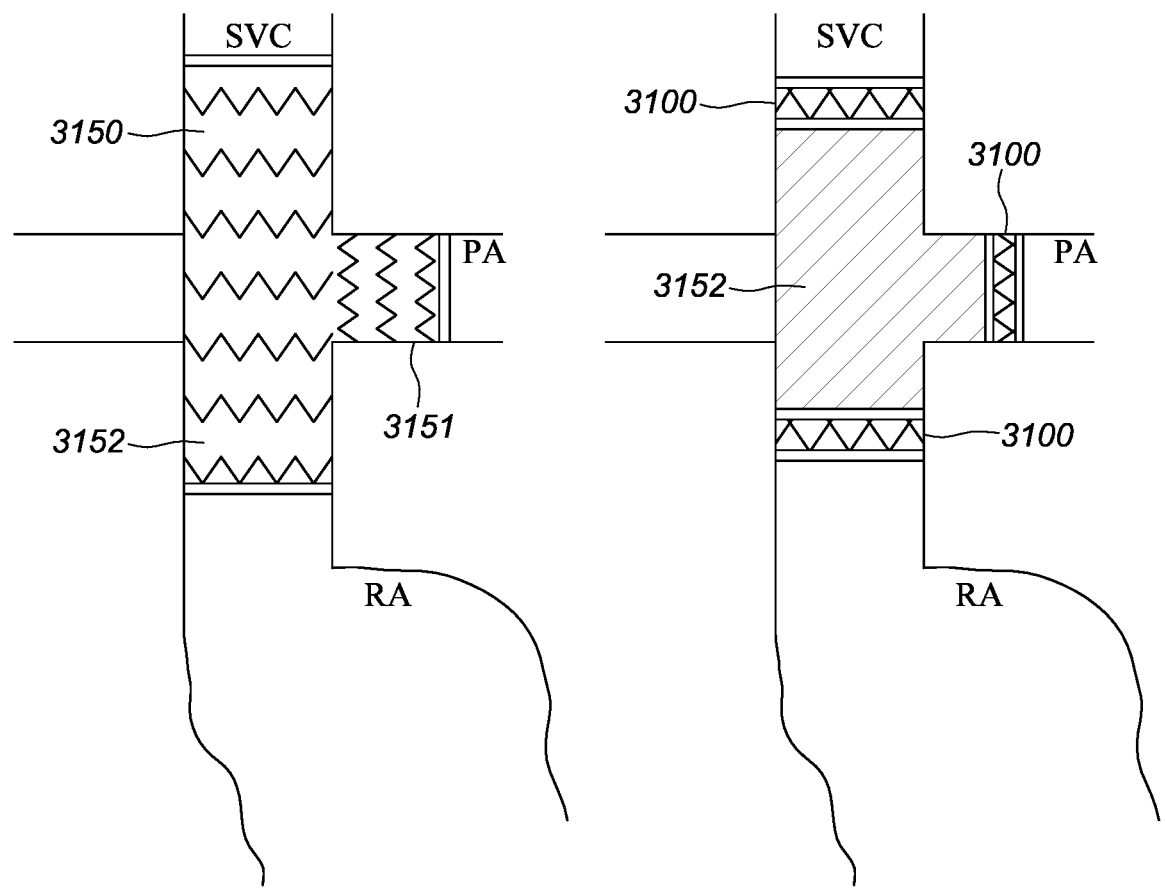
FIG. 28 is a detail drawing illustrating an exemplary embodiment of a transcatheter growth device, wherein the transcatheter growth device comprises a three-way implant system to create blood channels from the SVC, the PA, and a junction between the IVC and the RA.

Turning to FIG. 28, a transcatheter Fontan approach is shown. The transcatheter Fontan approach can be similar to that of an abdominal aortic aneurysm (or AAA) graft. The implant 3000 can be fully covered or partially covered, with impermeable cloth sewed onto the frame or having the cloth material attached through electrospinning. This embodiment of a Fontan implant system can be made from separated or attached nitinol, cobalt chrome, stainless steel, polymer, or biodegradable polymer material, or can be a combination of multiple materials attached together through cloth or other covering.

One embodiment of the Fontan implant system can involve use of multiple expandable frame rings 3100 that can be connected by impermeable cloth or covering. One embodiment contains three expandable rings 3100. This cloth connection can be reinforced with metal or polymer wires to ensure structural integrity throughout the life of the patient. The three expandable rings can be re-dilated to achieve adult vessel size as the patient develops. For the portion of the Fontan implant system, there may be a flange or flare 3151 on each of the rings to enhance fixation and blood fluid sealing.

Figure 29:
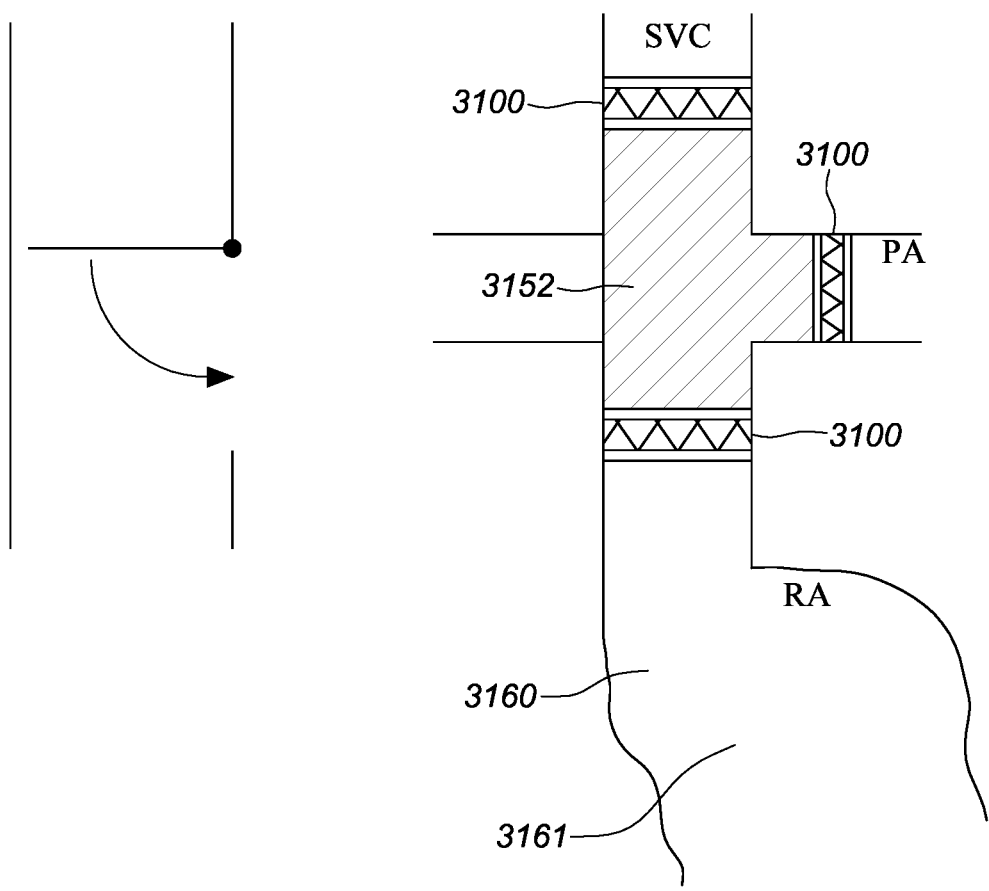
FIG. 29 is a detail drawing illustrating an exemplary embodiment of a transcatheter growth device, wherein the transcatheter growth device includes a "trap door" mechanism to strategically block off blood flow from the junction between the IVC and the RA into the SVC until called upon to open the channel.
Figure 30:
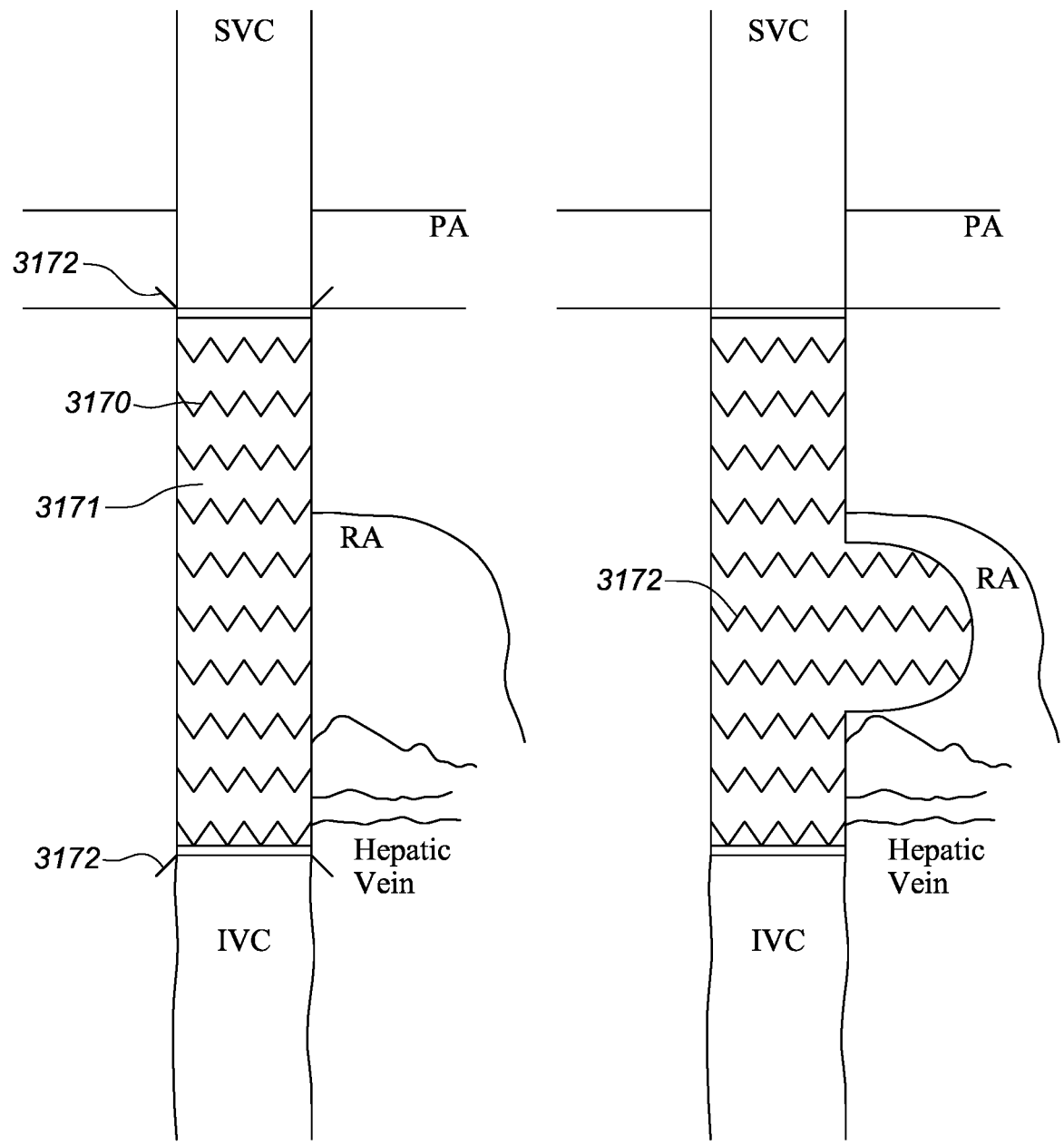
FIG. 30 is a detail drawing illustrating an exemplary embodiment of a IVC to SVC conduit implant system with fixation elements for helping to ensure no migration during growth.
Figure 31:
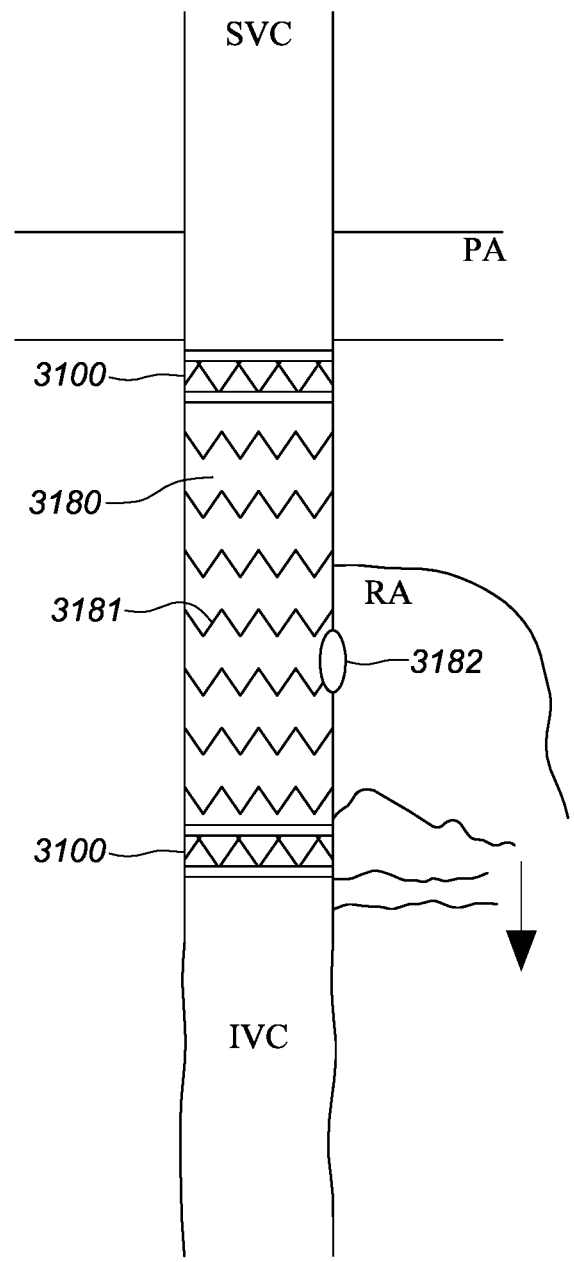
FIG. 31 is a detail drawing illustrating an exemplary embodiment of a partially covered conduit system from the IVC to SVC that comprises two implant rings and a cloth, and/or wire, components for diverting blood flow and providing structure.
Figure 32A:
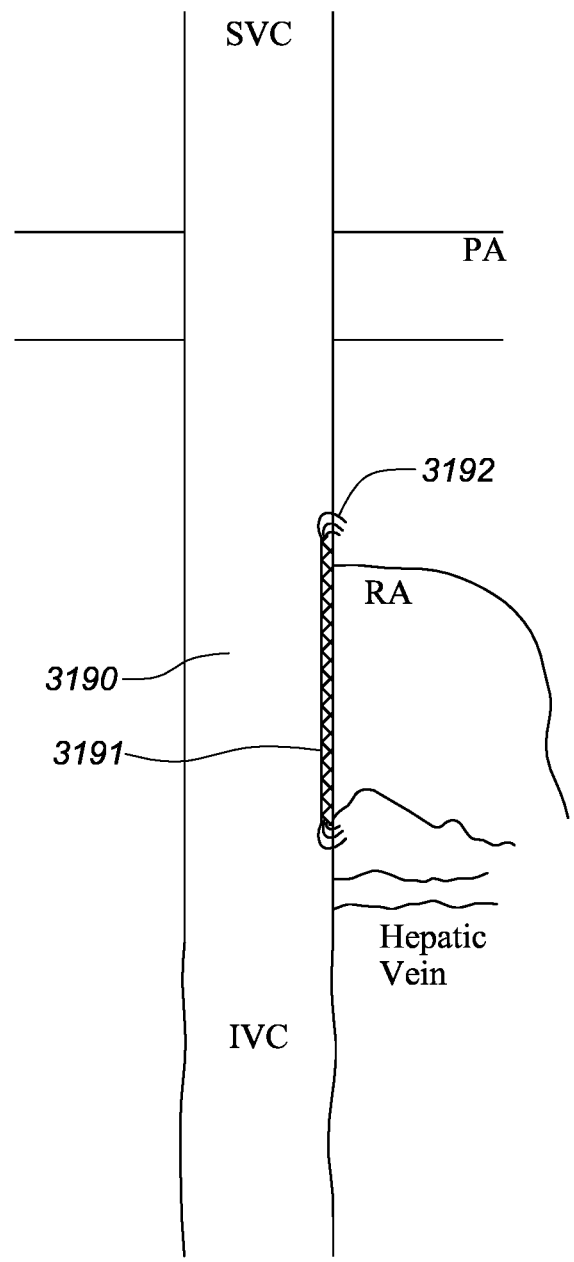
FIGS. 32A-C are detail drawings illustrating an exemplary embodiment of an implant device for diverting flow away from the RA and into the SVC.
Figure 32B:
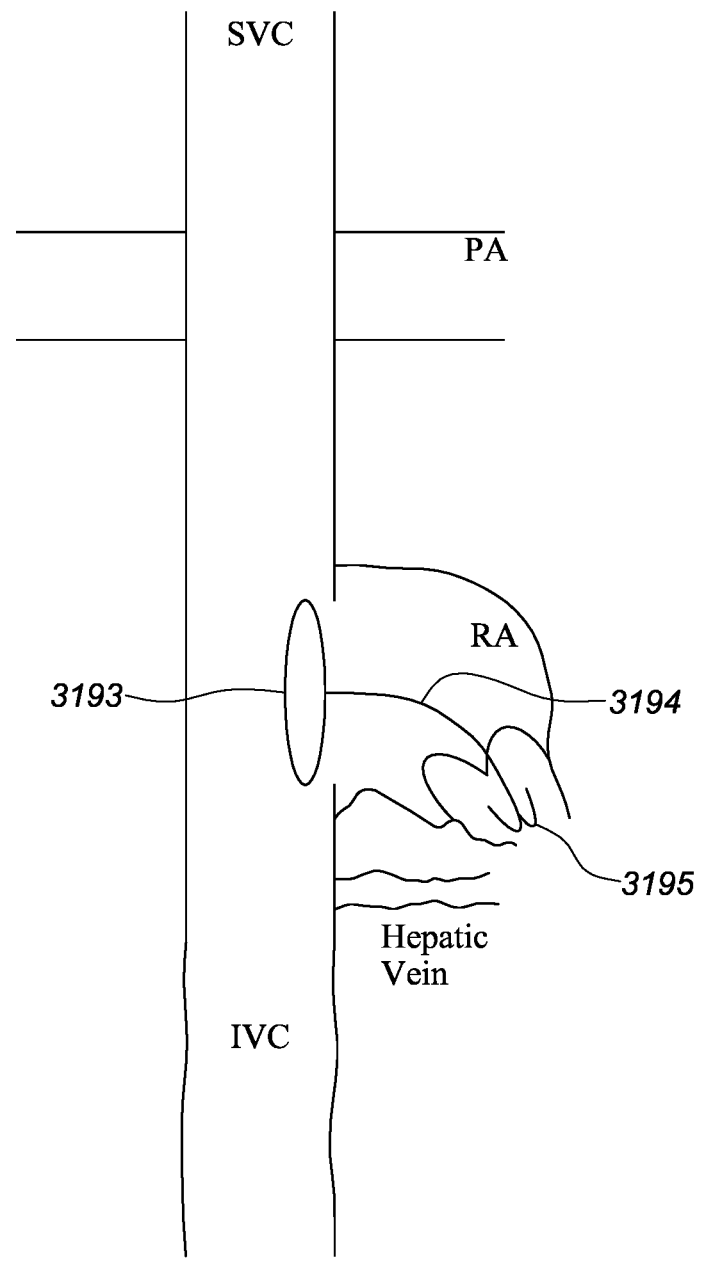
Figure 32C:
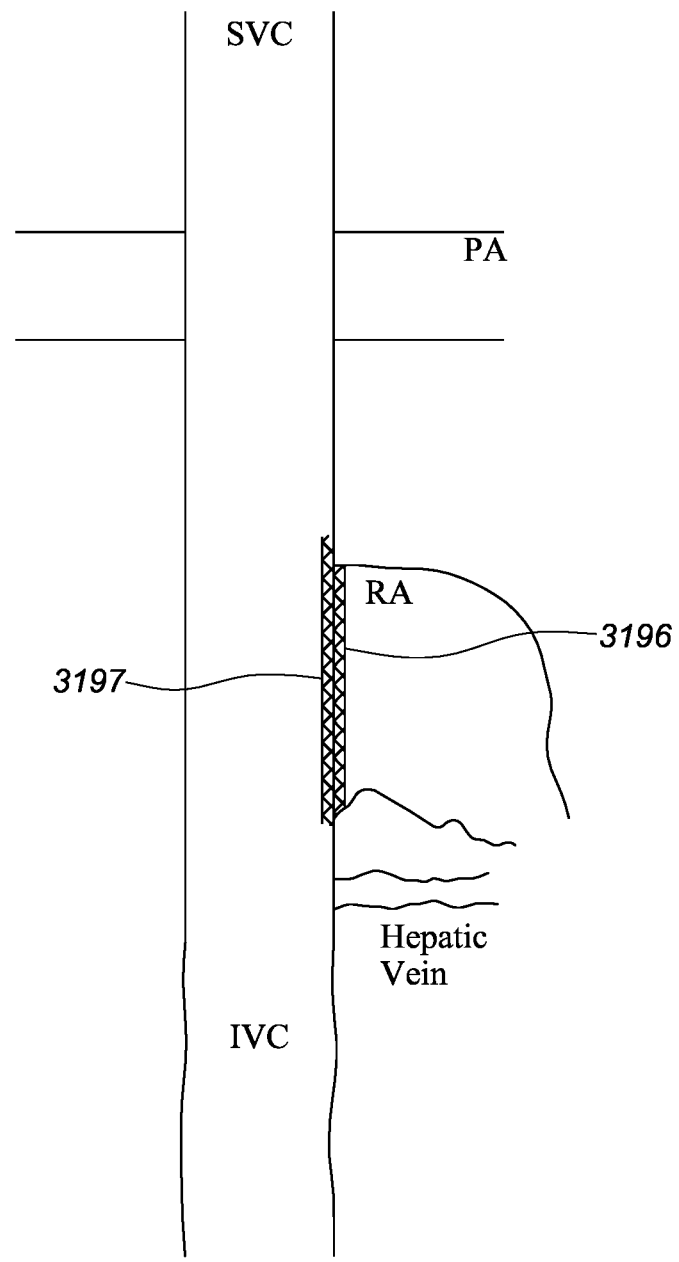
Figure 33A:
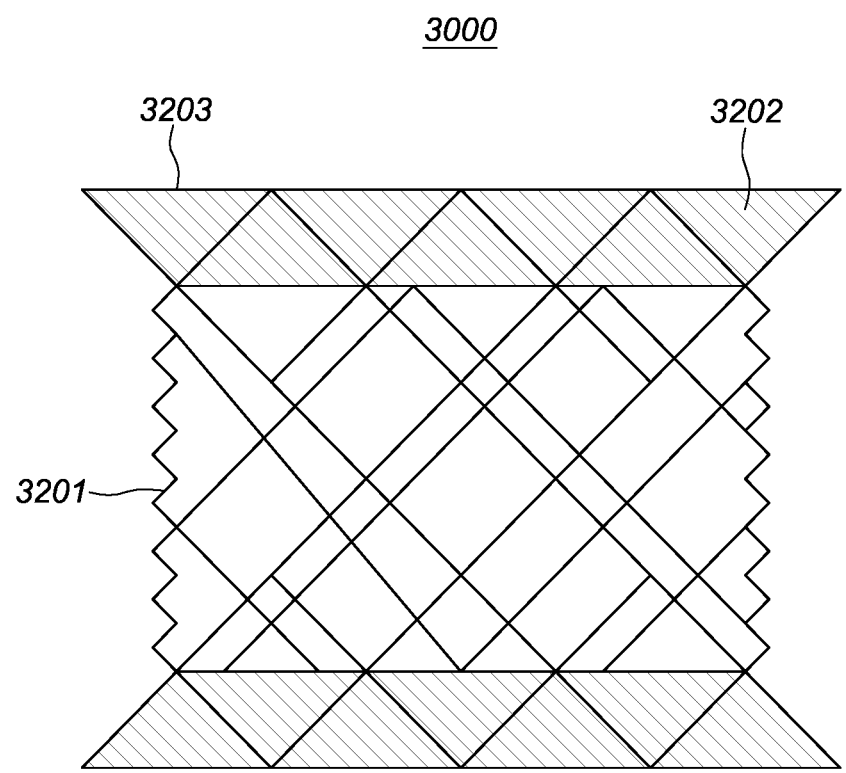
Figure 33C:
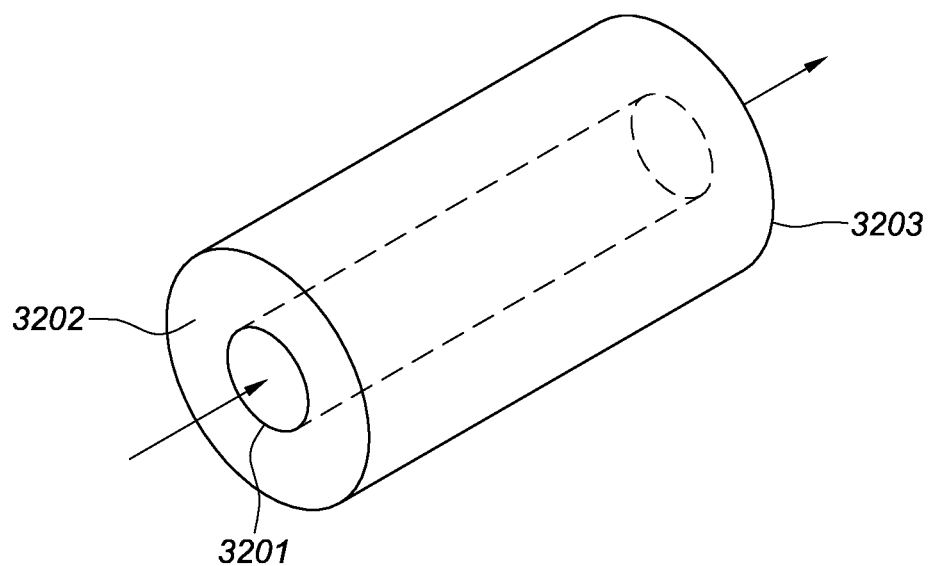
Figure 33D:
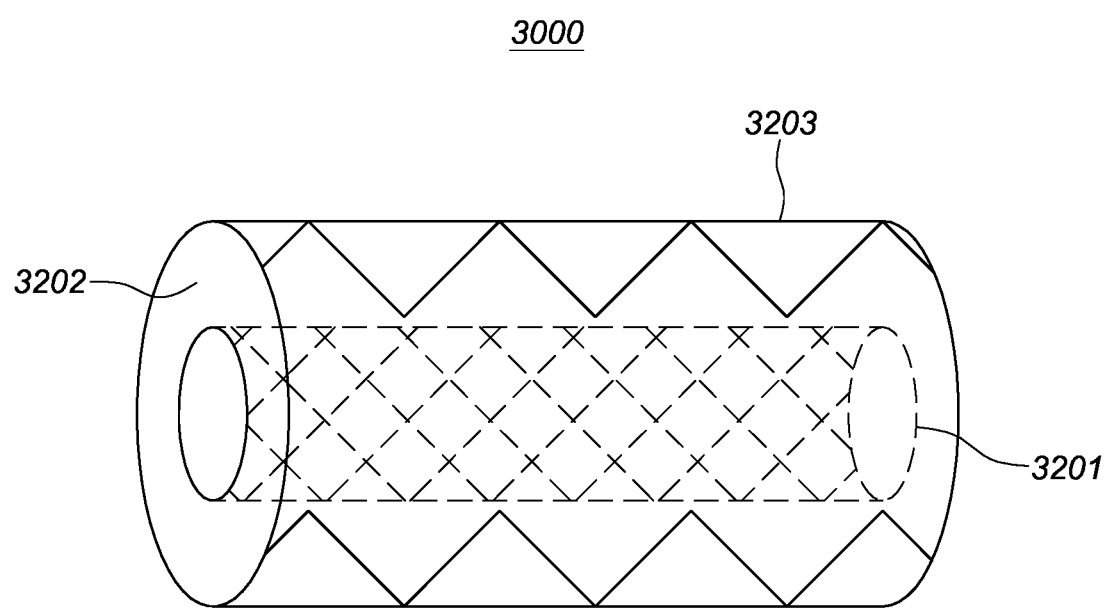

Some embodiments can include use of a trap door mechanism that can close off and open various channels of blood fluid flow as illustrated in FIG. 29. This trap door 3161 can comprise a movable blockade 3161 of blood flow that can be actuated to block a different area. In one embodiment, the door blocks the superior vena cava 121 and is then engaged to block the right atrium (or RA) 123 at a later time. The implant system may be implanted during the Glenn procedure and would have a closed off channel from the superior vena cava 121 to the right atrium 123. Once the patient is ready to receive their Fontan passive blood flow configuration, the channel would then swing open to creating a directly fluid pathway between the inferior vena cava 124 and superior vena cava 121, while blocking blood flow into the right atrium 123.

In this embodiment, the trap door can have various mechanical or material mechanisms of activation. One mechanism could be the use of wires to hinge 3160 the channel open with the support of a catheter system. Another mechanism of action could potentially utilize the shape memory material properties of nitinol. The nitinol would be deformed into a closed configuration and would have a very high austenitic final temperature. Once electrode probes are attached to the nitinol trap door 3161, and a current can be passed through the implant 3000, then the nitinol could act as a one-way actuator and open the blood flow channel.

Some embodiments include use of a transcatheter Fontan conduit to divert blood from the inferior vena cava 124 to the superior vena cava 121. This Fontan conduit may be fully or partially covered with blood impermeable cloth such as PET. The conduit can also be made from two or more expandable rings 3100 that are connected by cloth 3180, partially or fully. The cloth covering advantageously can eliminate blood fluid flow from the inferior vena cava 124 to the right atrium 123. The two-ring implant system may have wires or metal frame to provide structural support to the patency of the conduit.

In some embodiments, the Fontan conduit or flow diverting implant may be made from a biodegradable material and the cloth may provide scaffolding for tissue ingrowth. This can allow for the anatomy of the patient to grow normally while having blood fluid flow blockages that are cemented by the tissue ingrowth.

In some embodiments, the Fontan conduit or flow diverting implant may have features and frame designs that can be configured to be re-dilated to adult sizes as the anatomy of the patient is in development. This re-dilation may be manually performed with balloon expansion or may expand passively with the anatomic growth of the patient.

In some embodiments, the Fontan conduit or flow diverting implant may have a fenestration to allow for any pressure uptake from the pulmonary artery 122 to be released into the right atrium 123. The size of the fenestration can be pre-determined but can also be made from an expandable member that can be dilated to optimal size using a balloon or other mechanism. The fenestration can be located on both sizes of the conduit or only on one side. If the fenestration is located on only one side, the operator can rotate the system to their liking for the fenestration to either be present to the right atrium 123 or to either be occluded against a wall of the right atrium 123. The fenestration may have fluoroscopic marker bands to inform the operator of its location.

In some embodiments, the Fontan conduit or flow diverting implant can have an individual or combination of fixation mechanisms to ensure that there is no undesirable movement or migration once the implant 3000 is deployed. Some of these fixation mechanisms may involve the use of radial force and over expansion to ensure adequate contact against the vessel walls. Other fixation mechanisms include the use of barbs or other sharp members to penetrate and hold onto the vessel walls. One embodiment shows a fixation mechanism of having a protruding feature that extends into the right atrium 123, which can cause the feature to contact the walls of the right atrium 123 if there is any movement of the implant system.

In some embodiments, the Fontan conduit or flow diverting implant can consider a need to not block the hepatic vein 125, which is located below the right atrium 123 and in the inferior vena cava 124. This can be accomplished by having an open cell design that provides optimal spacing to ensure no blood fluid flow is blocked coming out of the hepatic vein 125.

Some embodiments demonstrate other implant mechanisms to divert fluid blood flow from the inferior vena cava 124 to the superior vena cava 121 without the use of a Fontan conduit system. These flow diverting implants can involve the use of various barriers to block fluid blood flow into the right atrium 123.

One embodiment involves the use of barb fixation connected impermeable cloth 3190 to close off the right atrium 123 from the inferior vena cava 124. The barbs can be placed at the junction between the inferior vena cava 124 and right atrium 123 and the junction between the superior vena cava 121 and the right atrium 123, in a matter where they are colinear with the IVC/SVC blood flow pathway and facing a septal direction of those junctions. The number and size of barbs can vary. The fixation members can also be tissue anchors that are comprised of a helicoil with a head for driving in the anchor. The impermeable cloth can be stretchable to account for an increase in size of the right atrium 123 during the growth of the patient 100. In selected embodiment, the cloth may have needles attached.

One embodiment involves utilizing a flat disk 3193 that utilizes the tricuspid valve leaflets as an anchoring mechanism 3194. The flow diverting implant may have one or more hooks 3194 that can perform leaflet capture onto the native tricuspid valve leaflets. Once the tricuspid valve leaflets have been captured, the flow diverting disk may be suspended by a wire (or braid) 3195 and positioned at the junction between the inferior vena cava 124 and right atrium 123 and the junction between the superior vena cava 121 and the right atrium 123. In selected embodiments, the sealing disk 3193 can be made from a nitinol braid or from a polymer material.

One embodiment involves the use of a covered ball or cage that may be deployed into the right atrium 123 or right atrial appendage (or RAA) to allow for adequate fixation. This embodiment may involve the sizing of an implant to be larger and potentially bulbous in form in one section. This can allow for a small portion anchoring in the superior vena cava 121 with the bulbous section securing into the RA or RAA to block flow.

One embodiment can comprise two disks that can block fluid blood flow from the inferior vena cava 124 to the right atrium 123, as well as fixate onto the walls of the right atrium 123. This flow diverting implant may be made from a nitinol braid that is shapeset into two disks 3196, 3197 and/or could be made from a shape memory polymer as well.

A dual implant system as shown in FIGS. 33A-D can be used to restrict flow in the pulmonary artery 122 for a transcatheter Norwood procedure. This implant could be made of a self-expanding outer frame 3203 and a balloon expandable inner frame 3201 that are coupled via a cloth connector 3202.

In some embodiments, the self-expanding outer frame 3203 can be a straight tube stent, a flared stent on both sides, or may be a self-expanding braided design. The strut designs for the self-expanding outer frame 3203 and the balloon expandable inner frame 3201 can be a diamond style design or may be a chevron strut design as illustrated in other drawings herein. The balloon expandable inner frame 3201 may have the ability to expand to a wide range of diameters depending on patient growth and their hemodynamic needs. The balloon expandable inner frame 3201 may range in diameter from less than one millimeter and up to twenty millimeters or more. The self-expanding outer frame 3203 may range in diameter from a less than one millimeter to up to seven millimeters or more. The self-expanding outer frame 4203 may be designed with a specific wall thickness or strut design to be weaker than the balloon expandable inner frame 3201 so that the balloon expandable inner frame 3201 can overpower the self-expanding outer frame 3203 once the expansions of the inner frame become larger than the outer frame. The cloth connector 3202 can be made from PTFE or another type of cloth material and can be stretchable. The cloth connector 3202 advantageously can couple the two frames and/or provide a seal to prevent blood leaks.

Figure 34:
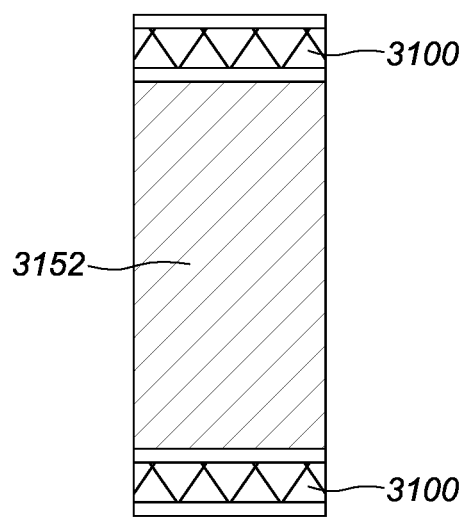
FIG. 34 is a detail drawing illustrating an exemplary embodiment of an implant device for expanding a patent ductus arteriosus (PDA).

FIG. 34 illustrates an implant design 3000 that can be utilized to expand a patent ductus arteriosus (or PDA). This PDA implant 3000 may have two expandable rings 3100 that are connected by impermeable cloth 3152. The cloth may have wires imbedded for providing structural support.

Figure 35:
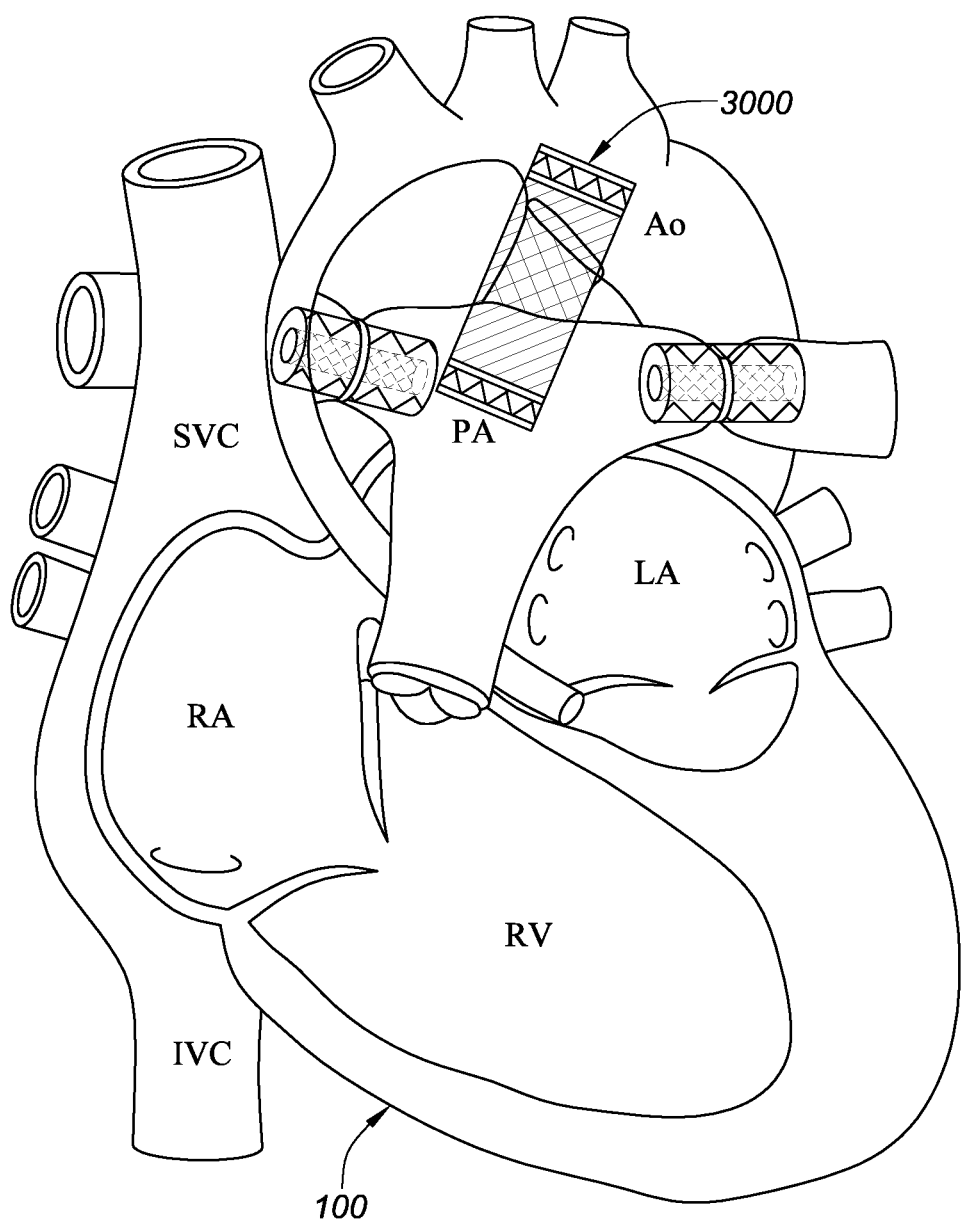
FIG. 35 is a detail drawing illustrating an exemplary embodiment of the dual frame implant device of FIGS. 33A-D and the implant device of FIG. 34, wherein the dual frame implant device and the implant device are disposed in the anatomy of a patient.

Turning to FIG. 35, one or more PA flow restrictors and a PDA stent are shown as being implanted as a transcatheter Norwood Procedure. Many of the embodiments set forth herein may be used in a transcatheter Norwood procedure.

A transvascular technique can include introducing and implanting a shunt, occluder, or conduit in neonates using a flexible catheter in a manner that is less invasive than open heart surgery. In this technique, a device such as a SVC to PA shunt, a SVC occluding device, and/or a Fontan flow diverter or conduit is in a crimped state on the end portion of a flexible catheter and advanced through a blood vessel of the patient until the specific device reaches the implantation site. The device at the catheter tip is then expanded to its functional size at the target site, such as by inflating a balloon on which the implant is mounted or through unsheathing the self-expanding implant. These implants can be later re-expanded to the size of an adult vessel with a transcatheter balloon. The implants thereby can be implanted in a neonate patient and expanded as needed throughout the lifetime of the patient.

The blood-impermeable covering allows for vessel ingrowth and seals the vessel from blood leaking through the implant systems. The covering may be of cloth material such as polyethylene terephthalate (or PET) or a fluoropolymer like some polytetrafluoroethylenes. The covering seals and performs across the range of diameters of the implant system frame and can be expanded with the frame over the lifetime of patient growth. In selected embodiments, the blood-impermeable covering can be attached at the distal and proximal end regions of the stent frame to allow for proper expansion.

The flare may be implemented in any suitable manner. One way is to outwardly curve the tips of the end region or end regions using material properties or expansion using a balloon with an outward curve shape. One or both end regions may be flared inwardly to prevent aneurysm using similar techniques. Aneurysms may be similarly prevented through dulled end regions. Dulled end regions may be created in the implant design by attaching circular eyelets or end regions of various sizes to lessen the sharpness of the frame.

In the manner discussed above, the present concept includes variations, and the optional features noted above may be added to embodiments disclosed herein, either alone or in various combinations as appropriate.

Advantageously, each embodiment described herein can have the ability to grow with the patient. In some cases, all implants may be delivered through a four French or smaller delivery sheath for neonates, infants, babies, small children, and other pediatric patients. In other embodiments, the implants may be delivered through a six French or lower sheath for neonates, infants, babies, small children, and other pediatric patients. Implants for children older than neonates, such as devices to replace the Fontan procedure, may be delivered through an eight French or smaller delivery system. The same sizing applies to delivery systems and conduits described in this application. In some embodiments, the implants can increase in size, whether naturally or via an actuating member such as a balloon catheter, to provide therapeutic solutions for the entirety of the lifetime.

A further understanding of the nature and advantages of the disclosed embodiments will become apparent by reference to the remaining portions of the specification and drawings.

In one embodiment, a catheter is advanced to the target location by way of the femoral vein or artery, depending on the endpoint. Other vessels in the patient may be utilized to properly track the delivery catheter to the intended location. The transitions in the material of the catheter allow proper trackability to the target location despite difficult anatomy.

Considering materials, implant systems may be made of a variety of materials known in the art for balloon-expanding stents or, in alternative embodiments, for self-expandable stents. As non-limiting examples, the stent may be made of any appropriate material, such as a metal or metal alloy, including stainless steel, cobalt chromium, nitinol, or elgiloy, or a polymer, for example. For self-expanding embodiments, the stent is made of a shape memory material such as, for example, nitinol.

The forgoing primarily describes embodiments of the stent that are balloon-expandable. But the delivery devices shown and described herein can be modified for delivery of self-expandable implant systems, within the scope of the present disclosure. That is to say, delivering self-expandable implant systems to an implantation location can be performed percutaneously using modified versions of the delivery devices of the present disclosure. In general terms, this includes providing a transcatheter assembly that can include a delivery sheath and/or additional sheaths as described above. The devices generally further include a delivery catheter, a balloon catheter, and/or a guide wire.

As used herein, a phrase in the form of at least one of A, B, C and D herein is to be construed as meaning one or more of A, one or more of B, one or more of C and/or one or more of D. Likewise, a phrase in the form of A, B, C or D as used herein is to be construed as meaning A or B or C or D. For example, a phrase in the form of A, B, C or a combination thereof is to be construed as meaning A or B or C or any combination of A, B and/or C.

In view of the many possible embodiments to which the principles disclosed herein may be applied, it should be recognized that the illustrated embodiments are only preferred examples of the invention and should not be taken as limiting the scope of the invention. It should be further recognized, for example, that features discussed with reference to a specific embodiment can be applied to any other embodiment disclosed herein. The scope of the invention thus is defined by the following claims. We therefore claim as our invention all that comes within the scope and spirit of these claims.

The described embodiments are susceptible to various modifications and alternative forms, and specific examples thereof have been shown by way of example in the drawings and are herein described in detail. It should be understood, however, that the described embodiments are not to be limited to the particular forms or methods disclosed, but to the contrary, the present disclosure is to cover all modifications, equivalents, and alternatives.

What is claimed is:

1. A transcatheter growth device for treating congenital illnesses in heart disease patients, comprising:
    a first elongated device frame having a first annular spacing member in axial alignment between a proximal annular growth cell member and a distal annular growth cell member and being in an implantation state for facilitating insertion into a first lumen of a patient, the first annular spacing member, the proximal annular growth cell member and the distal annular growth cell member cooperating to define a first radial device periphery;
    a first covering member being disposed around the first device periphery of said first device frame; and
    one or more retention members being distributed about the first device periphery at the distal annular growth cell member and being configured to extend radially from the first device periphery and to engage a second lumen in communication with the first lumen when deployed,
    wherein said growth device is configured to be deployed within the first lumen with said first device frame being expanded from the implantation state to a first stable expanded state with the first device periphery supporting the first lumen and defining a central axial channel for promoting blood flow between the first and second lumens, said first covering member being configured to provide a radial seal at an intersection between the first and second lumens, and
    wherein said first device frame is configured to subsequently radially re-expand from the first stable expanded state to a second stable expanded state as the first lumen of the patient grows from a first dimension to a second dimension, the first device periphery supporting the first lumen with the second dimension.

2. The transcatheter growth device of claim 1, wherein said first device frame further comprises at least one intermediate annular spacing member alternating with at least one intermediate annular growth cell member being disposed in axial alignment between the first annular spacing member and the proximal annular growth cell member and cooperate to further define the first device periphery.

3. The transcatheter growth device of claim 2, wherein each of the proximal annular growth cell member, the distal annular growth cell member and each intermediate annular growth cell member includes a first annular strut arrangement and a second annular strut arrangement,
    wherein the first annular strut arrangement comprises a plurality of paired first growth cell struts with each first growth cell strut having a proximal end region and a distal end region, the proximal end regions of the paired first growth cell struts being coupled such that the distal end regions extend from the coupled proximal end regions, the distal end regions of adjacent paired first growth cell struts being coupled to form the first annular strut arrangement with a zigzag arrangement of the first growth cell struts, and
    wherein the second annular strut arrangement comprises a plurality of paired second growth cell struts with each second growth cell strut having a proximal end region and a distal end region, the proximal end regions of the paired second growth cell struts being coupled such that the distal end regions extend from the coupled proximal end regions, the distal end regions of adjacent paired second growth cell struts being coupled to form the second annular strut arrangement with a zigzag arrangement of the second growth cell struts.

4. The transcatheter growth device of claim 3, wherein the first annular spacing member and each intermediate annular spacing member comprises a plurality of elongated spacer member struts with each spacer member strut having a proximal end region and a distal end region, each of the proximal end regions of the spacer member struts being coupled with the coupled proximal end region of a corresponding one of the paired first growth cell struts of the first annular strut arrangement of a first adjacent annular growth cell member, each of the distal end regions of the spacer member struts being coupled with the coupled proximal end region of a corresponding one of the paired second growth cell struts of the second annular strut arrangement of a second adjacent annular growth cell member.

5. The transcatheter growth device of claim 4, wherein the first annular spacing member and each intermediate annular spacing member are configured to reduce foreshortening of a length of said first device frame during expansion from the implantation state to the first stable expanded state.

6. The transcatheter growth device of claim 4,
    wherein each of the proximal end regions of the spacer member struts are coupled with the coupled proximal end region of the corresponding one of the paired first growth cell struts of the first annular strut arrangement of the first adjacent annular growth cell member via a first intermediate coupling member, and
    wherein each of the distal end regions of the spacer member struts are coupled with the coupled proximal end region of the corresponding one of the paired second growth cell struts of the second annular strut arrangement of the second adjacent annular growth cell member via a second intermediate coupling member.

7. The transcatheter growth device of claim 6,
    wherein each first intermediate coupling member comprises a first flexible central body with a first coupling region for coupling with a corresponding coupled proximal end region of the selected one of the paired first growth cell struts of the first annular strut arrangement of the first adjacent annular growth cell member and a second coupling region for coupling with the proximal end region of a selected spacer member strut, and
    wherein each second intermediate coupling member comprises a second flexible central body with a first coupling region for coupling with a corresponding coupled proximal end region of the selected one of the paired second growth cell struts of the second annular strut arrangement of the second adjacent annular growth cell member and a second coupling region for coupling with the distal end region of the selected spacer member strut.

8. The transcatheter growth device of claim 6, wherein the first and second intermediate coupling members provide flexibility for said device frame.

9. The transcatheter growth device of claim 3, wherein the first annular strut arrangement and the second annular strut arrangement of one or more of the proximal annular growth cell member, a selected intermediate annular growth cell member and the distal annular growth cell member are coupled via said first covering member.

10. The transcatheter growth device of claim 3, wherein the coupled distal end regions of a predetermined one of the adjacent paired first growth cell struts of a selected annular growth cell member are coupled with the coupled distal end regions of a corresponding one of the adjacent paired second growth cell struts of the selected annular growth cell member to form a growth cell junction for coupling the first and second annular strut arrangements of the selected annular growth cell member.

11. The transcatheter growth device of claim 10, wherein the selected annular growth cell member comprises the distal annular growth cell member.

12. The transcatheter growth device of claim 11, wherein a retention member is coupled with the growth cell junction and configured to extend radially from the distal annular growth cell member and to engage the second lumen when deployed.

13. The transcatheter growth device of claim 3,
wherein the coupled distal end regions of a predetermined one of the adjacent paired first growth cell struts of the proximal annular growth cell member are coupled with the coupled distal end regions of a corresponding one of the adjacent paired second growth cell struts of the proximal annular growth cell member to form a first growth cell junction for coupling the first and second annular strut arrangements of the proximal annular growth cell member,
wherein the coupled distal end regions of a predetermined one of the adjacent paired first growth cell struts of the intermediate annular growth cell member are coupled with the coupled distal end regions of a corresponding one of the adjacent paired second growth cell struts of the intermediate annular growth cell member to form a second growth cell junction for coupling the first and second annular strut arrangements of the intermediate annular growth cell member, and
wherein the coupled distal end regions of a predetermined one of the adjacent paired first growth cell struts of the distal annular growth cell member are coupled with the coupled distal end regions of a corresponding one of the adjacent paired second growth cell struts of the distal annular growth cell member to form a third growth cell junction for coupling the first and second annular strut arrangements of the distal annular growth cell member.

14. The transcatheter growth device of claim 13, wherein the first, second and third growth cell junctions provide flexibility for said device frame.

15. The transcatheter growth device of claim 1, wherein said device frame is formed from a self-expanding metal material.

16. The transcatheter growth device of claim 1, wherein said first covering member is disposed outside the first device periphery of said first device frame.

17. The transcatheter growth device of claim 1, wherein said first covering member is disposed around the first device periphery along an axial length of said first device frame between the proximal annular growth cell member and the distal annular growth cell member.

18. The transcatheter growth device of claim 1, wherein said first covering member comprises a fluid-impermeable material.

19. A transcatheter growth system for treating congenital illnesses in heart disease patients, comprising:
said transcatheter growth device of claim 1; and
a second transcatheter growth device being configured to cooperate with said transcatheter growth device and comprising:
a second elongated device frame having a second annular spacing member in axial alignment between a proximal annular growth cell member and a distal annular growth cell member and being in an implantation state for facilitating insertion into the first lumen of the patient, the second annular spacing member, the proximal annular growth cell member and the distal annular growth cell member cooperating to define a second radial device periphery;
an anchor member being disposed on the second device periphery of said second device frame; and
a second covering member being disposed around the second device periphery of said second device frame,
wherein said second growth device is configured to be deployed within the first lumen with said second device frame being expanded from the implantation state to a first stable expanded state with the second device periphery supporting the first lumen and defining a central axial channel for promoting blood flow between the first lumen and a third lumen in communication with the first lumen, said anchor member being configured to extend radially from the second device periphery and to engage the third lumen, said second covering member being configured to provide a radial seal at an intersection between the first and third lumens.

20. The transcatheter growth system of claim 19, wherein said second device frame further comprises at least one intermediate annular spacing member alternating with at least one intermediate annular growth cell member being disposed in axial alignment between the second annular spacing member and the proximal annular growth cell member of said second device frame and cooperate to further define the second device periphery.

21. The transcatheter growth system of claim 20, wherein each of the proximal annular growth cell member, the distal annular growth cell member and each intermediate annular growth cell member of said second device frame includes a first annular strut arrangement and a second annular strut arrangement,
wherein the first annular strut arrangement comprises a plurality of paired first growth cell struts with each first growth cell strut having a proximal end region and a distal end region, the proximal end regions of the paired first growth cell struts being coupled such that the distal end regions extend from the coupled proximal end regions, the distal end regions of adjacent paired first growth cell struts being coupled to form the first annular strut arrangement with a zigzag arrangement of the first growth cell struts, and
wherein the second annular strut arrangement comprises a plurality of paired second growth cell struts with each second growth cell strut having a proximal end region and a distal end region, the proximal end regions of the paired second growth cell struts being coupled such that the distal end regions extend from the coupled proximal end regions, the distal end regions of adjacent paired second growth cell struts being coupled to form the second annular strut arrangement with a zigzag arrangement of the second growth cell struts.

22. The transcatheter growth system of claim 21, wherein the coupled distal end regions of a predetermined one of the adjacent paired first growth cell struts of a selected annular growth cell member of said second device frame are coupled with the coupled distal end regions of a corresponding one of the adjacent paired second growth cell struts of the selected annular growth cell member to form a growth cell junction for coupling the first and second annular strut arrangements of the selected annular growth cell member.

23. The transcatheter growth system of claim 22, wherein the selected annular growth cell member comprises a selected intermediate annular spacing member of said second device frame.

24. The transcatheter growth system of claim 23, wherein said anchor member is coupled with the growth cell junction and configured to extend radially from the selected intermediate annular spacing member when deployed.

25. The transcatheter growth system of claim 21, wherein said second covering member is disposed around the second device periphery along an axial length of said second device frame between the distal annular growth cell member of said second device frame and said anchor member.

26. The transcatheter growth system of claim 21, wherein the distal annular growth cell member of said first device frame when deployed is configured to receive the distal annular growth cell member of said second device frame, said second device frame being in axial alignment with said first device frame with the proximal end region of said second device frame extending from the distal annular growth cell member of said first device frame.

27. The transcatheter growth system of claim 26, wherein said first and second device frame are configured to deploy in a telescoping arrangement for adjusting a distance between said retention members and said anchor member to conform with a predetermined distance between the second and third lumens of the patient.

28. The transcatheter growth system of claim 21, wherein said first device frame is further configured to subsequently radially re-expand from the first stable expanded state to a second stable expanded state and said second device frame is further configured to subsequently radially re-expand from the first stable expanded state to a second stable expanded state as the first lumen of the patient grows from a first dimension to a second dimension, the first and second device peripheries supporting the first lumen with the second dimension.

* * * * *